(12) United States Patent
Kostik et al.

(10) Patent No.: US 8,637,704 B2
(45) Date of Patent: Jan. 28, 2014

(54) POLYMORPHS OF N-MALONYL-BIS(N'-METHYL-N'-THIOBENZOYLHYDRAZIDE)

(75) Inventors: Elena Kostik, Arlington, MA (US); Lijun Sun, Harvard, MA (US); Joanna Dziewiszek, Boxborough, MA (US); Jun Y. Choi, Lexington, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 416 days.

(21) Appl. No.: 12/745,096

(22) PCT Filed: Nov. 28, 2008

(86) PCT No.: PCT/US2008/013204
§ 371 (c)(1), (2), (4) Date: Dec. 23, 2010

(87) PCT Pub. No.: WO2009/073148
PCT Pub. Date: Jun. 11, 2009

(65) Prior Publication Data
US 2011/0196025 A1 Aug. 11, 2011

Related U.S. Application Data

(60) Provisional application No. 61/004,476, filed on Nov. 28, 2007, provisional application No. 61/004,740, filed on Nov. 29, 2007.

(51) Int. Cl.
*C07C 327/56* (2006.01)
*A61K 31/166* (2006.01)

(52) U.S. Cl.
USPC .......................................... 564/74; 514/599

(58) Field of Classification Search
USPC ............................................ 564/74; 514/599
See application file for complete search history.

(56) References Cited

U.S. PATENT DOCUMENTS

| 4,927,822 A | 5/1990 | Brown et al. |
| 7,645,904 B2 * | 1/2010 | Chen et al. ............... 564/74 |

FOREIGN PATENT DOCUMENTS

| EP | 1671957 | 6/2006 |
| WO | WO 03/006429 | 1/2003 |
| WO | WO 03/006430 | 1/2003 |
| WO | WO 2004/064826 | 8/2004 |
| WO | WO 2008/033494 | 3/2008 |

OTHER PUBLICATIONS

Carter et al., Chemotherapy of Cancer, second edition, John Wiley & Sons, N.Y., N.Y., 1981, pp. 362-365.*
PCT International Search Report and Written Opinion—(PCT/US2008/013204) Date of Mailing Aug. 5, 2009.
PCT International Search Report and Written Opinion—(PCT/US2008/013203) Date of Mailing Mar. 16, 2010.
Biswas, et al., "Novel Ligational Behaviour or Thiosalicylohydrazide and Its Derivatives with Cobalk(II), Nickel(II), Copper(II), and Palladium(II)," J. Chem. Soc. Transactions, 1981, vol. 12, pp. 2385-2394.
Jensen, et al., "Complexes de Nickel avec la Thiobenzhydrazide et avec des Composes Analogues," Acta Chemica Scandinavica, 1952, vol. 6, pp. 189-194.
Jensen, et al., "Studies of Thioacids and Their Derivatives," Acta Chemica Scandinavica, 1961, vol. 6, pp. 1109-1123.
Kalinowski, et al., "Design, Synthesis, and Characterization of New Iron Chelators with Anti-Proliferative Activity: Structure-Activity Relationships of Novel Thiohydrazone Analogues," J. Med. Chem., 2007, vol. 50, pp. 6212-6225.

* cited by examiner

*Primary Examiner* — Shailendra Kumar
(74) *Attorney, Agent, or Firm* — McCarter & English, LLP; Steven G. Davis

(57) ABSTRACT

At least 70% by weight of Compound 1 is the single crystalline form, Form A, Form C, or Form D, of the compound. A pharmaceutical composition comprises a pharmaceutically acceptable carrier or diluent, and compound 1, wherein at least 70% by weight of the compound is the single crystalline form, Form A, Form C, or Form D, of the compound. A method of treating a subject with cancer comprises administering to the subject an effective amount of compound 1 or the pharmaceutical composition.

(compound 1)

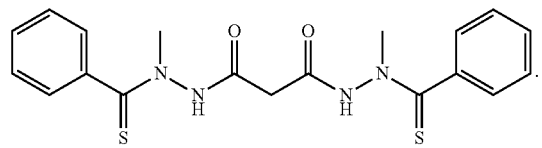

17 Claims, 39 Drawing Sheets

POLYMORPHS OF
N-MALONYL-BIS(N'-METHYL-N'-
THIOBENZOYLHYDRAZIDE)

RELATED APPLICATIONS

This application is a U.S. National Stage of International Application No. PCT/US08/13204, filed on Nov. 28, 2008, which claims the benefit of U.S. Provisional Application No. 61/004,740, filed on Nov. 29, 2007 and U.S. Provisional Application No. 61/004,476, filed on Nov. 28, 2007. The entire teachings of the above applications are incorporated herein by reference.

BACKGROUND OF THE INVENTION

It has been reported in U.S. Pat. Nos. 6,800,660; 6,762,204; 7,037,940; 7,001,923; and 6,924,312 that certain bis (thiohydrazide amide) compounds significantly enhance the anticancer activity of paclitaxel and paclitaxel analogs. In particular, N-malonyl-bis(N'-methyl-N'-thiobenzoylhydrazide) in combination with taxol has been shown to increase the time to progression of patients suffering from stage IV metastatic melanoma relative to patients treated with paclitaxel alone. It would be advantageous to have crystalline forms of N-malonyl-bis(N'-methyl-N'-thiobenzoylhydrazide) having properties that are suitable for large-scale manufacture (e.g., dry powder fill) of the compound as a drug.

SUMMARY OF THE INVENTION

Applicants have now discovered several polymorphs of compound 1 represented by the following structure:

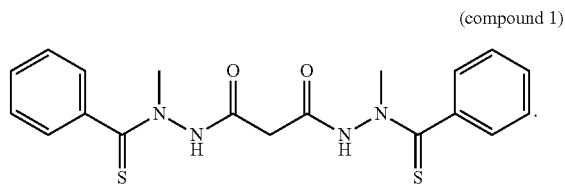 [SMILES: CN(NC(=O)CC(=O)NN(C)C(=S)c1ccccc1)C(=S)c1ccccc1]

(compound 1)

In one embodiment, the invention is directed to compound 1 wherein at least 70% by weight of the compound is the single crystalline form Form A of the compound.

In another embodiment, the invention is directed to compound 1 wherein at least 70% by weight of the compound is the single crystalline form Form C of the compound.

In yet another embodiment, the invention is directed to compound 1 wherein at least 70% by weight of the compound is the single crystalline form Form D of the compound.

In yet another embodiment, the invention is directed to compound 1 wherein at least 70% by weight of the compound is crystal habit .1 of the single crystalline form Form A of the compound.

In yet another embodiment, the invention is directed to compound 1 wherein at least 70% by weight of the compound is crystal habit 2 of the single crystalline form Form A of the compound.

In yet another embodiment, the invention is directed to a pharmaceutical composition comprising a pharmaceutically acceptable carrier or diluent, and compound 1, wherein at least 70% by weight of the compound is the single crystalline form Form A of the compound.

In yet another embodiment, the invention is directed to a pharmaceutical composition comprising a pharmaceutically acceptable carrier or diluent, and compound 1, wherein at least 70% by weight of the compound is the single crystalline form Form C of the compound.

In yet another embodiment, the invention is directed to a pharmaceutical composition comprising a pharmaceutically acceptable carrier or diluent, and compound 1, wherein at least 70% by weight of the compound is the single crystalline form Form D of the compound.

In yet another embodiment, the invention is directed to a pharmaceutical composition comprising a pharmaceutically acceptable carrier or diluent, and compound 1, wherein at least 70% by weight of the compound is crystal habit 1 of the single crystalline form Form A of the compound.

In yet another embodiment, the invention is directed to a pharmaceutical composition comprising a pharmaceutically acceptable carrier or diluent, and compound 1, wherein at least 70% by weight of the compound is crystal habit 2 of the single crystalline form Form A of the compound.

A method of treating a subject with cancer is also encompassed by the invention. The method comprises administering to the subject an effective amount of a compound or a pharmaceutical composition of the invention disclosed herein.

A method of treating a subject with cancer comprising administering to the subject an effective amount of paclitaxel or a paclitaxel analog, and an effective amount of a compound or a pharmaceutical composition of the invention disclosed herein is also encompassed by the invention.

The invention also includes the use of a compound or a pharmaceutical composition of the invention disclosed herein for treating cancer.

The invention also includes the use of an effective amount of paclitaxel or a paclitaxel analog, and an effective amount of a compound or a pharmaceutical composition of the invention disclosed herein for treating cancer.

Also included in the invention is the use of a compound or a pharmaceutical composition of the invention disclosed herein for the manufacture of a medicament for treating cancer in a subject.

Also included in the invention is the use of paclitaxel or a paclitaxel analog, and a compound or a pharmaceutical composition of the invention disclosed herein, for the manufacture of a medicament for treating cancer in a subject.

DETAILED DESCRIPTION OF THE INVENTION

Figure 1:
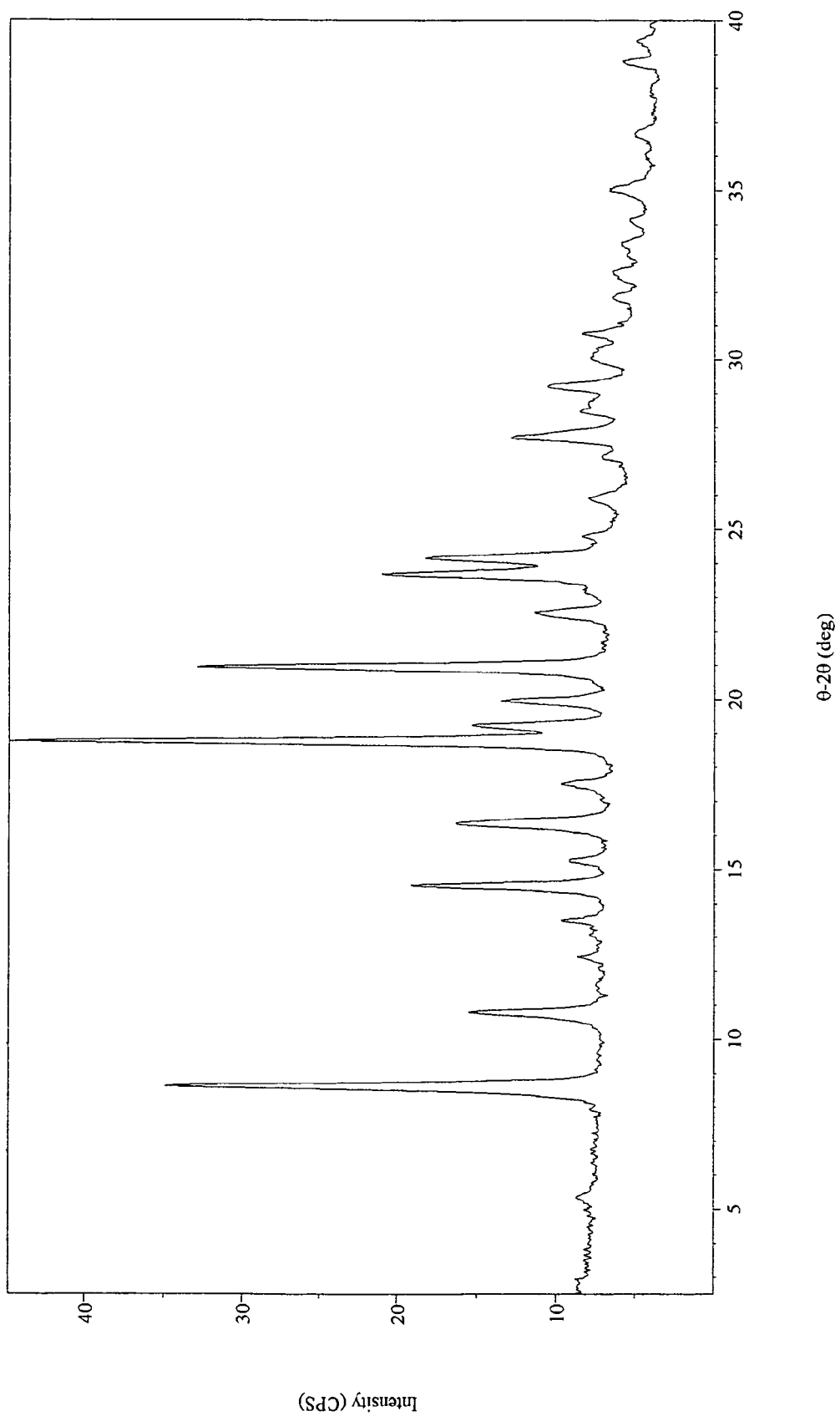
FIG. 1 is an XRPD (X-ray powder diffraction) pattern obtained from a sample of Form A of compound 1.

The present invention provides unique crystalline forms of compound 1 and new compositions and pharmaceutical compositions comprising the crystalline forms of compound 1 described herein. The present invention also provides methods of treating a subject with cancer. Additionally, the present invention provides methods of preparing the crystalline forms described herein.

In one embodiment of the invention, at least a particular percentage by weight of compound 1 is the single crystalline form Form A of compound 1. Particular weight percentages include 70%, 72%, 75%, 77%, 80%, 82%, 85%, 87%, 90%, 92%, 95%, 97%, 99%, 99.5%, 99.9%, or a percentage between 70% and 100%.

In one embodiment of the invention, at least a particular percentage by weight of compound 1 is crystal habit 1 of the single crystalline form Form A of compound 1. Particular weight percentages include 70%, 72%, 75%, 77%, 80%, 82%, 85%, 87%, 90%, 92%, 95%, 97%, 99%, 99.5%, 99.9%, or a percentage between 70% and 100%.

In one embodiment of the invention, at least a particular percentage by weight of compound 1 is crystal habit 2 of the single crystalline form Form A of compound 1. Particular weight percentages include 70%, 72%, 75%, 77%, 80%, 82%, 85%, 87%, 90%, 92%, 95%, 97%, 99%, 99.5%, 99.9%, or a percentage between 70% and 100%.

In one embodiment of the invention, at least a particular percentage by weight of compound 1 is the single crystalline form Form C of compound 1. Particular weight percentages include 70%, 72%, 75%, 77%, 80%, 82%, 85%, 87%, 90%, 92%, 95%, 97%, 99%, 99.5%, 99.9%, or a percentage between 70% and 100%.

In one embodiment of the invention, at least a particular percentage by weight of compound 1 is the single crystalline form Form D of compound 1. Particular weight percentages include 70%, 72%, 75%, 77%, 80%, 82%, 85%, 87%, 90%, 92%, 95%, 97%, 99%, 99.5%, 99.9%, or a percentage between 70% and 100%.

As used herein, "crystalline" refers to a solid having a highly regular chemical structure. A single crystalline form means compound 1 as a single crystal or a plurality of crystals in which each crystal has the same crystalline form.

When a particular percentage by weight of compound 1 is a single crystalline form, the remainder of compound 1 is some combination of amorphous compound 1 and/or one or more crystalline forms of compound 1 excluding the single crystalline form. When the crystalline compound 1 is defined as one particular form of compound 1, the remainder is made up of amorphous form and/or crystalline forms other than the one or more particular forms that are specified. Examples of a single crystalline form include Forms A, C and D of compound 1, as well as descriptions of a single crystalline form characterized by one or more properties as discussed herein.

In one embodiment, at least 70%, 72%, 75%, 77%, 80%, 82%, 85%, 87%, 90%, 92%, 95%, 97%, 99%, 99.5%, 99.9%, or a percentage between 70% and 100% by weight of the compound 1 is the single crystalline form Form D of compound 1 and at least 95% of the remainder of the compound 1 is the single crystalline form Form A of compound 1.

In one embodiment, at least 70%, 72%, 75%, 77%, 80%, 82%, 85%, 87%, 90%, 92%, 95%, 97%, 99%, 99.5%, 99.9%, or a percentage between 70% and 100% by weight of the compound 1 is the single crystalline form. Form C of compound 1 and at least 95% of the remainder of the compound 1 is the single crystalline form Form A of compound 1.

In one embodiment, at least 70%, 72%, 75%, 77%, 80%, 82%, 85%, 87%, 90%, 92%, 95%, 97%, 99%, 99.5%, 99.9%, or a percentage between 70% and 100% by weight of the compound 1 is the single crystalline form Form A of compound 1 and at least 95% of the remainder of the compound 1 is the single crystalline form Form D of compound 1.

In one embodiment, at least 70%, 72%, 75%, 77%, 80%, 82%, 85%, 87%, 90%, 92%, 95%, 97%, 99%, 99.5%, 99.9%, or a percentage between 70% and 100% by weight of the compound 1 is the single crystalline form Form A of compound 1 and at least 95% of the remainder of the compound 1 is the single crystalline form Form C of compound 1.

In another embodiment of the invention, a pharmaceutical composition comprises a pharmaceutically acceptable carrier or diluent and compound 1, wherein at least a particular percentage by weight of the compound 1 is a single crystalline form of compound 1. Particular percentages include 70%, 72%, 75%, 77%, 80%, 82%, 85%, 87%, 90%, 92%, 95%, 97%, 99%, 99.5%, 99.9%, or a percentage between 70% and 100%. In one embodiment, the single crystalline form is Form A of compound 1. In another embodiment, the single crystalline form is Form C of compound 1. In another embodiment, the single crystalline form is Form D of compound 1.

In another embodiment of the invention, a pharmaceutical composition comprises a pharmaceutically acceptable carrier or diluent and compound 1, wherein at least a particular percentage by weight of the compound 1 is a single crystal habit of Form A of compound 1. Particular percentages include 70%, 72%, 75%, 77%, 80%, 82%, 85%, 87%, 90%, 92%, 95%, 97%, 99%, 99.5%, 99.9%, or a percentage between 70% and 100%. In one embodiment, the single crystal habit is crystal habit 1 of Form A of compound 1. In another embodiment, the single crystal habit is crystal habit 2 of Form A of compound 1.

In the following description of particular crystalline forms of compound 1, embodiments of the invention may be described with reference to a particular crystalline "Form" of compound 1. However, the particular crystalline forms of compound 1 may also be characterized by one or more of the characteristics of the crystalline forms as described herein, with or without referencing a particular "Form".

Form A

In one embodiment of the invention, a single crystalline form of compound 1 is characterized as Form A. This crystalline form is also characterized by the X-ray powder diffraction (herein referred to as "XRPD") pattern shown in FIG. 1 with values of 2θ angles, d-spacing and relative intensities as listed in Table 1, obtained using Cu—Kα radiation. In a specific embodiment, the crystalline form Form A of compound 1 is characterized by one, two or three major XRPD peaks at 2θ angle selected from the group consisting of 10.76°, 14.49° and 16.33°. In another specific embodiment, the crystalline form Form A of compound 1 is characterized by major XRPD peaks at 2θ angle of 8.60°, 10.76°, 14.49°, 16.33°, 18.74°, 19.18°, 20.92°, 23.65° and 24.12°. It is to be understood that a specified 2θ angle means the specified value±0.1°.

TABLE 1

XRPD Peaks for FIG. 1

| Position (°2θ) | d-spacing (Å) | I/Io[a] |
|---|---|---|
| 8.60 | 10.27 | 72 |
| 10.76 | 8.21 | 22 |
| 12.40 | 7.13 | 4 |
| 13.48 | 6.56 | 6 |
| 14.49 | 6.11 | 32 |
| 15.24 | 5.81 | 6 |
| 16.33 | 5.42 | 26 |
| 17.49 | 5.07 | 8 |
| 18.74 | 4.73 | 100 |
| 19.18 | 4.62 | 23 |
| 19.93 | 4.45 | 18 |
| 20.92 | 4.24 | 69 |
| 22.50 | 3.95 | 12 |
| 23.17 (shoulder) | 3.84 | 4 |
| 23.65 | 3.76 | 38 |
| 24.12 | 3.69 | 31 |
| 24.76 | 3.59 | 5 |
| 25.88 | 3.44 | 5 |
| 27.13 | 3.28 | 4 |
| 27.72 | 3.22 | 19 |
| 28.45-28.69 (broad) | 3.13-3.11 | 7-6 |
| 29.18 | 3.06 | 13 |
| 30.01-30.28 (broad) | 2.98-2.95 | 6-5 |
| 30.73 | 2.91 | 8 |
| 31.81 | 2.81 | 4 |
| 32.35-33.38 (broad) | 2.77-2.68 | 3-4 |
| 35.00 | 2.56 | 7 |
| 36.64 | 2.45 | 3 |
| 38.73 | 2.32 | 6 |
| 39.34 | 2.29 | 4 |

[a]I/Io = relative intensity

As used herein, "major XRPD peak" refers to an XRPD peak with a relative intensity greater than 20%. Relative intensity is calculated as a ratio of the peak intensity for the peak of interest versus the peak intensity for the largest peak.

Figure 2:
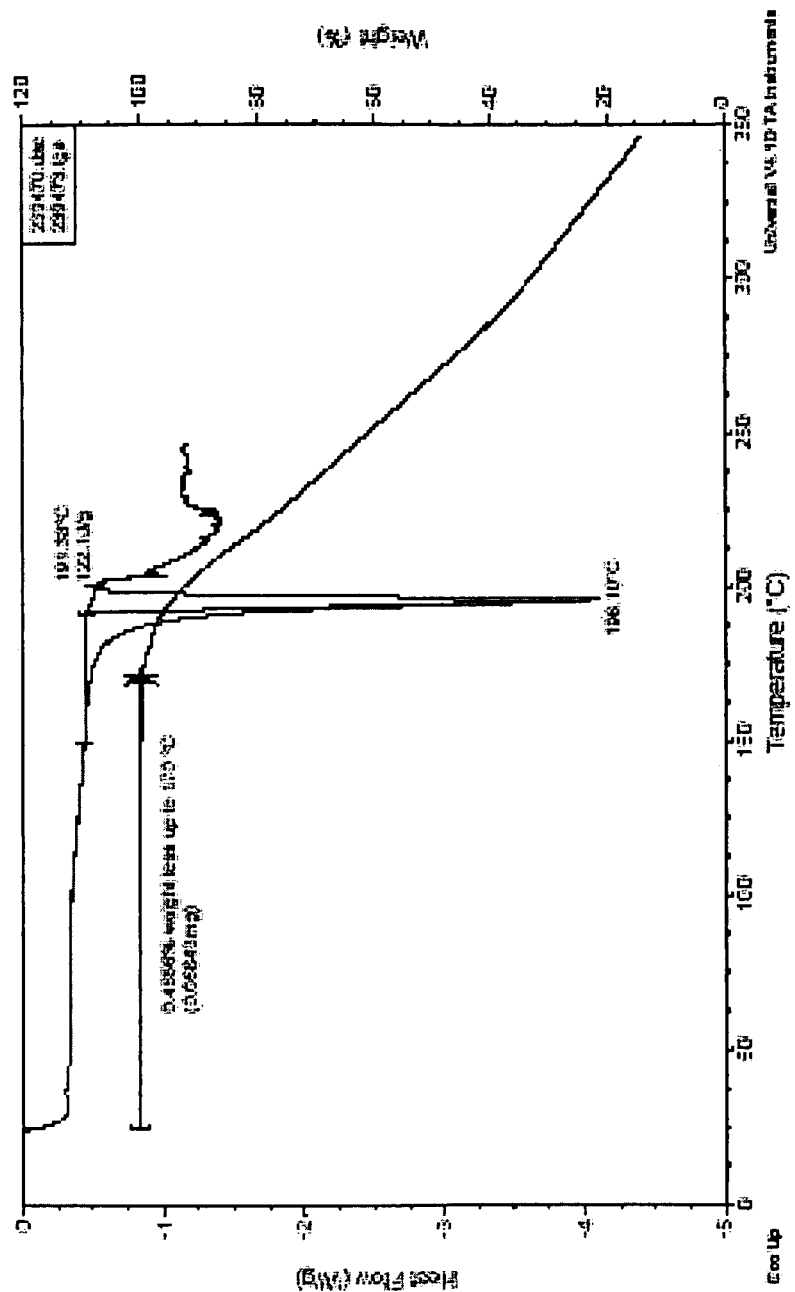
FIG. 2 is a graph showing thermal analysis data of a sample of Form A of compound 1: (A) differential scanning calorimetry profile, (B) thermal gravimetric profile.

In another embodiment of the invention, Form A of compound 1 is characterized by an endothermic transition with an onset at 191±1.0° C. and with a maximum at 196±1.0° C. in the differential scanning calorimetry (herein referred to as "DSC") profile shown in FIG. 2(A). The profile plots heat flow as a function of temperature from a sample containing Form A of compound 1. The DSC is performed on the sample using a scanning rate of 10° C./minute from 25 to 250° C.

Form A of compound 1 is also characterized by the thermal gravimetric analysis (herein referred to as "TGA") profile shown in FIG. 2(B). The profile graphs the percent loss of weight of the sample as a function of temperature with the temperature rate change being 10° C./minute from 25 to 250° C. The profile shows a weight loss of approximately 0.47% as the temperature of the sample is changed from 25° C. to 170° C.

Figure 3:
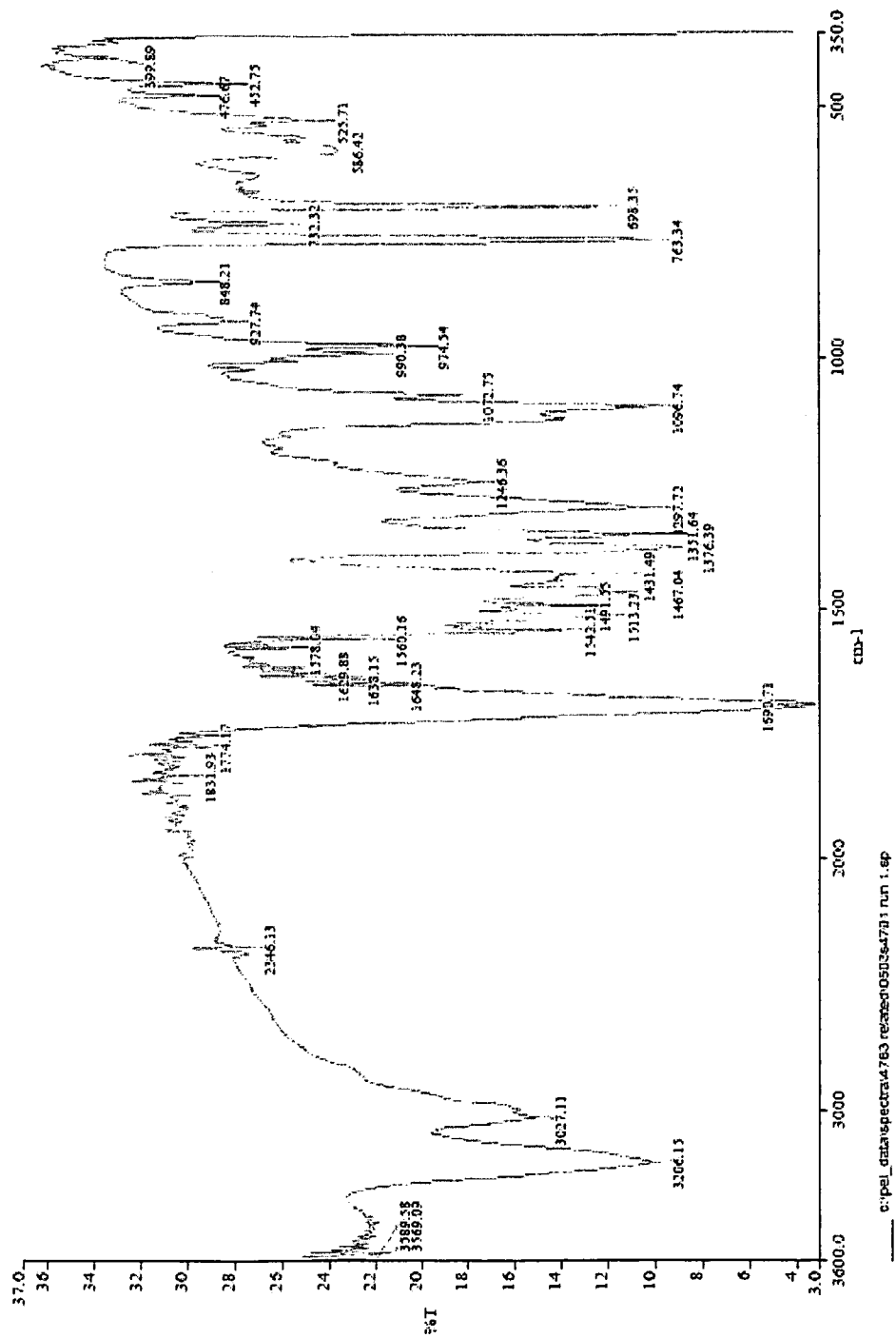
FIG. 3 is an IR (infra-red) spectrum of a sample of Form A of compound 1 in a KBr pellet.

Form A of compound 1 is also characterized by an IR spectrum shown in FIG. 3. More specifically, Form A of compound 1 has IR absorption peaks in a KBr matrix (e.g., a KBr pellet), for example, at 3206, 1691, 1376 and 1352 cm$^{-1}$. It is to be understood that a specific IR absorption peak means a specific value±1 cm$^{-1}$.

Figure 4:
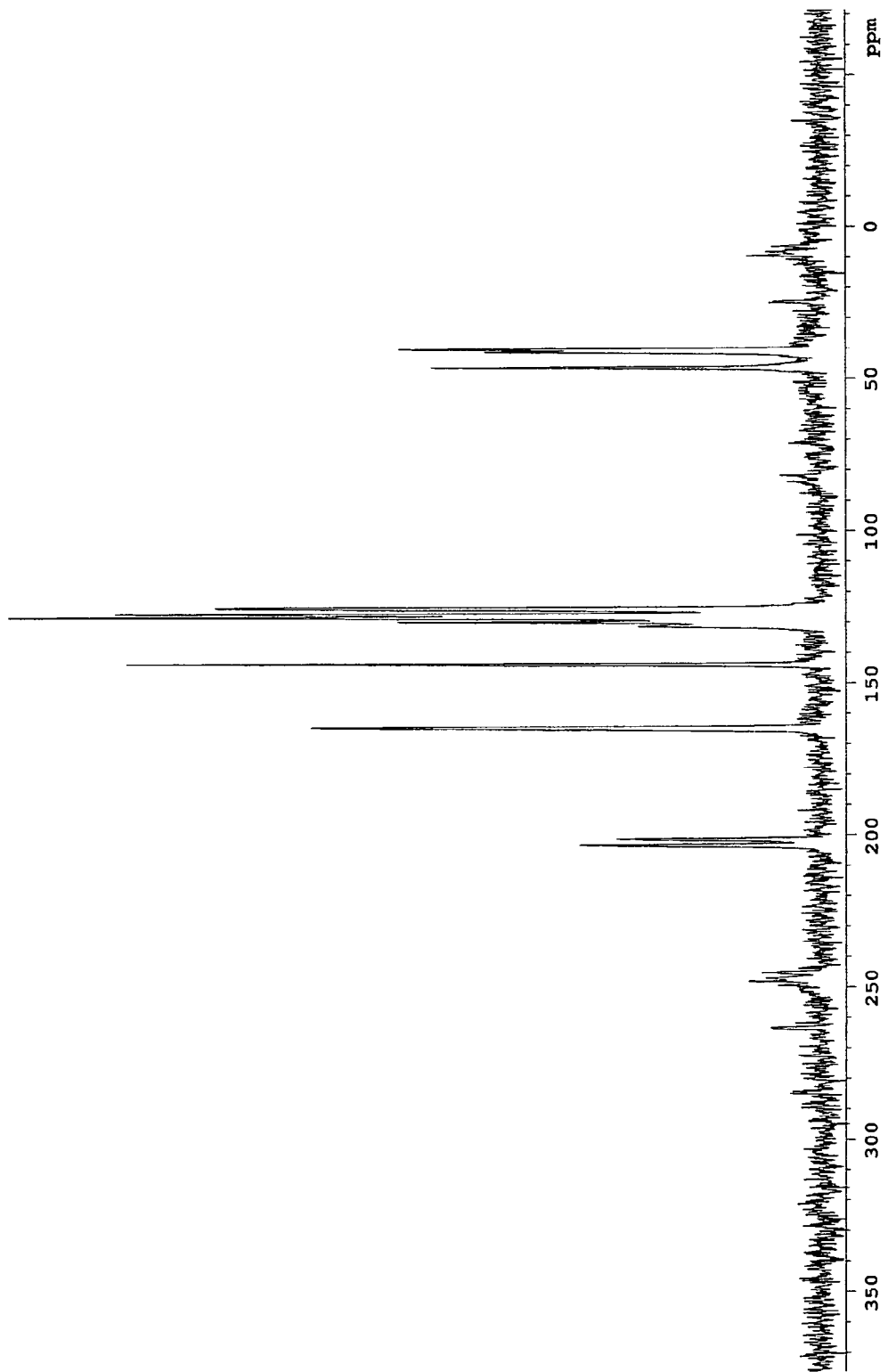
FIG. 4 is a solid state $^{13}$C-NMR (nuclear magnetic resonance) spectrum of a sample of Form A of compound 1.

Form A of compound 1 is also characterized by a solid state $^{13}$C-NMR spectrum shown in FIG. 4.

Form A of compound 1 is also characterized by a bulk density of 0.2-0.3 g/ml.

Form A of compound 1 is also characterized by a melting point of 189±1.0° C.-193±1.0° C. at a heating rate of 10° C./minute.

Figure 36:
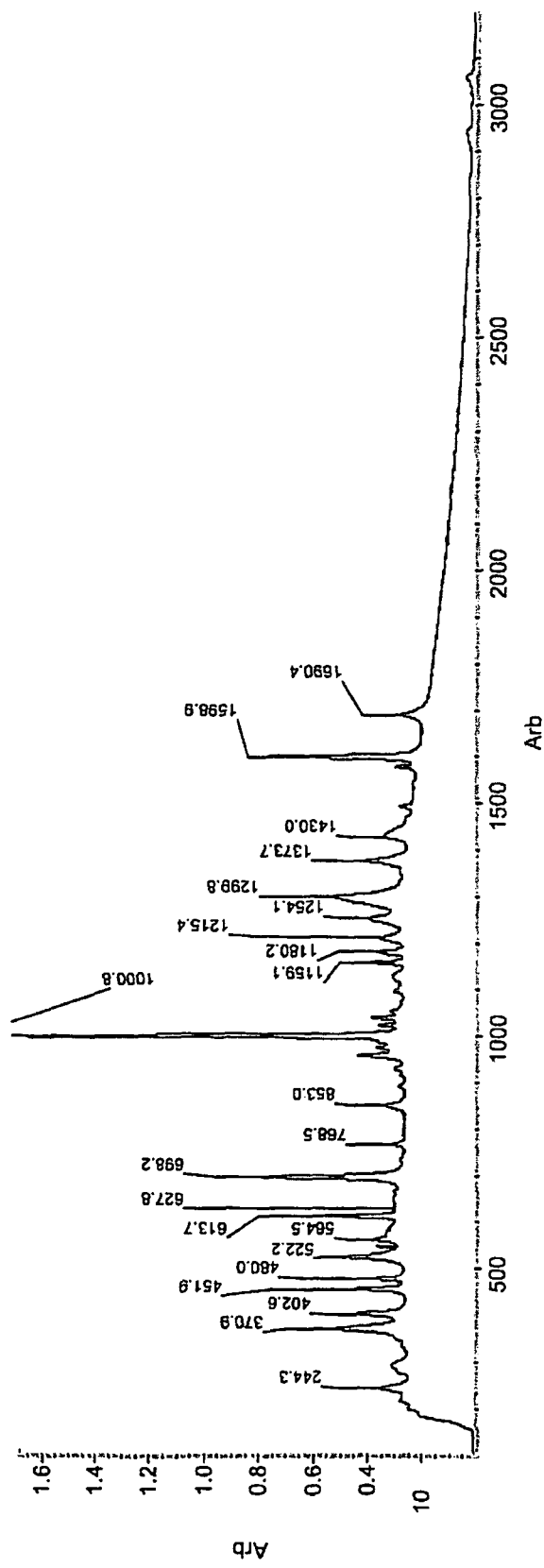
FIG. 36 is a Raman spectrum of a sample of Form A of compound 1.

Form A of compound 1 is also characterized by a Raman spectrum shown in FIG. 36. More specifically, Form A of compound 1 has Raman absorption peaks, for example, at 1374, 1001, 698 and 452 cm$^{-1}$. It is to be understood that a specific Raman absorption peak means a specific value±1 cm$^{-1}$.

Crystal Habit 1

In one embodiment, Form A of compound 1 is characterized by Crystal Habit 1. Crystal Habit 1 of Form A can generally be prepared from a saturated solution of Compound 1 in a variety of solvents, such as acetone, ethyl acetate, ethanol, tetrahydrofuran, dichloromethane, or an aqueous mixture thereof. Mixtures of ethyl acetate, ethanol, tetrahydrofuran, and dichloromethane with or without water can also be used. In one embodiment, Crystal Habit 1 is prepared by cooling a hot saturated acetone-water solution of compound 1 from a temperature greater than 50° C., generally between 50° C. and 70° C. (e.g., 60° C.), to ambient temperature. Typically, the water to acetone ratio of the hot acetone-water solution of compound 1 is equal to or greater than 1:1 by volume. Typically, the amount of each of the acetone and the water employed independently is greater than 12 L per 1 kg of Compound 1. In one example, the amount of the acetone and the water employed are each independently greater than 14 L per 1 kg of Compound 1, such as 25 L per 1 kg of Compound 1.

The hot acetone-water solution of compound 1 is then allowed to cool to ambient temperature, and the resulting mixture is stirred for a time period to allow Crystal Habit 1 of Form A to precipitate. Although the time period for the stirring is typically over 1 day (e.g., over 2 days or 3 days), it is noted that the time period can easily be determined by assessing its characteristic properties, for example, IR or NMR, of a portion of the precipitate from the resulting mixture. In one example, the time period for the stirring is between 3-4 days. As used herein, "ambient temperature" means room temperature and typically between 18° C.-25° C. (e.g. 18° C.-23° C.).

In one specific embodiment, Crystal Habit 1 of Form A is characterized by an elongated shape, such as a needle-or rod-like shape. In another specific embodiment, the needle-or rod-like shape has an average crystal size (the principal or longest dimension) of less than 50 microns, typically less than 20 microns. In yet another specific embodiment, Crystal Habit 1 is an agglomerate of needle- or rod-like crystals having an average size of less than 50 microns, wherein the agglomerate has a particle size distribution (PSD) with a D90 of between 100 microns and 600 microns, or between 100 and 500 microns. In yet another specific embodiment, Crystal Habit 1 is an agglomerate of needle-or rod-like crystals having an average size of less than 50 microns, wherein the agglomerate has a particle size distribution (PSD) with a D90 of between 60 and 100 microns. In yet another specific embodiment, screen-passing at least 50% by weight of Crystal Habit 1, requires a screen of greater than 150 micron. In one example, screen-passing at least 70% by weight of Crystal Habit 1, requires a screen of greater than 150 microns. In another example, screen-passing at least 80% by weight of Crystal Habit 1, requires a screen of greater than 150 microns. In yet another example, screen-passing at least 90% by weight of Crystal Habit 1, requires a screen of greater than 150 microns. In one embodiment, less than 50% by weight of Crystal Habit 1 passes through a 150 micron screen. In another embodiment, less than 40% by weight of Crystal Habit 1 passes through a 150 micron screen. In another embodiment, less than 30% by weight of Crystal Habit 1 passes through a 150 micron screen. In another embodiment, less than 20% by weight of Crystal Habit 1 passes through a 150 micron screen. In another embodiment, less than 10% by weight of Crystal Habit I passes through a 150 micron screen. In one embodiment, the reconstitution time for Crystal Habit 1 that has passed through a 500 micron screen is greater than 25 minutes.

As used herein, the reconstitution time is measured in 50:50 Cremophor EL/ethanol solution at ambient temperature (e.g., 18-25° C.) The reconstitution time can be measure according to the procedure described in Example 7. For example, the reconstitution time is measured by dissolving 266 mg of compound 1 in 16.7 mL of 50:50 Cremophor EL/ethanol solution with manual shaking or mechanical shaking at a speed of 232-236 rpm.

In another embodiment, Crystal Habit 1 of Form A has a length to width aspect ratio that is greater than or equal to about 4 to less than or equal to about 13 (i.e. ~4≤aspect ratio ≤~13). In another embodiment, the length to width aspect ratio is greater than or equal to about 5 to less than or equal to about 10 (i.e. ~5≤aspect ratio≤~10).

Crystal Habit 2

In another embodiment, Form A of compound 1 is characterized by Crystal Habit 2. Crystal Habit 2 of Form A can generally be prepared from a saturated solution of compound 1 in a variety of solvents, such as acetone, ethyl acetate, ethanol, tetrahydrofuran, dichloromethane, DMF or an aqueous mixture thereof Mixtures of acetone, ethyl acetate, ethanol, tetrahydrofuran, DMF and dichloromethane with or without water can also be used. For example, a mixture of ethanol, DMF and water can be used. In one embodiment, Crystal Habit 2 is prepared from a saturated solution of compound 1 in acetone and water. Typically acetone is major by volume. In one example, the acetone: water ratio is greater than 5:1 by volume. In another example, the acetone: water ratio is 7:1 by volume. In another embodiment, Crystal Habit 2 is prepared from a saturated acetone solution of compound 1. Typically, the amount of the acetone employed is greater than 12 L acetone per 1 kg of compound 1. In one example, the amount of the acetone employed is greater than 14 L acetone per 1 kg of compound 1, such as 28 L per 1 kg of compound 1.

The acetone-water solution or the acetone solution, of compound 1 is then added to cold water to cause at least a portion of compound 1 to precipitate. Typically, the temperature of the water to which the solution of compound 1 is added is lower than or equal to 10° C. (e.g., 10° C. or 0° C.-5° C.). In one example, the temperature of the water to which th solution of compound 1 is added is lower than or equal to 5° C. (e.g., 0° C.). During the addition, the temperature of the resulting mixture is maintained at a temperature lower than or equal to 10° C. (e.g., at a temperature lower than or equal to 5° C.). In one specific embodiment, after the completion of the addition of the solution of compound 1 to the cold water, the resulting suspension is then allowed to warmed up to ambient temperature, and stirred for a time period at ambient temperature.

Typically, the amount of the cold water to which the solution of compound 1 is added, is greater than 1.8:1 water to acetone, by volume, generally greater than or equal to 2:1 by volume.

Typically, the addition of the solution of compound 1 to the cold water is performed for a time period of greater than 10 minutes, generally greater than 20 minutes. In one example, the addition of the solution of compound 1 to the cold water is performed between 20 minutes and 40 minutes.

Typically, the suspension resulting from the solution of compound 1 and the cold water is stirred at ambient temperature for more than 1 hour, or more than 3 hours. In one example, the time period is 3-12 hours or 6-12 hours. In another example, the time period is 20-24 hours.

In one specific embodiment, Crystal Habit 2 of Form A is characterized as agglomerates of multiply nucleated radial aggregates (spherulites). In another specific embodiment, crystals of Crystal Habit 2, have an average crystal size (the principal or longest dimension) of less than 50 microns (e.g., less than 20 microns). In another specific embodiment, Crystal Habit 2 is an agglomerate of fine crystals having an average crystal size of less than 50 microns, wherein the agglomerate has a particle size distribution (PSD) with a D90 of between 100 and 150 microns. In yet another specific embodiment, Crystal Habit 2 is an agglomerate of fine crystals having an average crystal size of less than 50 microns, wherein the agglomerate has a mono-modal particle size distribution (PSD) with a D50 of between 60 and 100 microns. In yet another specific embodiment, at least 50% by weight of Crystal Habit 2, passes through a 150 micron screen. In one example, at least 70% by weight, of Crystal Habit 2 passes through a 150 micron screen. In another example, at least 80% by weight of Crystal Habit 2, passes through a 150 micron screen. In another example, at least 90% by weight of Crystal Habit 2, passes through a 150 micron screen. In another example, at least 95% by weight of Crystal Habit 2 passes through a 150 micron screen. In general, Crystal Habit 2 is less cohesive, less compressible and more permeable than Crystal Habit 1, and, therefore, has satisfactory powder flow properties for dry powder fill. With Crystal Habit 2, reconstitution times less than or equal to approximately 15 minutes at ambient temperature can be achieved. In one example, the reconstitution time in 50:50 Cremophor EL/ethanol for Crystal Habit 2 that has passed through a 150 micron screen is less than or equal to about 15 minutes, for example, less than about 10 minutes or less than about 5 minutes. In one embodiment, at least 70%, 80%, 90% or 95% by weight of Crystal Habit 2 passes through a 150 micron screen and has a reconstitution time of less than 15 minutes in 50:50 Cremophor EL/ethanol.

In another embodiment, the Crystal Habit 2 of Form A (agglomerates of multiply nucleated radial aggregates (spherulites)) has a length to width aspect ratio that is greater than or equal to about 1 and less than or equal to about 2 (i.e. ~1≤aspect ratio≤~2). In another embodiment, the length to width aspect ratio is about 1.2.

In another embodiment, at least 70%, 80%, 90% or 95% by weight of Crystal Habit 2 passes through a 150 micron screen and has a length to width aspect ratio of greater than or equal to about 1 and less than or equal to about 2. In another embodiment, at least 70%, 80%, 90% or 95% by weight of Crystal Habit 2 has a reconstitution time of less than 15 minutes in 50:50 Cremophor EL/ethanol and a length to width aspect ratio of greater than or equal to about 1 and less than or equal to about 2. In another embodiment, at least 70%, 80%, 90% or 95% by weight of Crystal Habit 2 passes through a 150 micron screen and has a reconstitution time of less than 15 minutes in 50:50 Cremophor EL/ethanol and a length to width aspect ratio of greater than or equal to about 1 and less than or equal to about 2.

Form C

In one embodiment of the invention, a single crystalline form of compound 1 is characterized as Form C. This crystalline form is also characterized by the XRPD pattern shown in FIG. 5 with values of 2θ angles, d-spacing and relative intensities as listed in Table 2, obtained using Cu—Kα radiation. In a specific embodiment, the crystalline form Form C of compound 1 is characterized by one, two, three, four or five major XRPD peaks at 2θ angle selected from the group consisting of 10.32°, 14.80°, 21.49°, 23.05° and 30.12°. In another specific embodiment, the crystalline form Form C of compound 1 is characterized by major XRPD peaks at 2θ angles of 8.64°, 10.32°, 14.80°, 15.70°, 16.88°, 19.15°, 19.68°, 21.49°, 23.05°, 24.34° and 30.12°.

TABLE 2

Figure 5:
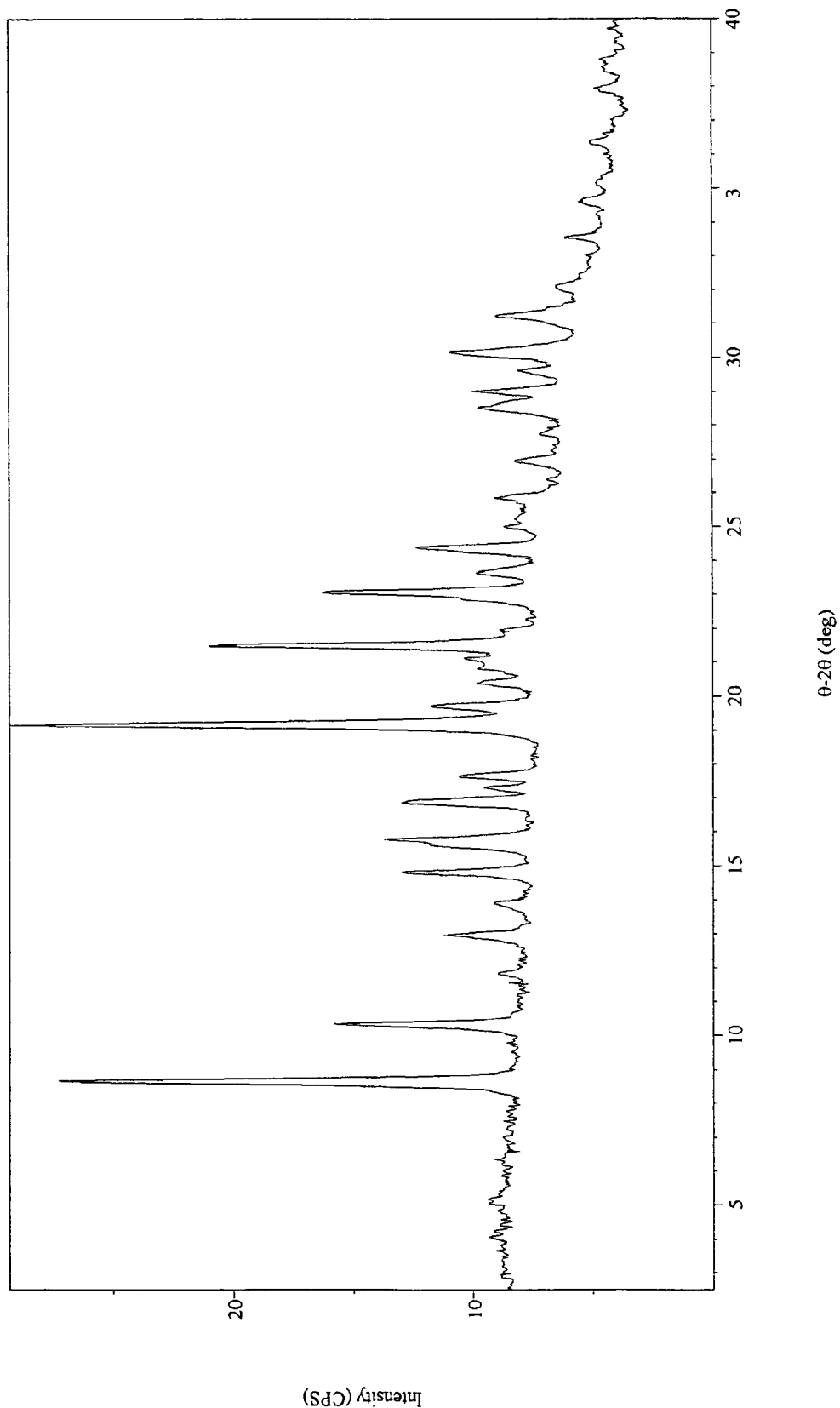
FIG. 5 is an XRPD pattern obtained from a sample of Form C of compound 1.

XRPD Peaks for FIG. 5

| Position (°2θ) | d-spacing (Å) | I/Io[a] |
|---|---|---|
| 5.12 | 17.24 | 4 |
| 8.64 | 10.22 | 86 |
| 10.32 | 8.56 | 34 |
| 11.83 | 7.48 | 5 |
| 12.94 | 6.83 | 14 |
| 13.86 | 6.38 | 6 |
| 14.80 | 5.98 | 24 |
| 15.70 | 5.64 | 26 |
| 16.88 | 5.25 | 26 |
| 17.29 | 5.13 | 9 |
| 17.64 | 5.02 | 15 |
| 19.15 | 4.63 | 100 |
| 19.68 | 4.51 | 21 |
| 20.39 | 4.35 | 11 |
| 20.86-21.07 (broad) | 4.26-4.21 | 11-13 |
| 21.49 | 4.13 | 64 |
| 21.91 (shoulder) | 4.05 | 7 |
| 22.75 | 3.91 | 8 |
| 23.05 | 3.86 | 43 |
| 23.64 | 3.76 | 12 |
| 24.34 | 3.65 | 24 |
| 25.00-25.81 (broad) | 3.56-3.45 | 7-10 |
| 26.93 | 3.31 | 8 |
| 27.75 | 3.21 | 4 |
| 28.48-28.66 (broad) | 3.13-3.11 | 16-12 |
| 28.98 | 3.08 | 17 |
| 29.57 | 3.02 | 10 |
| 30.12 | 2.96 | 24 |
| 31.22 | 2.86 | 17 |
| 32.06 | 2.79 | 6 |
| 33.53 | 2.67 | 6 |
| 34.60 | 2.59 | 5 |
| 36.33 | 2.47 | 6 |
| 37.90 | 2.37 | 6 |
| 38.44-38.80 (broad) | 2.34-2.32 | 4 |

[a]I/Io = relative intensity

Figure 6:
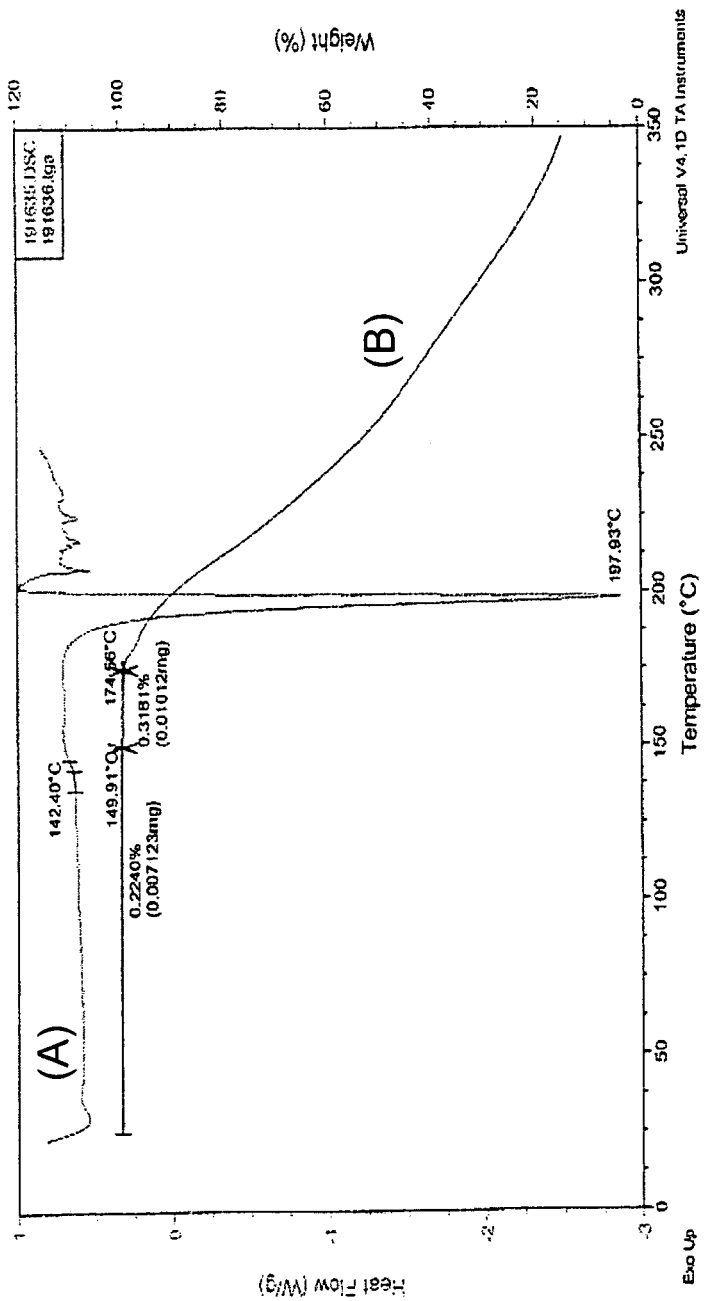
FIG. 6 is a graph showing thermal analysis data of a sample of Form C of compound 1: (A) differential scanning calorimetry profile, (B) thermal gravimetric profile.

In another embodiment of the invention, Form C of compound 1 is characterized by an exothermic transition at 142±1.0° C. and by an endothermic transition at 197±1.0° C. in the differential scanning calorimetry (herein referred to as "DSC") profile shown in FIG. 6(A). The profile plots heat flow as a function of temperature from a sample containing Form C of compound 1. The DSC is performed on the sample using a scanning rate of 10° C./minute from 25 to 250° C.

Form C of compound 1 is also characterized by the thermal gravimetric analysis (herein referred to as "TGA") profile shown in FIG. 6(B). The profile graphs the percent loss of weight of the sample as a function of temperature with the temperature rate change being 10° C./minute from 25 to 250° C. The profile shows a weight loss of approximately 0.318% as the temperature of the sample is changed from 25° C. to 175° C.

In a specific embodiment, Form C of compound 1 undergoes an exothermic transition at 142±1.0° C.-150±1.0° C. and followed by melting at 190±1.0° C.-192±1.0° C., at a heating rate of 10° C./minute.

Form C can generally be prepared from a saturated solution of compound 1 in a variety of solvents, such as acetone, ethyl acetate, ethanol, tetrahydrofuran, dichloromethane, or an aqueous mixture thereof. Mixtures of acetone, ethyl acetate, ethanol, tetrahydrofuran, and dichloromethane with or without water can also be used. In one embodiment, Form C of compound 1 is prepared by slow cooling a saturated solution of compound 1 in dichloromethane.

Form D

In one embodiment of the invention, a single crystalline form of compound 1 is characterized as Form D. This crystalline form is also characterized by the XRPD pattern shown in FIG. 7 with values of 2θ angles, d-spacing and relative intensities as listed in Table 3, obtained using Cu—Kα radiation. In a specific embodiment, the crystalline form Form D of compound 1 is characterized by one, two, three, four, five, six, seven, eight, nine, ten or eleven major XRPD peaks at 2θ angle selected from the group consisting of 7.52°, 13.22°, 13.90°, 17.23°, 22.06°, 22.66°, 23.35°, 24.97°, 26.65°, 28.44° and 29.19°. In another specific embodiment, the crystalline form Form D of compound 1 is characterized by major XRPD peaks at 2θ angles of 7.52°, 7.84°, 13.22°, 13.90°, 15.82°, 16.75°, 17.23°, 18.70°, 19.71°, 20.80°, 22.06°, 22.66°, 23.35°, 23.74°, 24.07°, 24.31°, 24.97°, 26.65°, 28.44° and 29.19°.

TABLE 3

Figure 7:
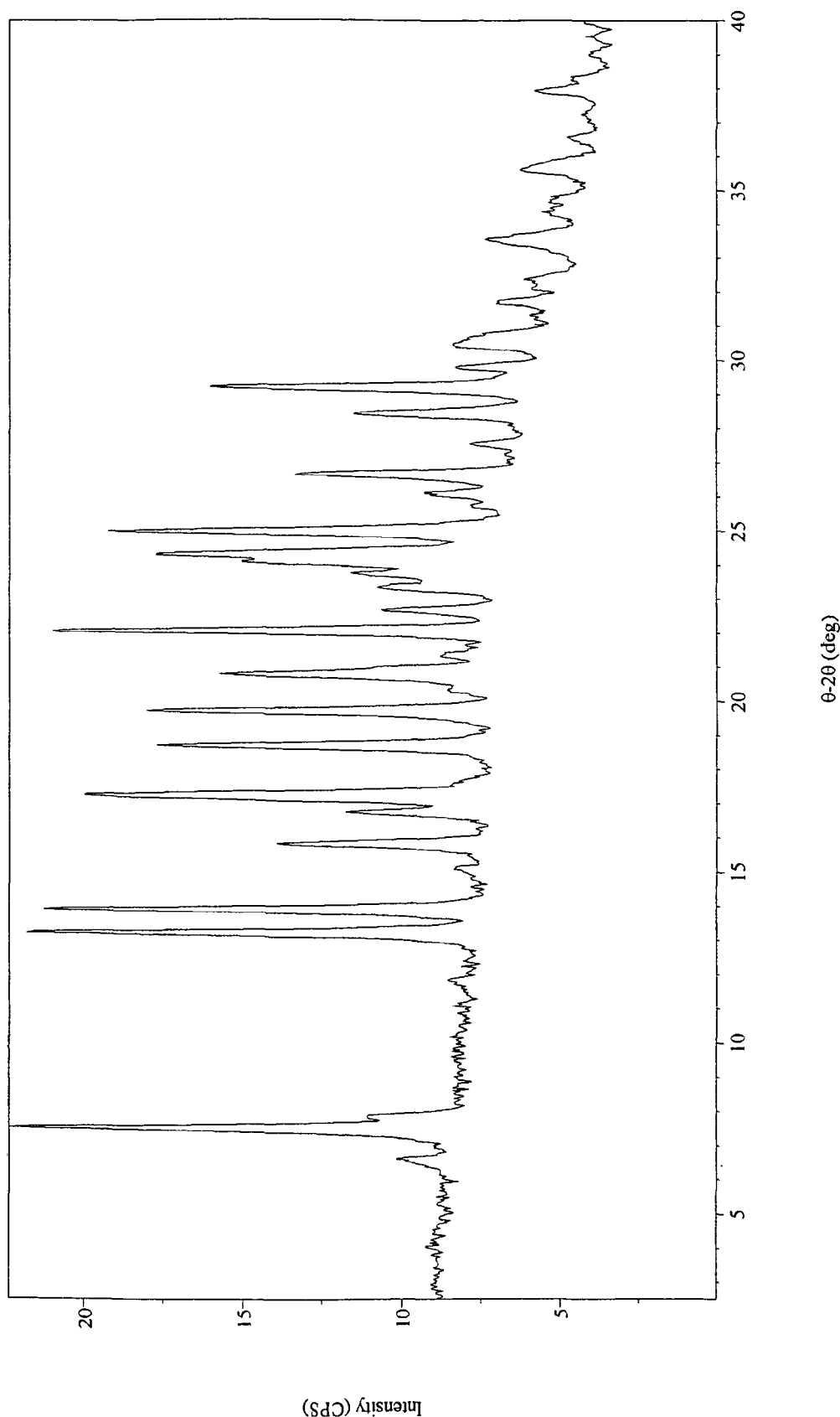
FIG. 7 is an XRPD pattern obtained from a sample of Form D of compound 1.

XRPD Peaks for FIG. 7

| Position (°2θ) | d-spacing (Å) | I/Io[a] |
|---|---|---|
| 6.55 | 13.49 | 12 |
| 7.52 | 11.75 | 96 |
| 7.84 | 11.27 | 21 |
| 11.79 | 7.50 | 5 |
| 13.22 | 6.69 | 97 |
| 13.90 | 6.36 | 96 |
| 15.07 | 5.87 | 6 |
| 15.82 | 5.60 | 46 |
| 16.75 | 5.29 | 30 |
| 17.23 | 5.14 | 93 |
| 18.70 | 4.74 | 73 |
| 19.71 | 4.50 | 77 |
| 20.35 | 4.36 | 8 |
| 20.80 | 4.27 | 60 |
| 21.35 | 4.16 | 10 |
| 22.06 | 4.03 | 100 |
| 22.66 | 3.92 | 23 |
| 23.35 | 3.81 | 25 |
| 23.74 | 3.75 | 31 |
| 24.07 | 3.69 | 55 |
| 24.31 | 3.66 | 78 |
| 24.97 | 3.56 | 88 |
| 25.30 | 3.52 | 6 |
| 25.75 | 3.46 | 6 |
| 26.09 | 3.41 | 17 |
| 26.65 | 3.34 | 50 |
| 27.54 | 3.24 | 10 |
| 28.44 | 3.14 | 40 |
| 29.19 | 3.06 | 76 |
| 29.79 | 3.00 | 19 |
| 30.46-30.76 | 2.93-2.90 | 21-15 |
| 31.32 | 2.85 | 4 |
| 31.71 | 2.82 | 14 |
| 32.11-32.38 | 2.79-2.76 | 6-8 |
| 33.53 | 2.67 | 20 |
| 34.33-34.72 (broad) | 2.61-2.58 | 8-7 |
| 35.67 | 2.51 | 17 |
| 36.52 | 2.46 | 6 |

TABLE 3-continued

XRPD Peaks for FIG. 7

| Position (°2θ) | d-spacing (Å) | I/Io[a] |
|---|---|---|
| 37.20 | 2.42 | 3 |
| 37.92 | 2.37 | 17 |
| 38.29 | 2.35 | 8 |
| 39.00 | 2.31 | 4 |
| 39.50 | 2.28 | 4 |

[a]I/Io = relative intensity

Figure 8:
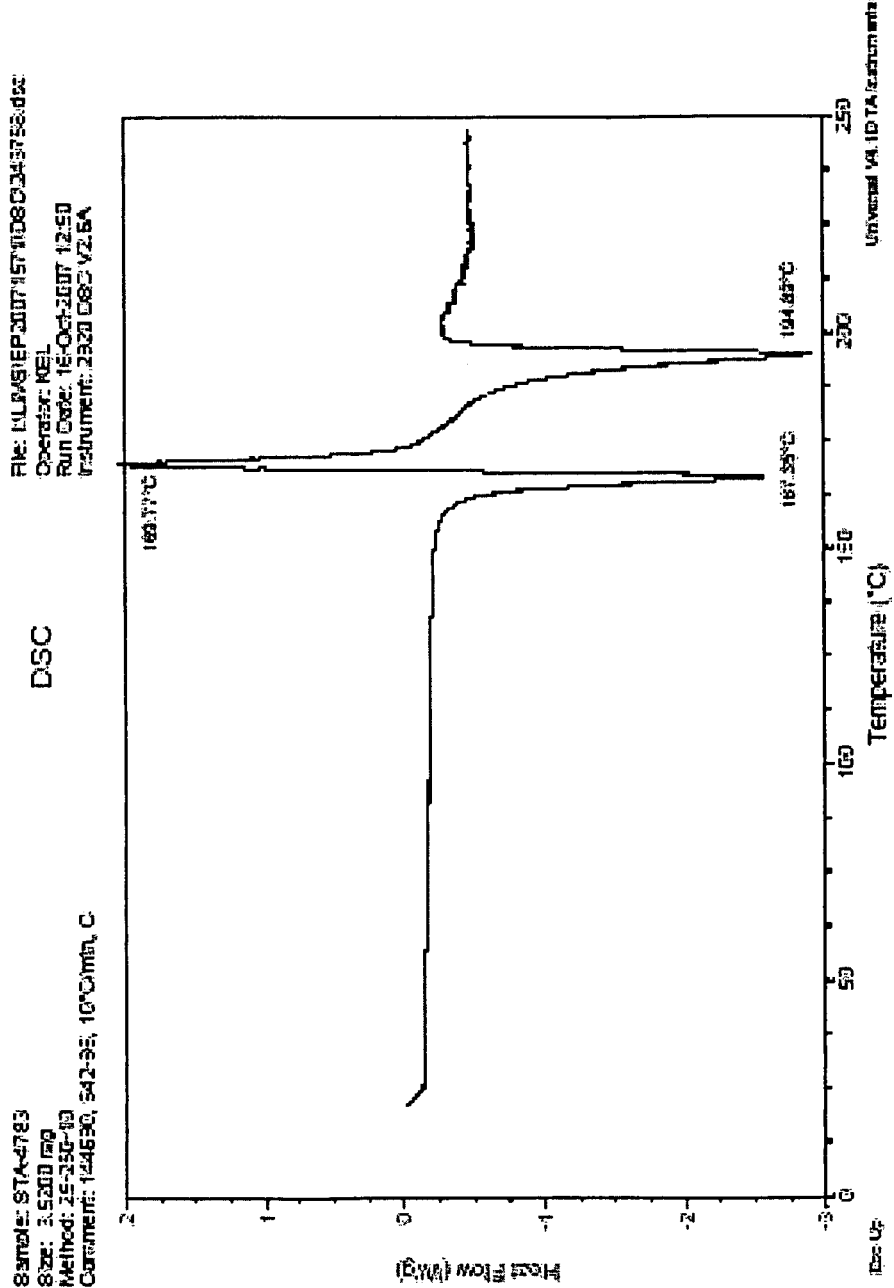
FIG. 8 is a graph showing differential scanning calorimetry data of a sample of Form D of compound 1.
Figure 9:
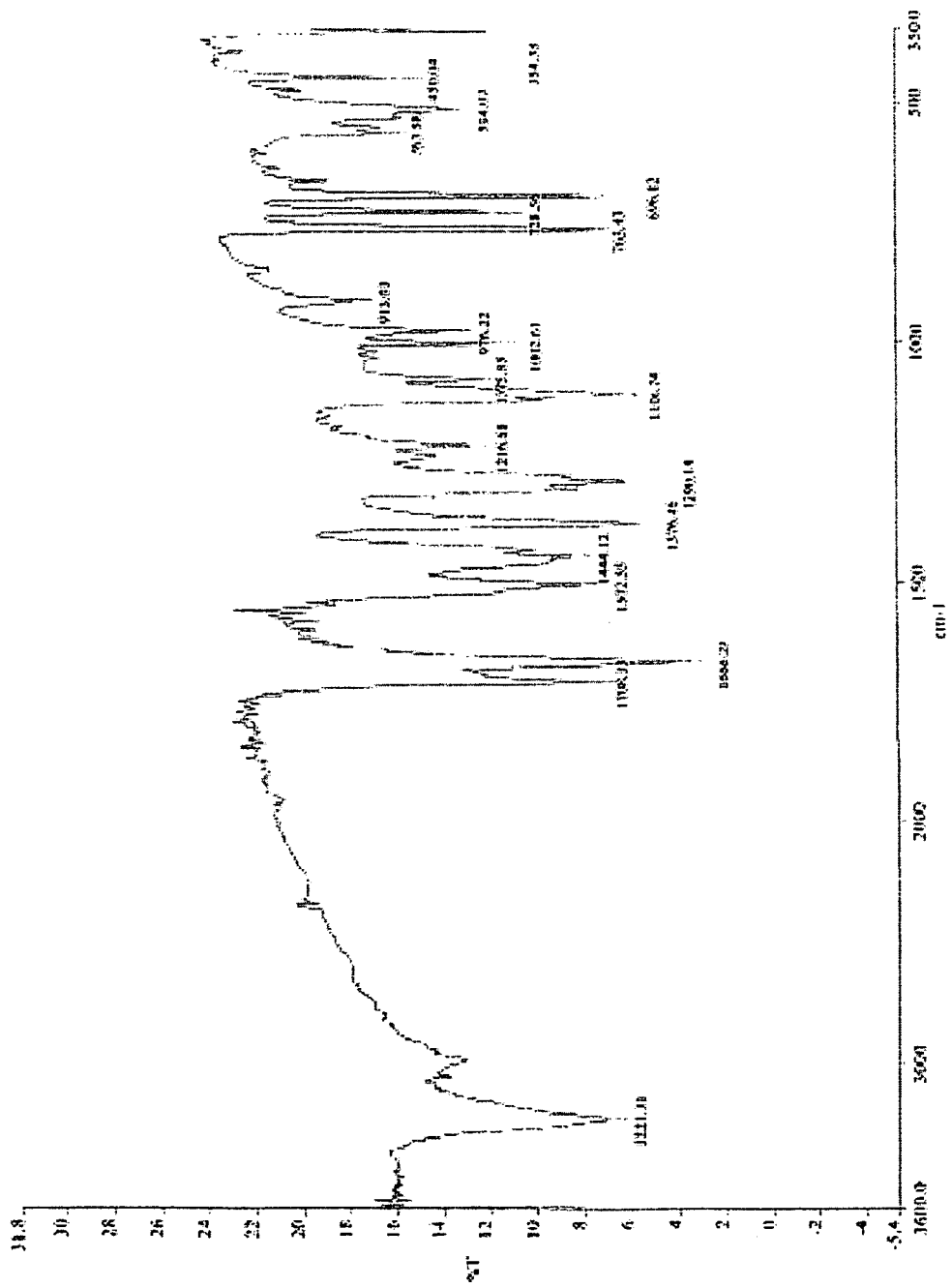
FIG. 9 is an IR spectrum of a sample of Form D of compound 1 in a KBr pellet.
Figure 10:
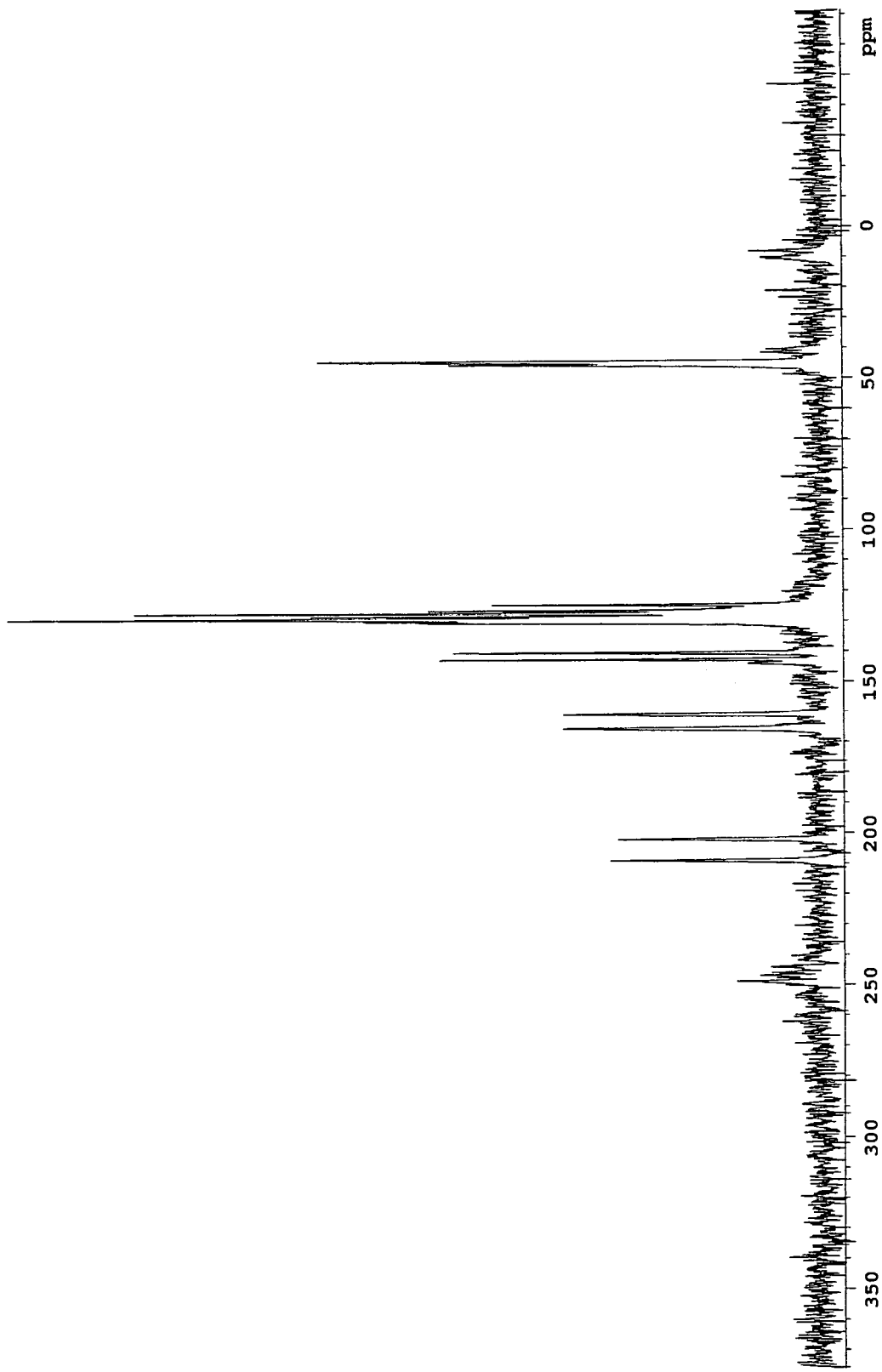
FIG. 10 is a solid state $^{13}$C-NMR spectrum of a sample of Form D of compound 1.

In another embodiment of the invention, Form D of compound 1 is characterized by a DSC profile shown in FIG. 8. The DSC profile shows an endothermic transition with a maximum at 167±1.0° C., leading to an exothermic transition with maximum at 170±1.0° C., followed by an endothermic transition with a maximum at 195±1.0° C. The profile plots heat flow as a function of temperature from a sample containing Form D of compound 1. The DSC is performed on the sample using a scanning rate of 10° C./minute from 25 to 250° C. Form D of compound 1 is also characterized by an IR spectrum shown in FIG. 9. For example, Form D of compound 1 has IR absorption peaks in a KBr matrix (e.g., a KBr pellet), for example, at 3221, 1708, 1666 and 1376 $cm^{-1}$.

Figure 37:
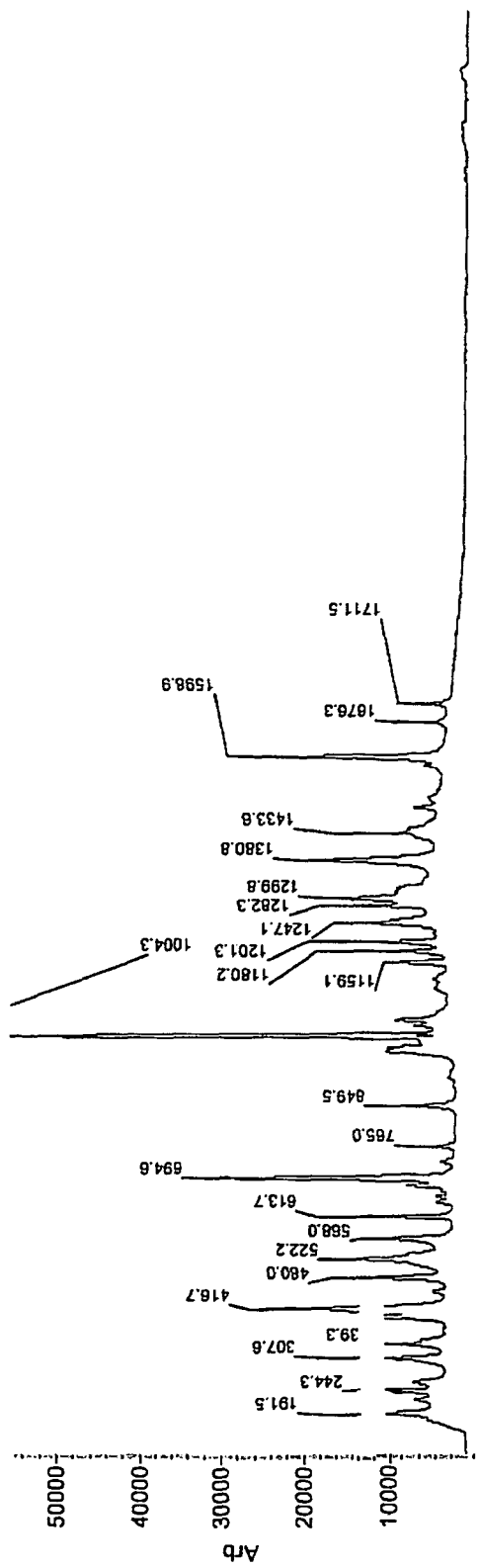
FIG. 37 is a Raman spectrum of a sample of Form D of compound 1.

Form D of compound 1 is also characterized by a Raman spectrum shown in FIG. 37. For example, Form D of compound 1 has Raman absorption peaks, for example, at 1381, 1004 and 695 $cm^{-1}$.

In another embodiment of the invention, Form D of compound 1 is characterized by a single crystal structure. The single crystal structure is derived from X-ray crystallographic data obtained from suitable single crystals of Form D of compound 1 using Mo Kα radiation. The crystal structure is characterized as a P1 21/n1 space group having the following unit cell parameters:

$a$=14.4±0.1 Å; $b$=5.7±0.1 Å; $c$=23.9±0.1 Å;
β=102.1±0.1°; and $V$=1920±1 $Å^3$.

In one specific embodiment, Form D of compound 1 is characterized by the single crystal structure as a P1 21/n1 space group having the following unit cell parameters:

$a$=14.3994(8) Å; $b$=5.7133(3) Å; $c$=23.872(3) Å;
β=102.130(3)°; and $V$=1920.1(2) $Å^3$.

In a further specific embodiment, Form D of compound 1 is characterized by the single crystal structure as a P1 21/n1 space group having the unit cell parameters of Table 4 below.

TABLE 4

Crystal Data and Data Collection Parameters of Form D of Compound 1

| formula | $C_{19}H_{20}N_4O_2S_2$ |
|---|---|
| formula weight | 400.52 |
| space group | P 1 21/n 1 (No. 14) |
| a, Å | 14.3994(8) |
| b, Å | 5.7133(3) |
| c, Å | 23.872(3) |
| b, deg | 102.130(3) |
| V, $Å^3$ | 1920.1(2) |
| Z | 4 |
| $d_{calc}$, g $cm^{-3}$ | 1.385 |
| crystal dimensions, mm | 0.44 × 0.23 × 0.15 |
| temperature, K | 150. |
| radiation (wavelength, Å) | Mo $K_α$ (0.71073) |
| monochromator | graphite |
| linear abs coef, $mm^{-1}$ | 0.286 |
| absorption correction applied | empirical[a] |
| transmission factors: min, max | 0.88, 0.96 |

TABLE 4-continued

Crystal Data and Data Collection Parameters of Form D of Compound 1

| diffractometer | Nonius KappaCCD |
|---|---|
| h, k, l range | 0 to 18 0 to 7 −30 to 30 |
| 2q range, deg | 4.98-54.94 |
| mosaicity, deg | 0.36 |
| programs used | SHELXTL |
| $F_{000}$ | 840.0 |
| weighting | $1/[s^2(F_o^2) + (0.0948P)^2 + 0.0000P]$ where P = $(F_o^2 + 2F_o^2)3$ |
| data collected | 26218 |
| unique data | 4333 |
| $R_{int}$ | 0.071 |
| data used in refinement | 4333 |
| cutoff used in R-factor calculations | $F_o^2 > 2.0 s(F_o^2)$ |
| data with I >2.0 s(I) | 2776 |
| number of variables | 254 |
| largest shift/esd in final cycle | 0.00 |
| $R(F_o)$ | 0.052 |
| $R_w(F_o^2)$ | 0.130 |
| goodness of fit | 0.957 |

[a]Otwinowski Z. & Minor, W. *Methods Enzymol.*, 1997. 276, 307.

Figure 11A:
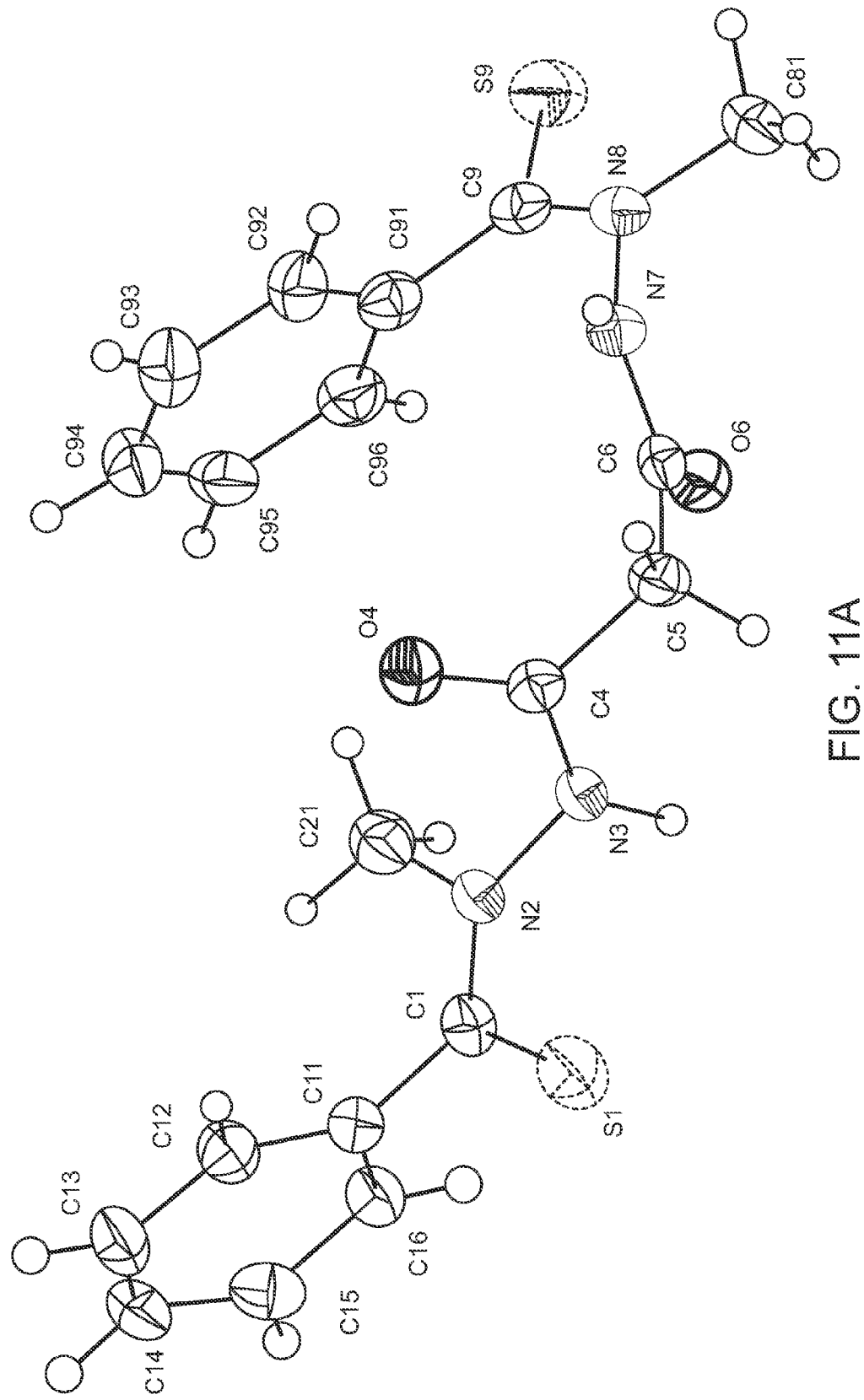
FIG. 11(A) is an ORTEP drawing of the X-ray structure of Form D of compound 1 where atoms are represented by 50% probability anisotropic thermal ellipsoids.
Figure 11B:
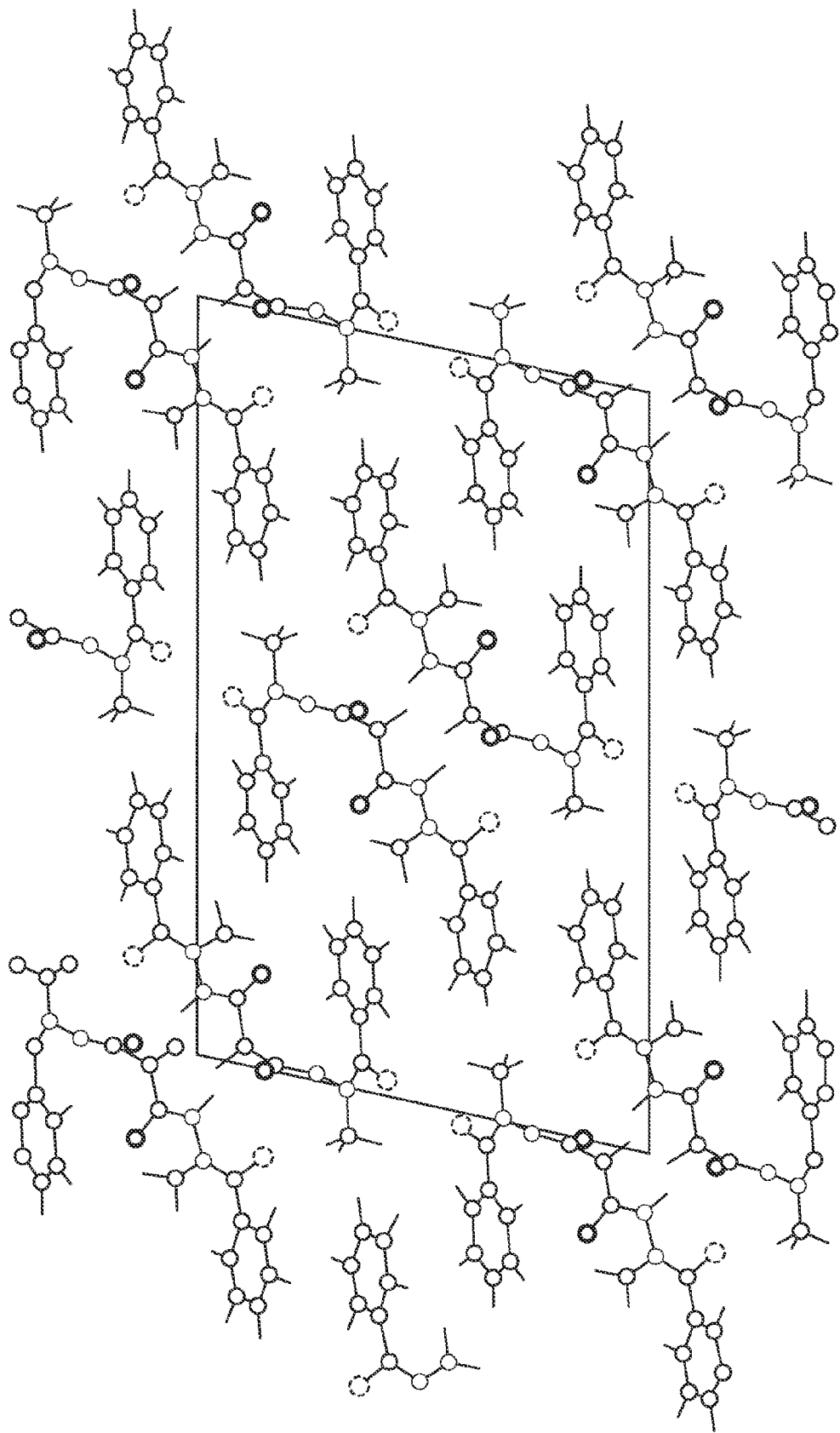
FIG. 11(B) is a packing diagram of compound 1 shown in FIG. 11(A), which is viewed down the crystallographic b axis.
Figure 11C:
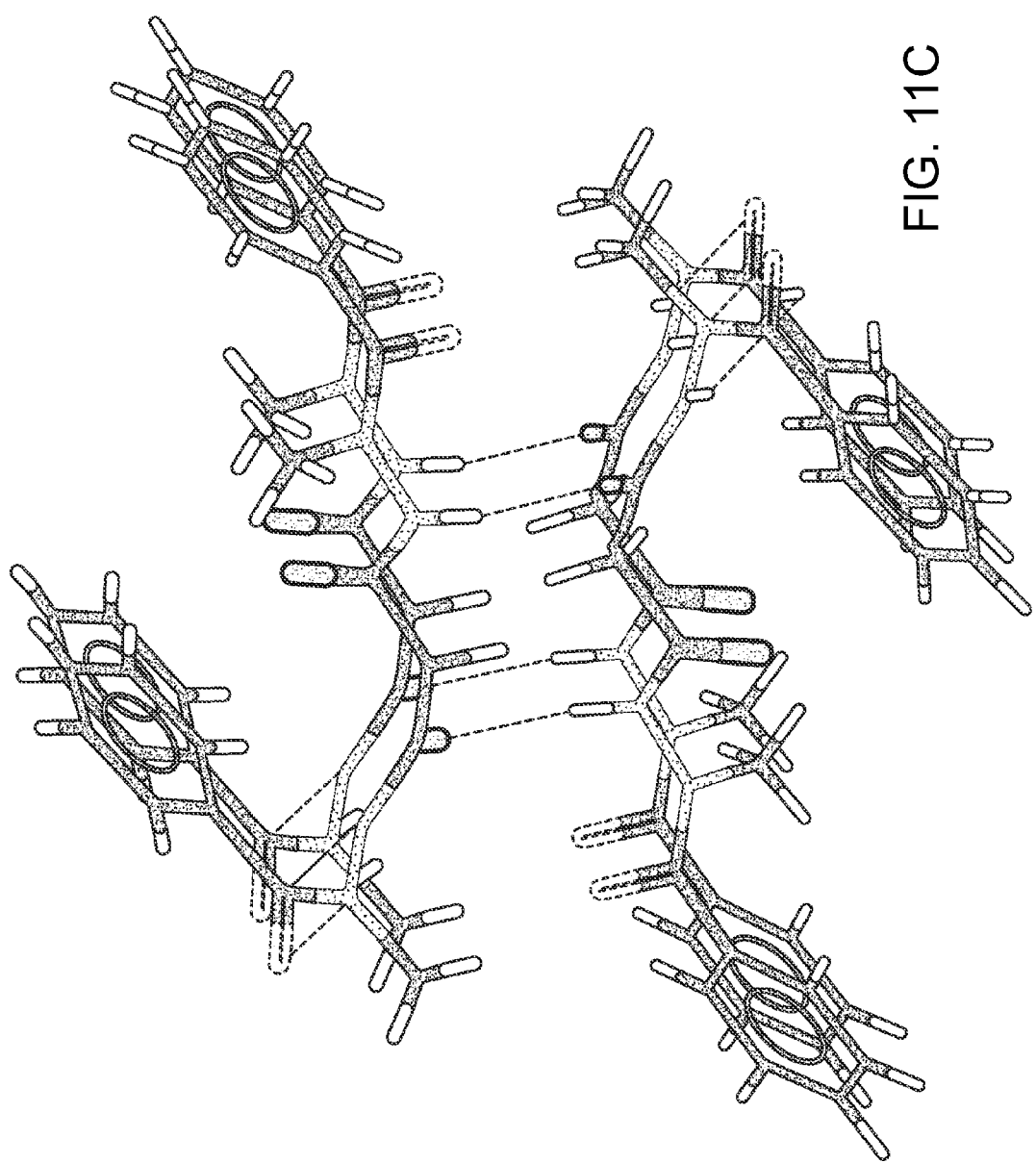
FIG. 11(C) shows a hydrogen bonding scheme of compound 1 shown in FIG. 11(B).

FIG. 11(A) shows an ORTEP drawing of the single crystal structure of Form D of compound 1, where atoms are represented by 50% probability anisotropic thermal ellipsoids. In a specific embodiment, Form D of compound 1 is characterized by a packing pattern shown in FIG. 11(B), viewed down the crystallographic b axis. The hydrogen bonding scheme of compound 1 of FIG. 11(B) is shown in FIG. 11(C).

Form D can generally be prepared from a saturated solution of Compound 1 in a variety of solvents, such as acetone, ethyl acetate, ethanol, tetrahydrofuran, dichloromethane, DMF or an aqueous mixture thereof. Mixtures of acetone, ethyl acetate, ethanol, tetrahydrofuran, DMF and dichloromethane with or without water can also be used. For example, a mixture of ethanol, DMF and water can be used. In one embodiment, Form D is prepared from a saturated acetone-water solution of compound 1. Typically, acetone is major by volume. In one example, the acetone: water ratio is greater than 5:1 by volume. In another example, the acetone: water ratio is 7:1 by volume. Optionally, one or more seeds of Form D can be added to the acetone-water solution. Water is added to the acetone-water solution of compound 1 at ambient temperature. The resulting mixture is maintained at ambient temperature for a time period sufficient to cause at least a portion of compound 1 to precipitate. In one embodiment, the amount of the water added to the solution of compound 1, compared to the amount of acetone of the compound 1 solution, is greater than 1.8:1 water to acetone, by volume (e.g., greater than or equal to 2:1 by volume). Alternatively, the amount of the water added to the solution of compound 1, compared to the amount of acetone of the compound 1 solution, is less than 1:1 water to acetone, by volume (e.g. between 0.5:1 and 1:1, or between 0.75:1 and 1:1). In one embodiment, after addition of water to the compound 1 solution, the resulting mixture is stirred or agitated for a period of less than 5 hours (e.g. 1-5 hours or 2-4 hours). Alternatively, the mixture can be stirred for longer than 5 hours (e.g. longer than 8 hours, longer than 10 hours or between 8-12 hours). In another embodiment, the amount of the water added to the solution of compound 1, compared to the amount of acetone of the compound 1 solution is less than 1:1 water to acetone by volume and after addition of water, the resulting mixture is stirred or agitated for a period of less than 5 hours (e.g. 1-5 hours or 2-4 hours).

In another embodiment of preparation of Form D of compound 1, Form D is prepared by cooling of a hot saturated acetone-water solution of compound 1 from a temperature greater than 50° C. (e.g., between 50° C. and 70° C., such as at 60° C.) to ambient temperature Typically, the water to acetone ratio of the hot acetone-water solution of compound 1 is equal to or greater than 1:1 by volume.

In a specific embodiment, Form D of compound 1 has a bulk density of less or equal to 0.1 g/mL (≤0.1 g/mL).

In another specific embodiment, at a heating rate of 10° C./minute, Form D of compound 1 melts at 162±1.0° C.-164±1.0° C., followed by an exothermic transformation at 167±1.0° C.-169±1.0° C. and by melting at 190±1.0° C.-192±1.0° C.

Form D has a low tendency to form aggregates or granules, which is advantageous for manufacturing process. In one embodiment, Form D is substantially free of aggregates or granules. In another embodiment, less than 50%, 40%, 30%, 20%, 10%, 5% or 1% by weight of form D is aggregates or granules. Form D, for example, can be prepared according to Method 2 described in Example 4.

Other embodiments of the invention are directed to a single crystalline form of compound 1 characterized by a combination of the aforementioned characteristics of any of the single crystalline forms discussed herein. The characterization can be any combination of one or more of the XRPD, TGA, DSC and single crystal structure determination described for a particular crystalline form. For example, the single crystalline form of compound 1 can be characterized by any combination of the XRPD results regarding the 2θ angles of the major peaks in an XRPD scan; and/or any combination of one or more of the unit cell parameters derived from data obtained from the single crystal structure analysis.

Examples of combinations of single crystalline form characterizations using multiple analytical techniques include the 2θ positions of at least one of the major peaks of an XRPD scan and the temperature associated with the maximum heat flow during one or more heat flow transitions observed by a corresponding DSC measurements; the 2θ positions of at least one of the major peaks of an XRPD scan and one or more weight losses associated with a sample over a designated temperature range in a corresponding TGA measurement; the 2θ positions of at least one of the major peaks of an XRPD scan, and the temperature associated with the maximum heat flow during one or more heat flow transitions observed by a corresponding DSC measurements, and one or more weight losses associated with a sample over a designated temperature range in a corresponding TGA measurement. As well, each of the aforementioned examples can replace the use of 2θ positions of at least one of the major peaks of an XRPD scan with one or more unit cell parameters of the single crystalline form.

The combinations of characterization that are discussed above can be used to describe any of the single crystalline forms of compound 1 (e.g. Form A, C or D).

The single crystal forms disclosed herein can be a solvate or hydrate. "Solvates" refer to crystalline forms wherein solvent molecules are incorporated into the crystal lattice during crystallization. Solvates may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates." Hydrates include stoichiometric hydrates as well as compositions containing variable amounts of water. Alternatively, the crystal lattice of the disclosed single crystalline forms can be substantially free of water (i.e., anhydrous) or other solvents incorporated therein. In some specific embodiments, each of Forms A, C and D independently is substantially free of water (anhydrous) or other solvents. Typically, Form A, C or D substantially free of water or other solvents means less than 0.2 mole of water or any solvent per 1 mole of compound 1; typically less than 0.1 mole of water or any solvent per 1 mole of compound 1; more typically less than 0.05 mole of water or any solvent per 1 mole of compound 1.

In another embodiment of the invention, a pharmaceutical composition comprises a pharmaceutically acceptable carrier or diluent, and a single crystalline form of compound 1. In a specific embodiment, the single crystalline form is Form A of compound 1. In another specific embodiment, the single crystalline form is Form C of compound 1. In another specific embodiment, the single crystalline form is Form D of compound 1. Features, including specific features, of each of Forms A, C and D are as described above.

Suitable pharmaceutically acceptable carriers may contain inert ingredients which do not inhibit the biological activity of the disclosed compound. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed, such as those described in Remington's Pharmaceutical Sciences, Mack Publishing Company, Easton, Pa. Formulation of the compound to be administered will vary according to the route of administration selected (e.g., solution, emulsion, capsule). Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextrins) are known in the art (Baker, et al., "Controlled Release of Biological Active Agents", John Wiley and Sons, 1986).

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

Another embodiment of the present invention is a method of treating a subject with a cancer. Optionally, the method of the invention can be used for a multi-drug resistant cancer as described below. The method comprises the step of administering an effective amount of a compound or a pharmaceutical composition described herein. Other anti-proliferative or anticancer therapies may be combined with the compounds or the pharmaceutical compositions of this invention to treat proliferative diseases and cancer. Other therapies that may be used in combination with the inventive anticancer agents of the present invention include surgery, radiotherapy (including, but not limited to, gamma-radiation, neutron beam radiotherapy, electron beam radiotherapy, proton therapy, brachytherapy, and systemic radioactive isotopes) and endocrine therapy. Other anticancer agents that may be used in combination with the inventive anticancer agents of the present invention include biologic response modifiers (including, but not limited to, interferons, interleukins, and tumor necrosis factor (TNF)), hyperthermia and cryotherapy, agents to attenuate any adverse effects (e.g., antiemetics), and other approved chemotherapeutic drugs. Specific examples of anticancer agents are described in detail below. Preferably, the co-administered anti-cancer drug is an agent that stabilizes microtubules, such as paclitaxel or an analog of paclitaxel.

As noted above, one embodiment of the present invention is directed to treating subjects with a cancer. "Treating a subject with a cancer" includes achieving, partially or substantially, one or more of the following: arresting the growth or spread of a cancer, reducing the extent of a cancer (e.g., reducing size of a tumor or reducing the number of affected sites), inhibiting the growth rate of a cancer, and ameliorating or improving a clinical symptom or indicator associated with a cancer (such as tissue or serum components)

Cancers that can be treated or prevented by the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease.

Other examples of leukemias include acute and/or chronic leukemias, e.g., lymphocytic leukemia (e.g., as exemplified by the p388 (murine) cell line), large granular lymphocytic leukemia, and lymphoblastic leukemia; T-cell leukemias, e.g., T-cell leukemia (e.g., as exemplified by the CEM, Jurkat, and-HSB-2 (acute), YAC-1(murine) cell lines), T-lymphocytic leukemia, and T-lymphoblastic leukemia; B cell leukemia (e.g., as exemplified by the SB (acute) cell line), and B-lymphocytic leukemia; mixed cell leukemias, e.g., B and T cell leukemia and B and T lymphocytic leukemia; myeloid leukemias, e.g., granulocytic leukemia, myelocytic leukemia (e.g., as exemplified by the HL-60 (promyelocyte) cell line), and myelogenous leukemia (e.g., as exemplified by the K562 (chronic)cell line); neutrophilic leukemia; eosinophilic leukemia; monocytic leukemia (e.g., as exemplified by the THP-1(acute) cell line); myelomonocytic leukemia; Naegeli-type myeloid leukemia; and nonlymphocytic leukemia. Other examples of leukemias are described in Chapter 60 of *The Chemotherapy Sourcebook*, Michael C. Perry Ed., Williams & Williams (1992) and Section 36 of *Holland Frie Cancer Medicine* 5th Ed., Bast et al. Eds., B.C. Decker Inc. (2000). The entire teachings of the preceding references are incorporated herein by reference.

In one embodiment, the disclosed method is believed to be particularly effective in treating a subject with non-solid tumors such as multiple myeloma. In another embodiment, the disclosed method is believed to be particularly effective against T-leukemia (e.g., as exemplified by Jurkat and CEM cell lines); B-leukemia (e.g., as exemplified by the SB cell line); promyelocytes (e.g., as exemplified by the HL-60 cell line); uterine sarcoma (e.g., as exemplified by the MES-SA cell line); monocytic leukemia (e.g., as exemplified by the THP-1(acute) cell line); and lymphoma (e.g., as exemplified by the U937 cell line).

The disclosed method is particularly effective at treating subjects whose cancer has become "multi-drug resistant". A cancer which initially responded to an anti-cancer drug becomes resistant to the anti-cancer drug when the anti-cancer drug is no longer effective in treating the subject with the cancer. For example, many tumors will initially respond to treatment with an anti-cancer drug by decreasing in size or even going into remission, only to develop resistance to the drug. Drug resistant tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents.

An "effective amount" is the quantity of compound 1 in which a beneficial clinical outcome is achieved when the compound is administered to a subject with a cancer. A "beneficial clinical outcome" includes a reduction in tumor mass, a reduction in metastasis, a reduction in the severity of the symptoms associated with the cancer and/or an increase in the longevity of the subject compared with the absence of the treatment. The precise amount of compound administered to a subject will depend on the type and severity of the disease or condition and on the characteristics of the subject, such as general health, age, sex, body weight and tolerance to drugs. It will also depend on the degree, severity and type of cancer. The skilled artisan will be able to determine appropriate dosages depending on these and other factors. Effective amounts of the disclosed compounds typically range between about 1 mg/mm$^2$ per day and about 10 grams/mm$^2$ per day, and preferably between 10 mg/mm$^2$ per day and about 5 grams/mm$^2$. When co-administered with another anti-cancer agent, an "effective amount" of the second anti-cancer agent will depend on the type of drug used. Suitable dosages are known for approved anti-cancer agents and can be adjusted by the skilled artisan according to the condition of the subject, the type of cancer being treated and the amount of compound 1 being used.

The compound or a pharmaceutical composition disclosed herein is administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compound and pharmaceutical composition disclosed herein can also be administered orally (e.g., dietary), topically, by inhalation (e.g., intrabronchial, intranasal, oral inhalation or intranasal drops), or rectally, depending on the type of cancer to be treated. Oral and parenteral administrations are preferred modes of administration.

Optionally, the compound and pharmaceutical composition disclosed herein can be co-administered with other anti-cancer agents such as Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; foterriustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

Examples of therapeutic antibodies that can be used include but are not limited to HERCEPTIN® (Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); LYMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatied anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-sreptdavidin (+biotin–yttrium 90; NeoRx); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-β2 antibody (Cambridge Ab Tech).

Chemotherapeutic agents that can be used in the methods and compositions of the invention include but are not limited to alkylating agents, antimetabolites, natural products, or hormones. Examples of alkylating agents useful for the treatment or prevention of T-cell malignancies in the methods and compositions of the invention include but are not, limited to, nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites useful for the treatment or prevention of T-cell malignancies in the methods and compositions of the invention include but are not limited to folic acid analog (e.g., methotrexate), or pyrimidine analogs (e.g., Cytarabine), purine analogs (e.g., mercaptopurine, thioguanine, pentostatin). Examples of natural products useful for the treatment or prevention of T-cell malignancies in the methods and compositions of the invention include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents useful for the treatment or prevention of cancer in the methods and compositions of the invention include but are not limited to, nitrogen mustards (e.g., mechloroethamine, cyclophosphamide, chlorambucil, melphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites useful for the treatment or prevention of cancer in the methods and compositions of the invention include but are not limited to folic acid analog (e.g., methotrexate), or pyrimidine analogs (e.g., fluorouracil, floxouridine, Cytarabine), purine analogs (e.g., mercaptopurine, thioguanine, pentostatin). Examples of natural products useful for the treatment or prevention of cancer in the methods and compositions of the invention include but are not limited to vinca alkaloids (e.g., vinblastin, vincristine), epipodophyllotoxins (e.g., etoposide, teniposide), antibiotics (e.g., actinomycin D, daunorubicin, doxorubicin, bleomycin, plicamycin, mitomycin), enzymes (e.g., L-asparaginase), or biological response modifiers (e.g., interferon alpha). Examples of hormones and antagonists useful for the treatment or prevention of cancer in the methods and compositions of the invention include but are not limited to adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and with the compositions of the invention for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

The compound and pharmaceutical composition disclosed herein are believed to be particularly effective when co-administered with anti-cancer agents which act by arresting cells in the G2-M phases due to stabilization of microtubules. Thus, the disclosed method preferably includes co-administration of anti-cancer drugs which act by this mechanism. Examples of anti-cancer agents which act by arresting cells in the G2-M phases due to stabilization of microtubules include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia, LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HC1), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H 10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-IAABE (Cytoskeleton/Mt. Sinai School of Medicine), A-204197 (Abbott), T-607 (Tularik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-0Y-007 (National Health Research Institutes), and SSR-250411 (Sanofi), and Hsp90 inhibitors such as geldanmycin, radicicol, herbimycin A, macbecin I and II, novobiocin, 17-Allylamino-17-demethoxygeldanamycin (17AAG), 17-Demethoxy-17-[2-(dimethylamino)ethylamino]geldanamycin (17DMAG), CNF-1010, purine-based Hsp90 inhibitors such as PU3, PU24FC1, and PU29FC1, and oxime derivatives of radicicol such as KF25706 and KF58333.

Figure 12:
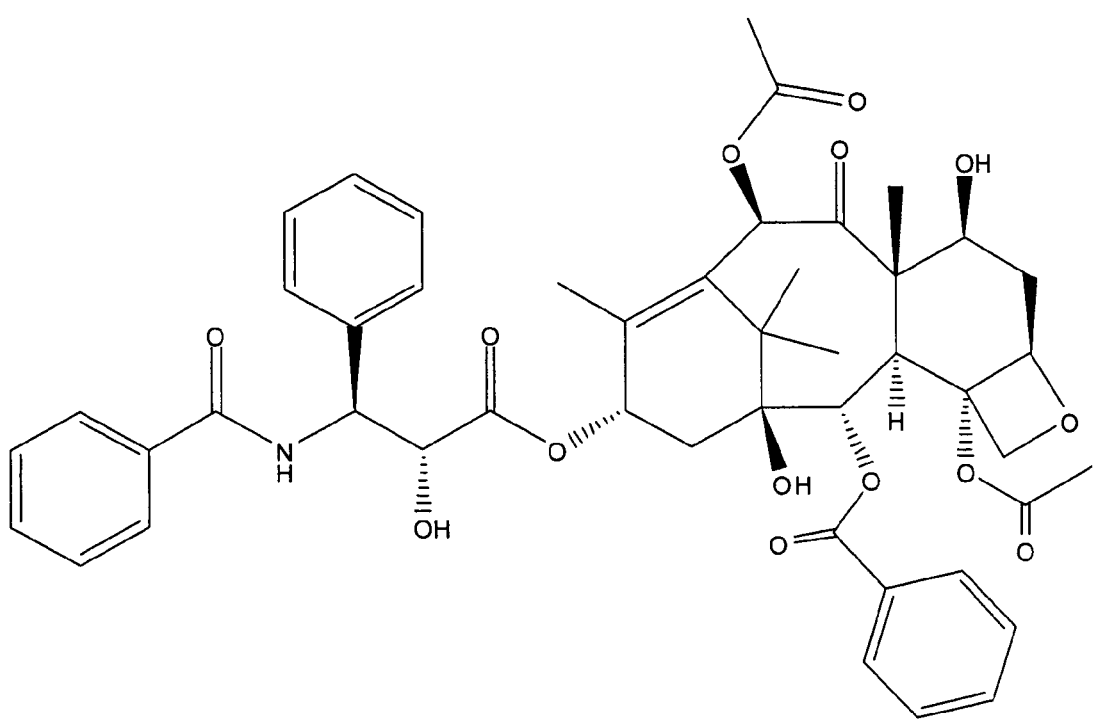
FIG. 12 is the structure of paclitaxel (TAXOL).
Figure 13:
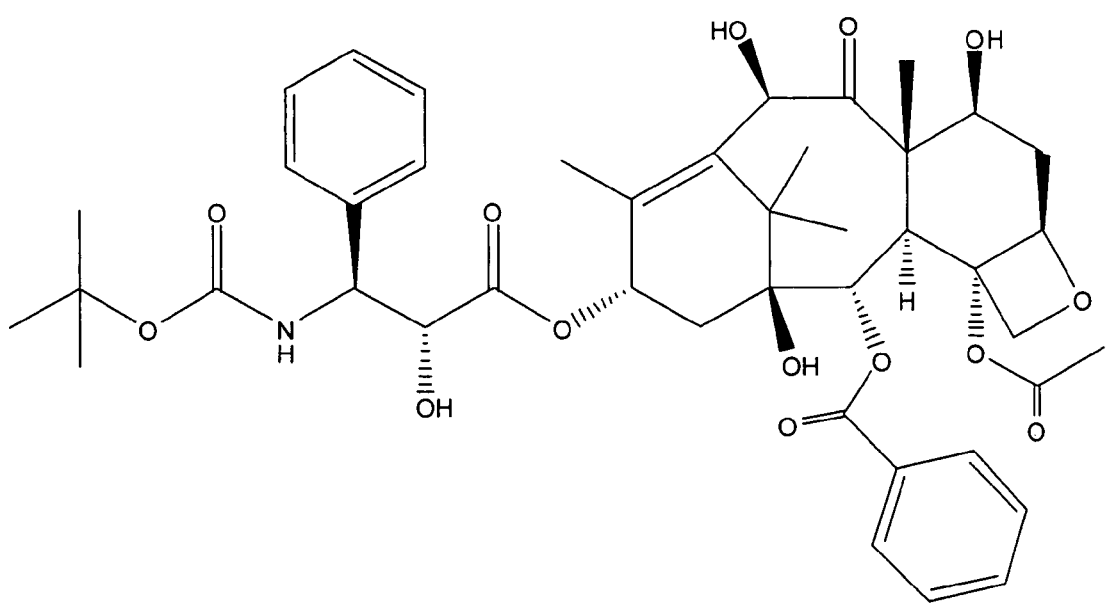
FIG. 13 is the structure of docetaxel (TAXOTERE).
Figure 14:
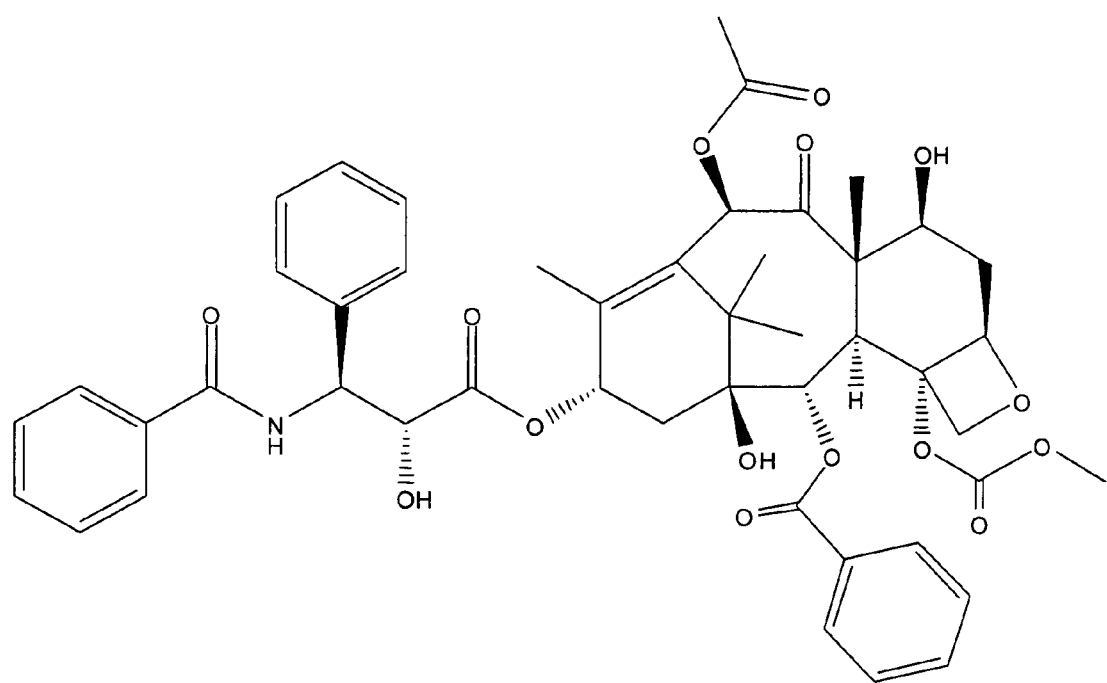
FIGS. 14-34 are each the structure of a paclitaxel analog.
Figure 15:
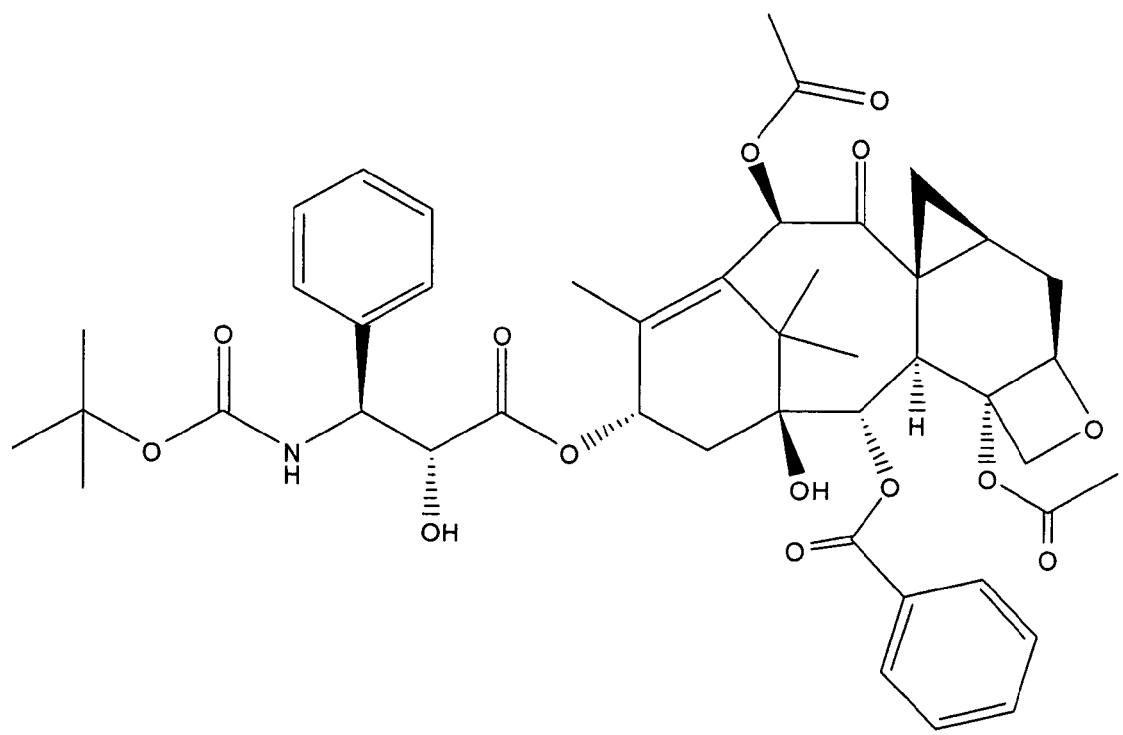
Figure 16:
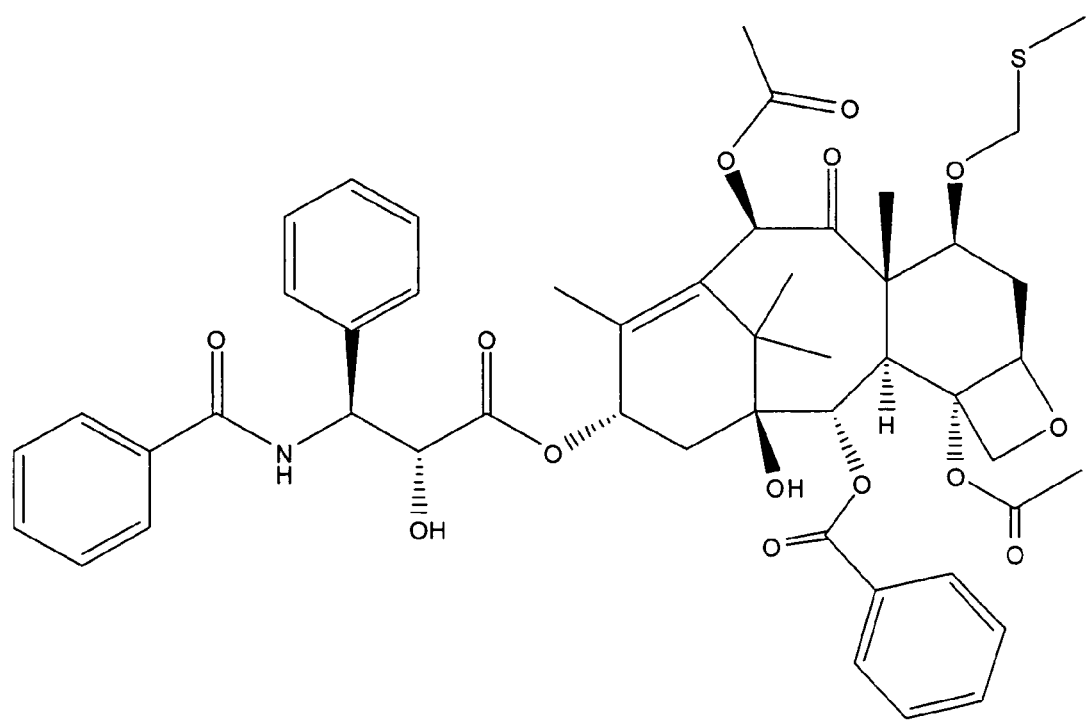
Figure 17:
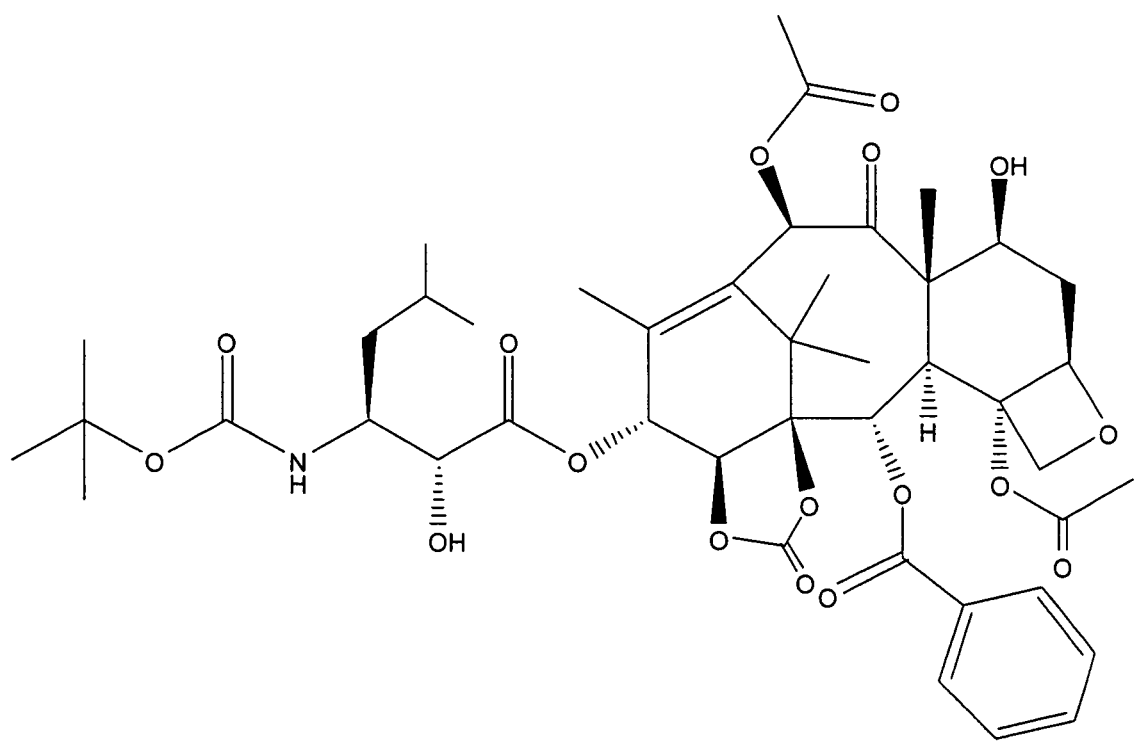
Figure 18:
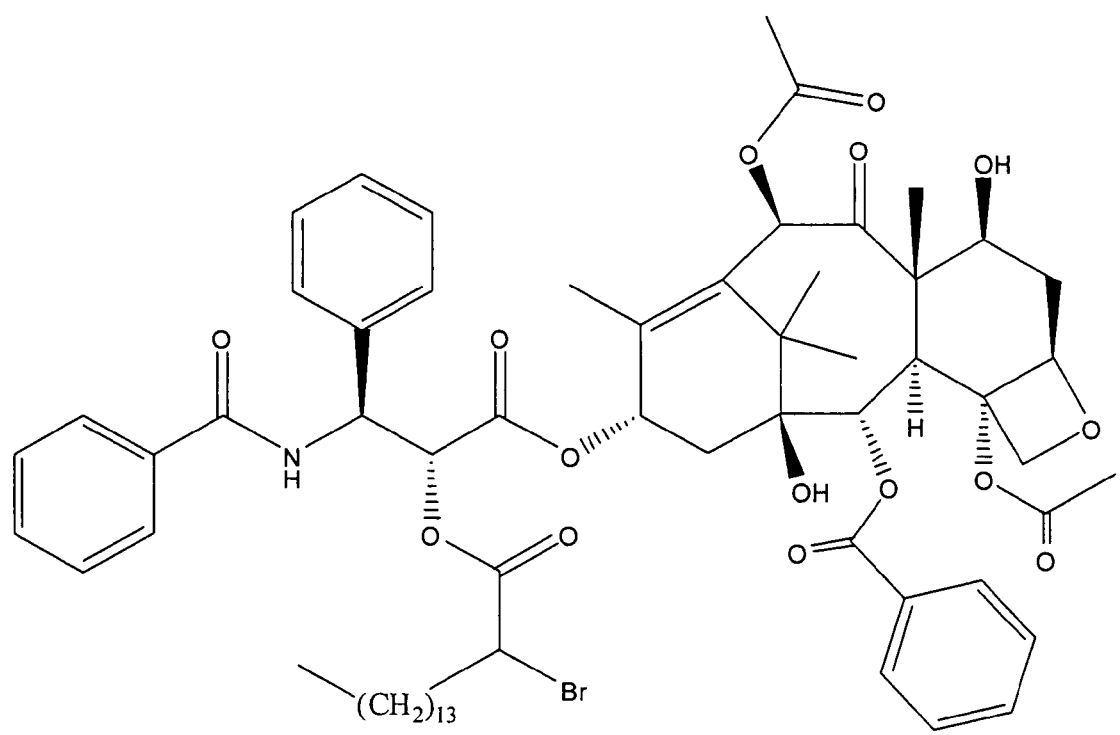
Figure 19:
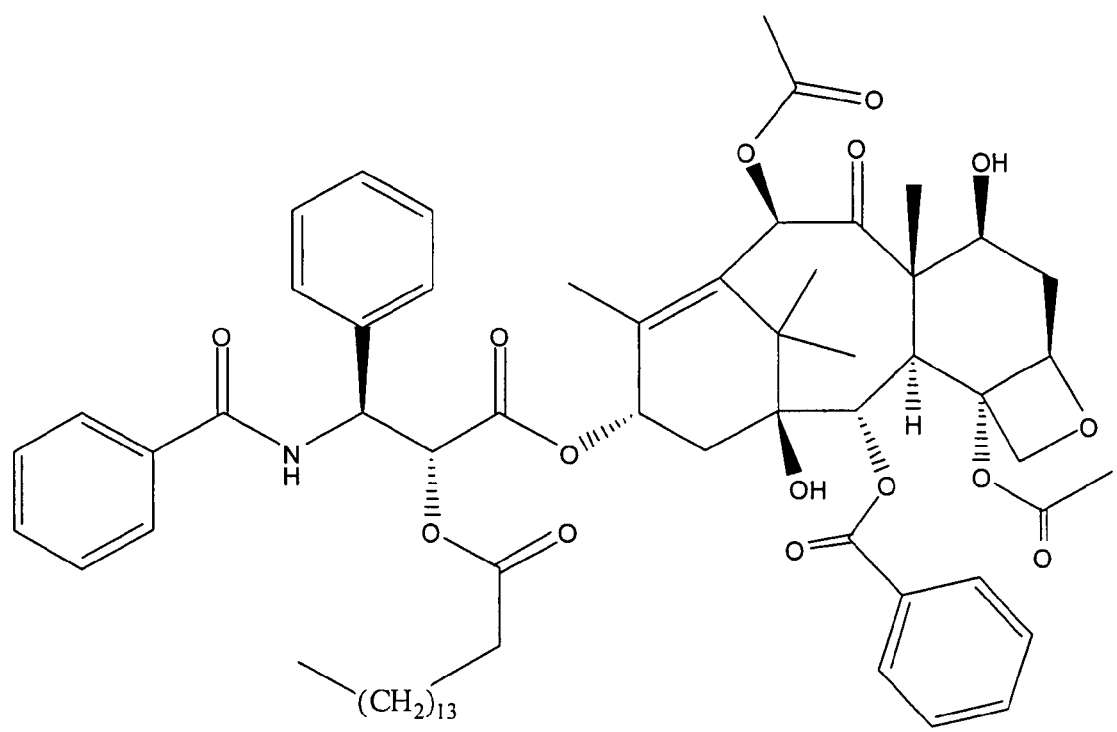
Figure 20:
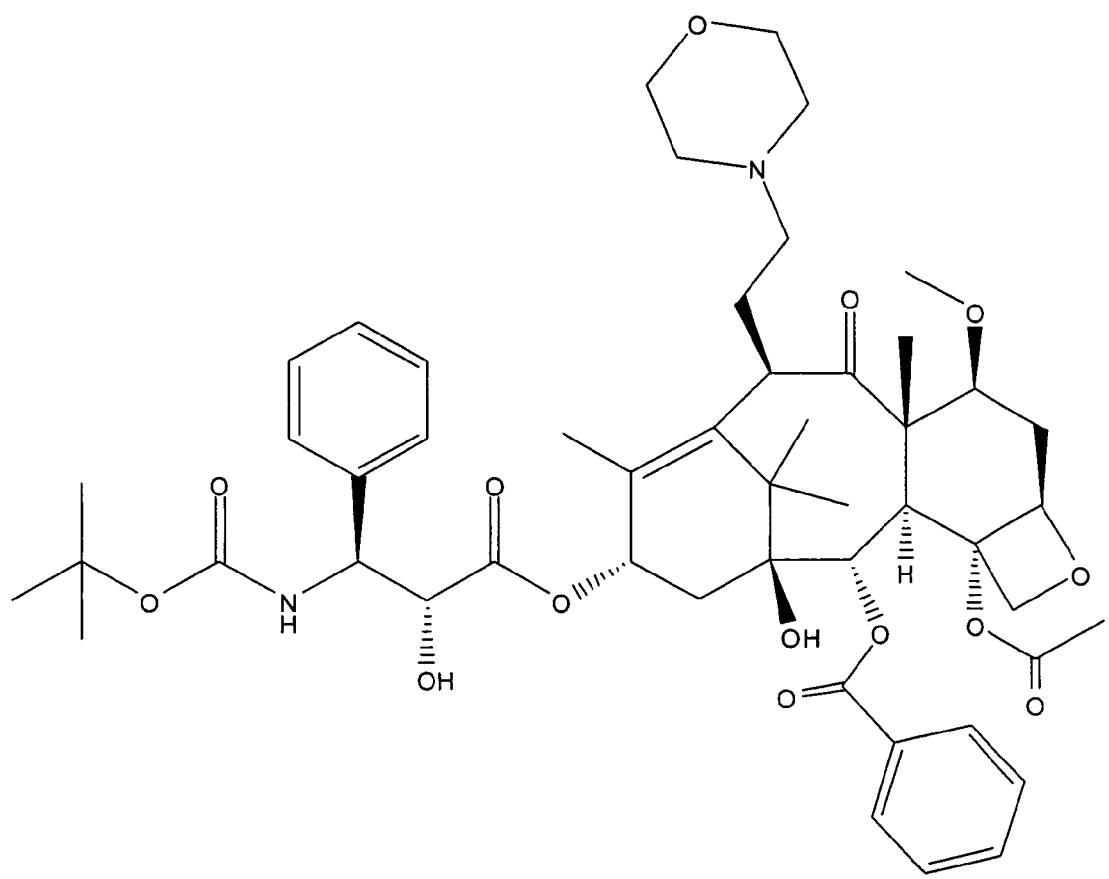
Figure 21:
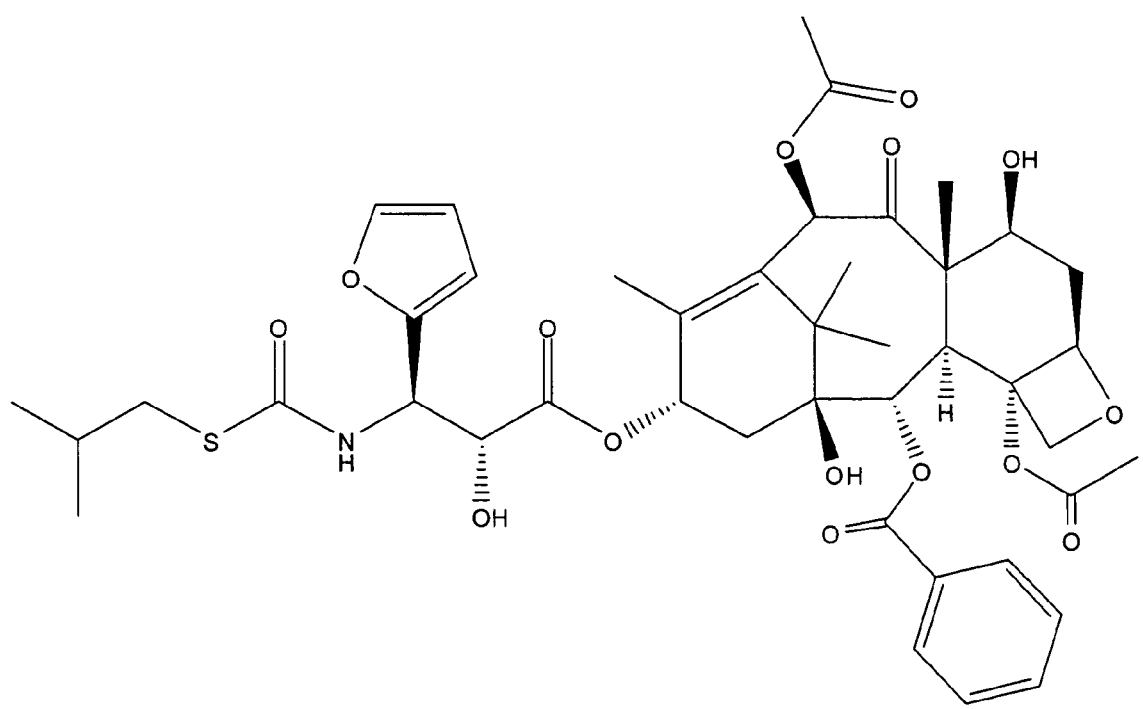
Figure 22:
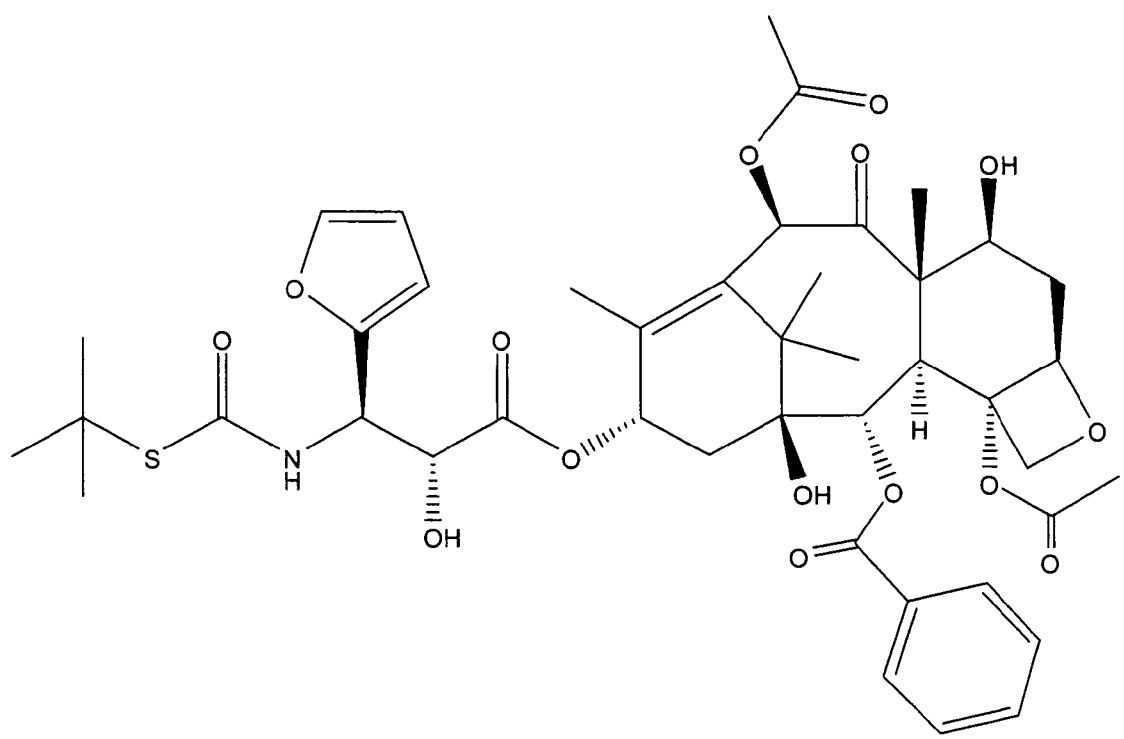
Figure 23:
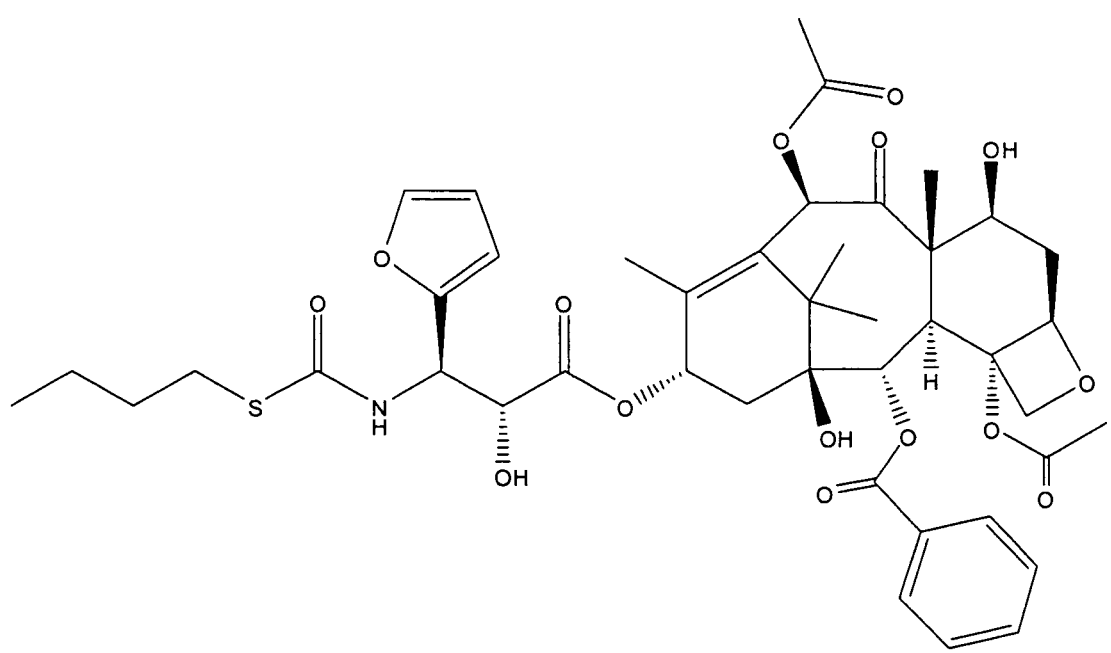
Figure 24:
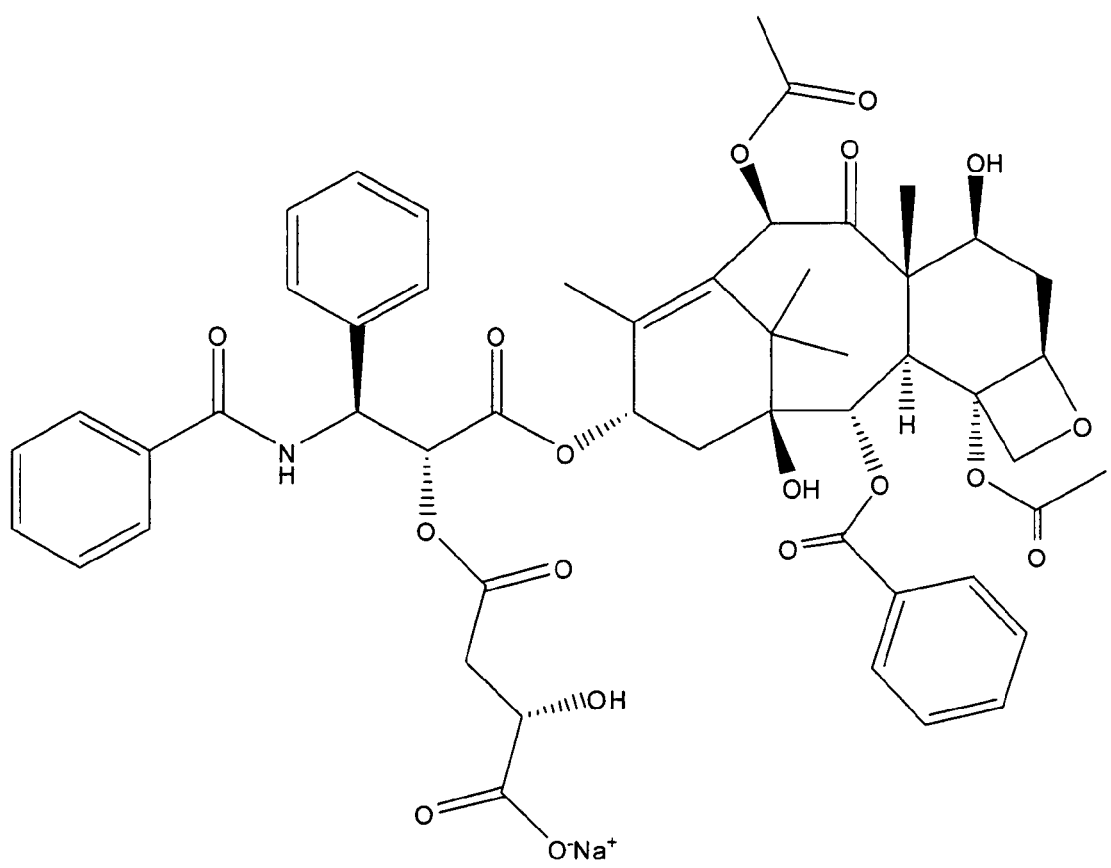
Figure 25:
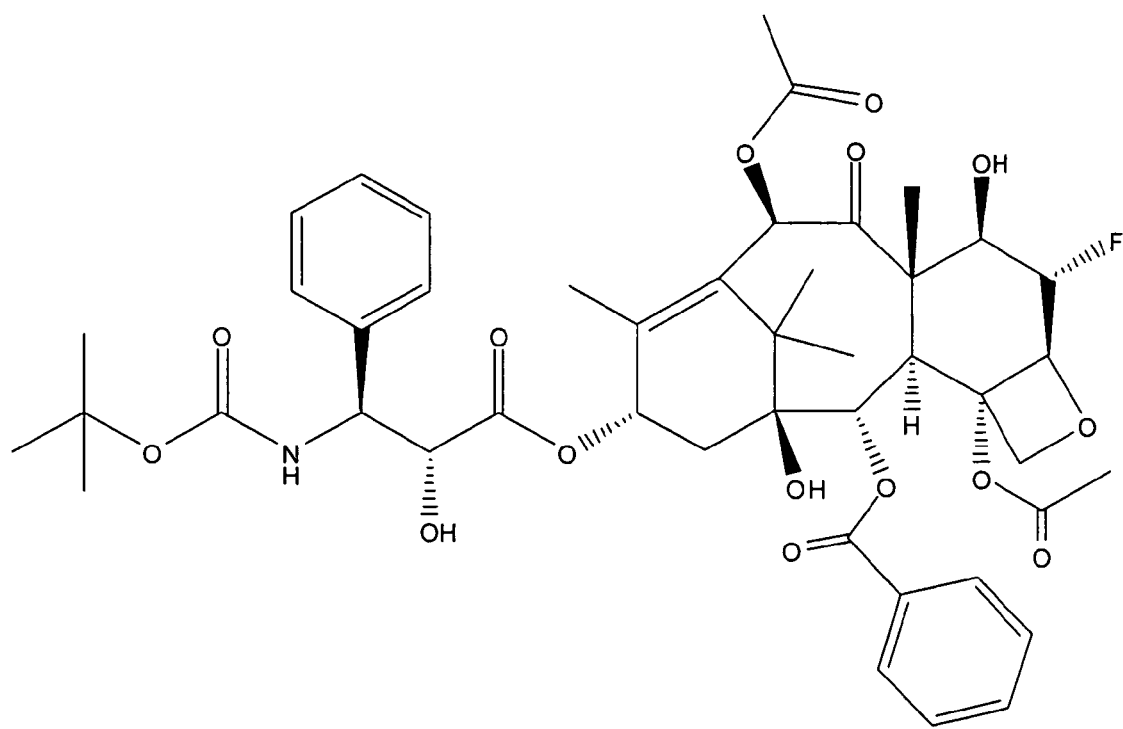
Figure 26:
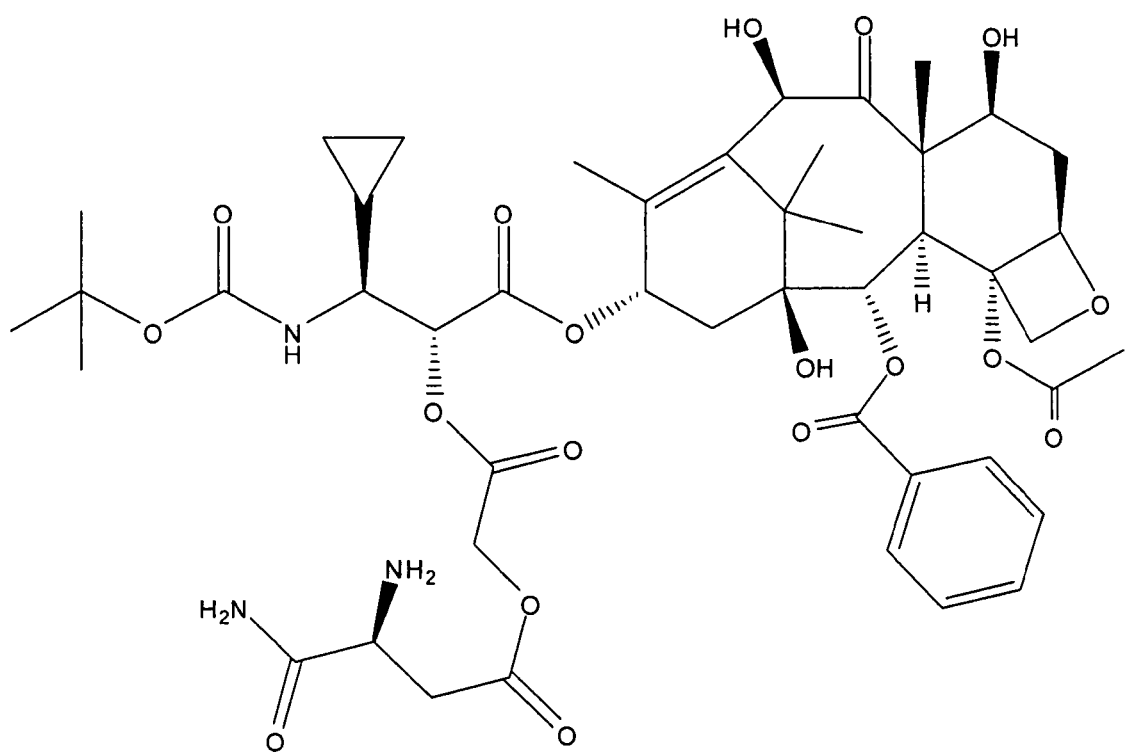
Figure 27:
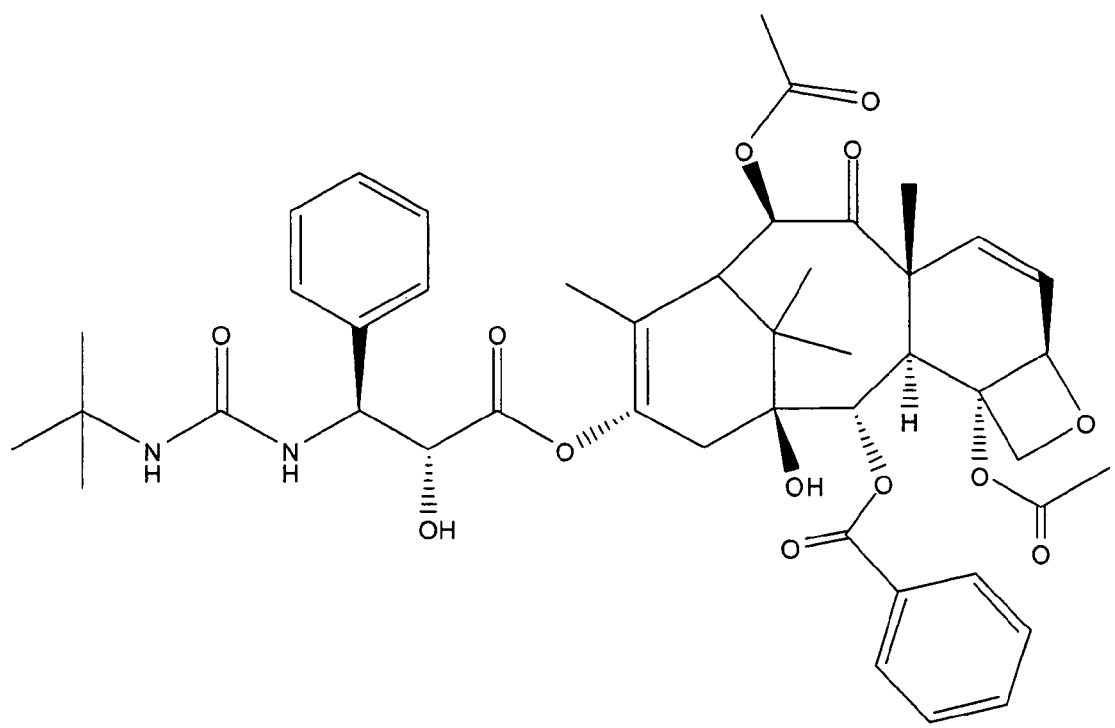
Figure 28:
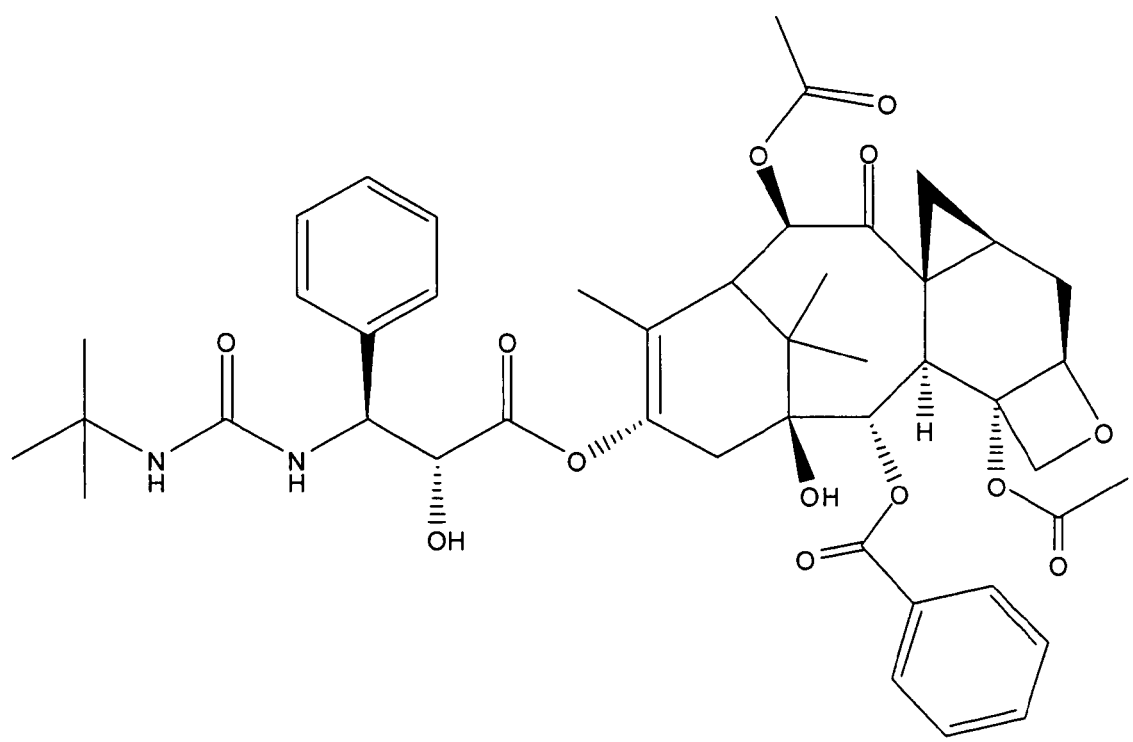
Figure 29:
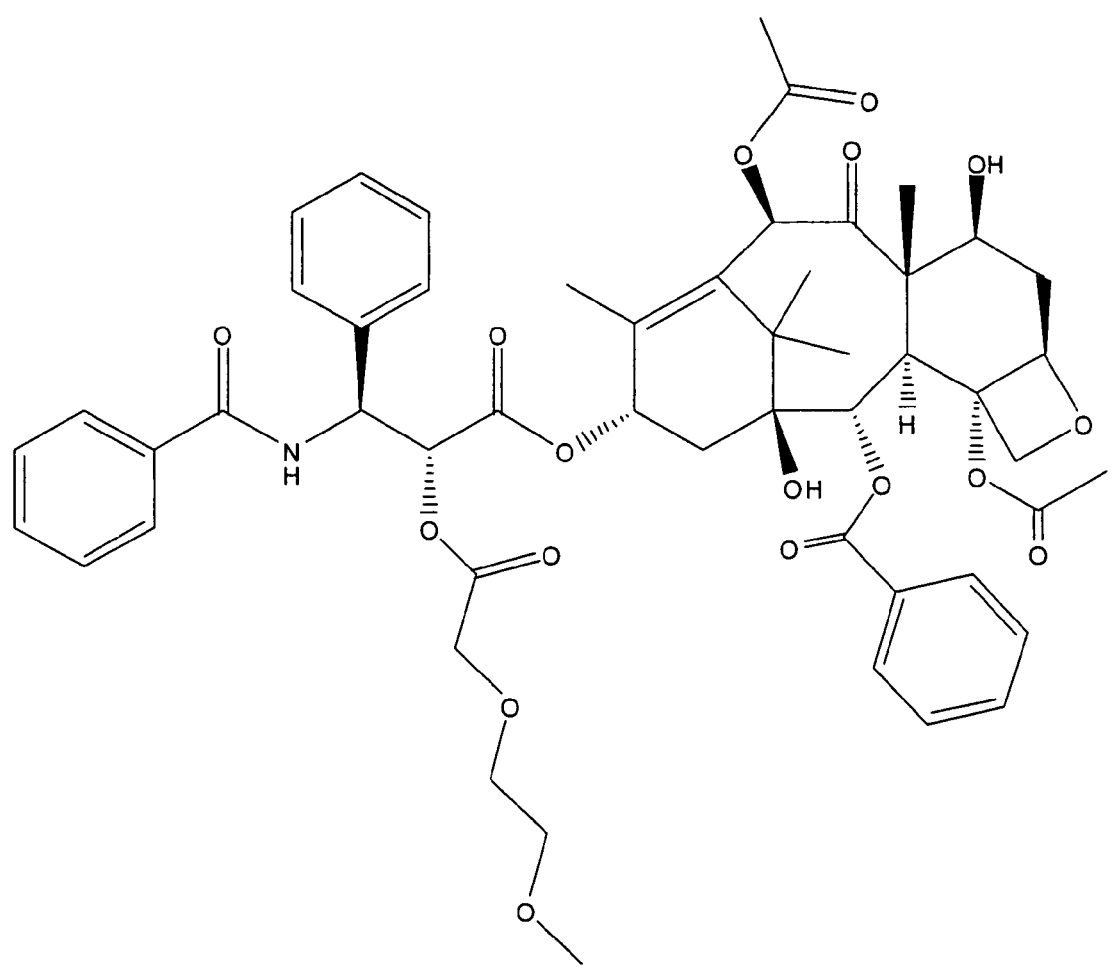
Figure 30:
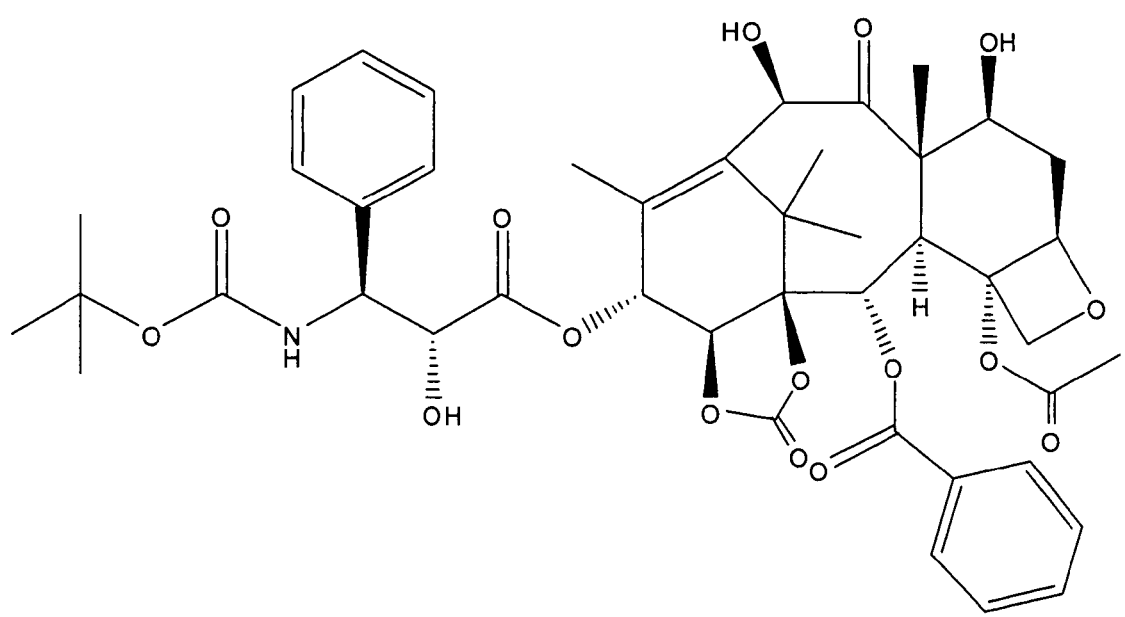
Figure 31:
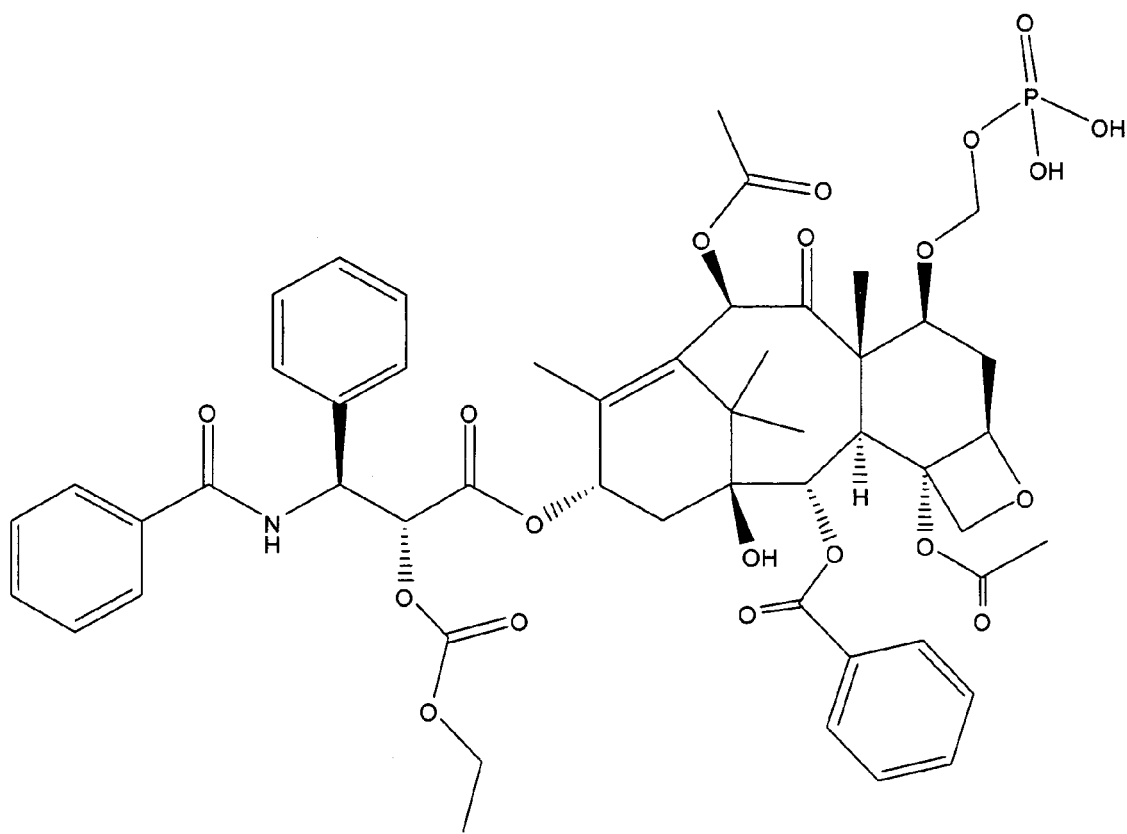
Figure 32:
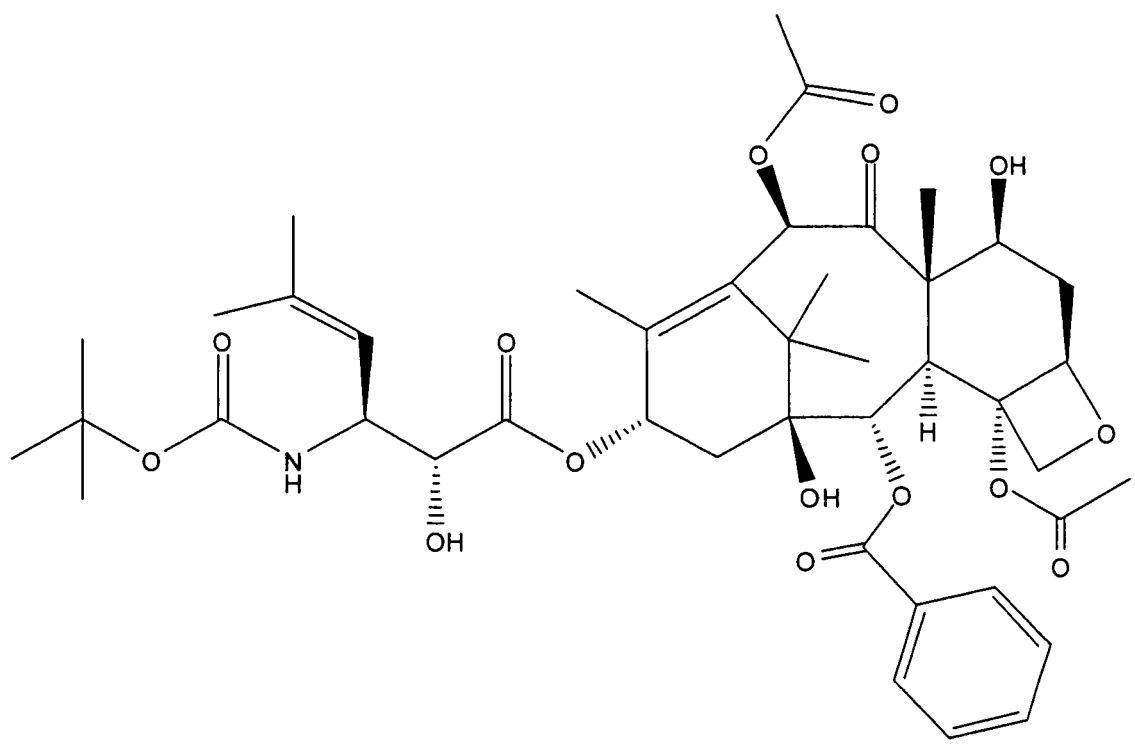
Figure 33:
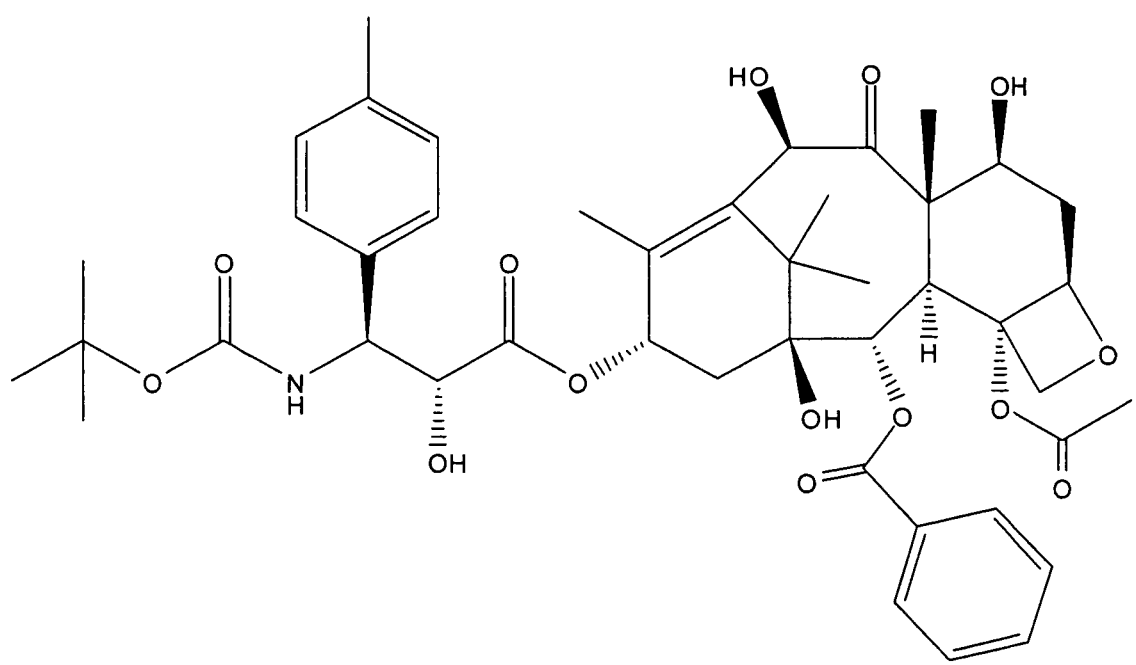
Figure 34:
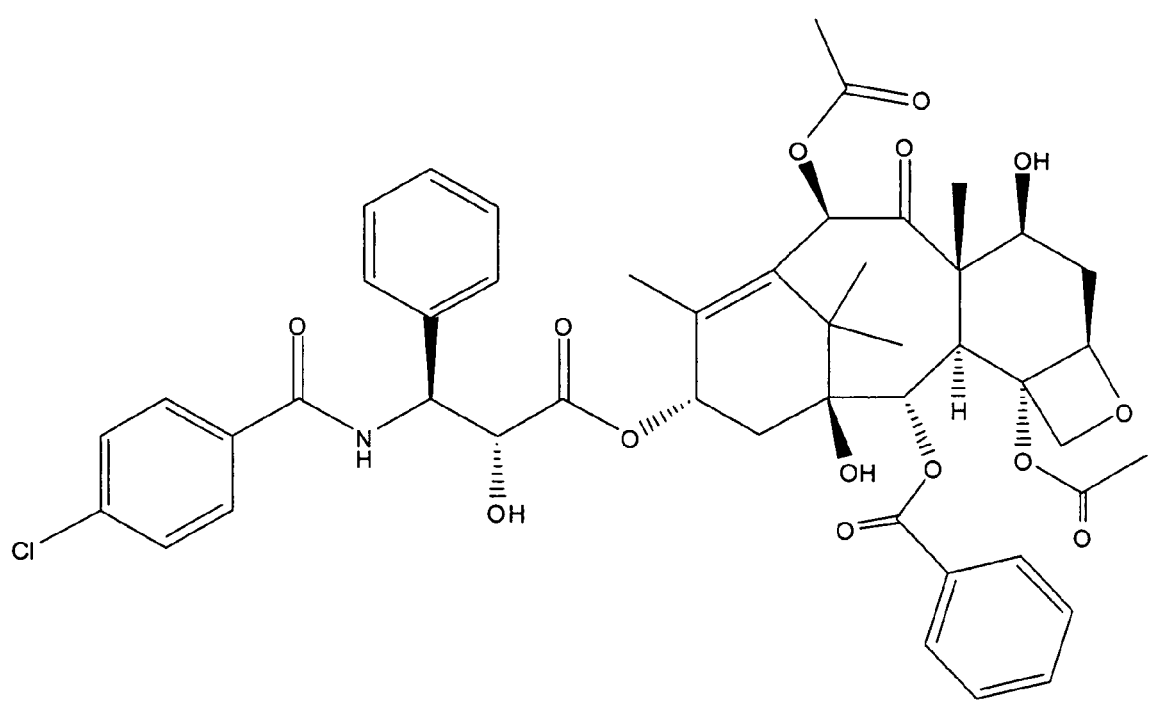

Paclitaxel, also referred to as "TAXOL", is a well-known anti-cancer drug which acts by enhancing and stabilizing microtubule formation. The structure of paclitaxel is shown in FIG. 12. Many analogs of paclitaxel are known, including docetaxel, the structure of which is shown in FIG. 13. Docetaxel is also referred to as "TAXOTERE". The structures of other paclitaxel analogs are shown in Figures. These compounds have the basic taxane skeleton as a common structure feature and have also been shown to have the ability to arrest cells in the G2-M phases due to stabilization of microtubules. Thus, it is apparent from FIGS. 14-34 that a wide variety of substituents can decorate the taxane skeleton without adversely affecting biological activity. It is also apparent that zero, one or both of the cyclohexane rings of a paclitaxel analog can have a double bond at the indicated positions. For clarity purposes, the basic taxane skeleton is shown below in Structural Formula (VI):

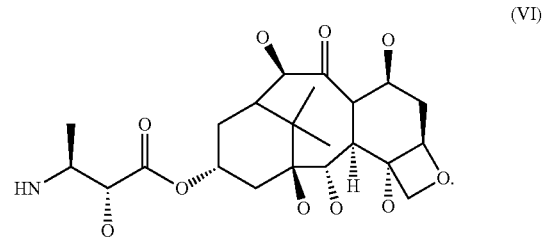

(VI)

Double bonds have been omitted from the cyclohexane rings in the taxane skeleton represented by Structural Formula (VI). The basic taxane skeleton can include zero or one double bond in one or both cyclohexane rings, as indicated in FIGS. 6-26 and Structural Formulas (VII) and (VIII) below. A number of atoms have also been omitted from Structural Formula (VI) to indicate sites in which structural variation commonly occurs among paclitaxel analogs. For example, substitution on the taxane skeleton with simply an oxygen atom indicates that hydroxyl, acyl, alkoxy or another oxygen-bearing substituent is commonly found at the site. These and other substitutions on the taxane skeleton can be made without losing the ability to enhance and stabilize microtubule formation. Thus, the term "paclitaxel analog" is defined herein to mean a compound which has the basic paclitaxel skeleton and which promotes microtubule formation. Paclitaxel analogs may be formulated as a nanoparticle colloidal composition to improve the infusion time and to eliminate the need to deliver the drug with Cremophor which causes hypersensitivity reactions in some patients. An example of a paclitaxel analog formulated as a nanoparticle colloidal composition is ABI-007 which is a nanoparticle colloidal composition of protein-stabilized paclitaxel that is reconstituted in saline.

Typically, the paclitaxel analogs used herein are represented by Structural Formula (VII) or (VIII):

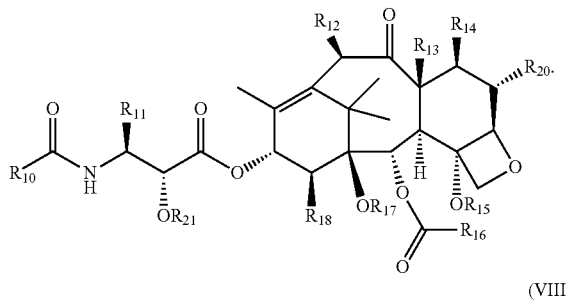

(VII)

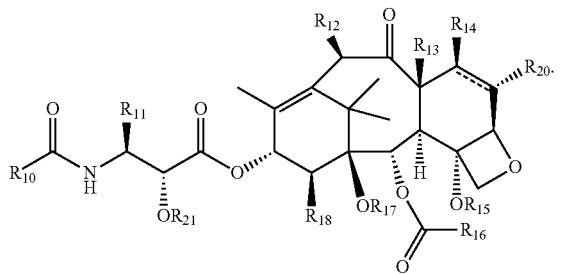

(VIII)

$R_{10}$ is a lower alkyl group, a substituted lower alkyl group, a phenyl group, a substituted phenyl group, —$SR_{19}$, —$NHR_{19}$ or —$OR_{19}$.

$R_{11}$ is a lower alkyl group, a substituted lower alkyl group, an aryl group or a substituted aryl group.

$R_{12}$ is —H, —OH, lower alkyl, substituted lower alkyl, lower alkoxy, substituted lower alkoxy, —O—C(O)-(lower alkyl), —O—C(O)-(substituted lower alkyl), —O—CH$_2$—O-(lower alkyl) —S—CH$_2$—O-(lower alkyl).

$R_{13}$ is —H, —CH$_3$, or, taken together with $R_{14}$, —CH$_2$—.

$R_{14}$ is —H, —OH, lower alkoxy, —O—C(O)-(lower alkyl), substituted lower alkoxy, —O—C(O)-(substituted lower alkyl), —O—CH$_2$—O—P(O)(OH)$_2$, —O—CH$_2$—O-(lower alkyl), —O—CH$_2$—S-(lower alkyl) or, taken together with $R_{20}$, a double bond.

$R_{15}$—H, lower acyl, lower alkyl, substituted lower alkyl, alkoxymethyl, alkthiomethyl, —OC(O)—O(lower alkyl), —OC(O)—O(substituted lower alkyl), —OC(O)—NH(lower alkyl) or —OC(O)—NH(substituted lower alkyl).

$R_{16}$ is phenyl or substituted phenyl.

$R_{17}$ is —H, lower acyl, substituted lower acyl, lower alkyl, substituted, lower alkyl, (lower alkoxy)methyl or (lower alkyl)thiomethyl.

$R_{18}$—H, —CH$_3$ or, taken together with $R_{17}$ and the carbon atoms to which $R_{17}$ and $R_{18}$ are bonded, a five or six membered a non-aromatic heterocyclic ring.

$R_{19}$ is a lower alkyl group, a substituted lower alkyl group, a phenyl group, a substituted phenyl group.

$R_{20}$ is —H or a halogen.

$R_{21}$ is —H, lower alkyl, substituted lower alkyl, lower acyl or substituted lower acyl.

Preferably, the variables in Structural Formulas (VII) and (VIII) are defined as follows: $R_{10}$ is phenyl, tert-butoxy, —S—CH$_2$—CH—(CH$_3$)$_2$, —S—CH(CH$_3$)$_3$, —S—(CH$_2$)$_3$CH$_3$, —O—CH(CH$_3$)$_3$, —NH—CH(CH$_3$)$_3$, —CH═C(CH$_3$)$_2$ or para-chlorophenyl; $R_{11}$ is phenyl, (CH$_3$)$_2$CHCH$_2$—, -2-furanyl, cyclopropyl or para-toluyl; $R_{12}$ is —H, —OH, CH$_3$CO— or —(CH$_2$)$_2$—N-morpholino; $R_{13}$ is methyl, or, $R_{13}$ and $R_{14}$, taken together, are —CH$_2$—;

$R_{14}$ is —H, —CH$_2$SCH$_3$ or —CH$_2$—O—P(O)(OH)$_2$; $R_{15}$ is CH$_3$CO—;

$R_{16}$ is phenyl; $R_{17}$—H, or, $R_{17}$ and $R_{18}$, taken together, are —O—CO—O—;

$R_{18}$ is —H; $R_{20}$ is —H or —F; and $R_{21}$ is —H, —C(O)—CHBr—(CH$_2$)$_{13}$—CH$_3$ or —C(O)—(O)—(CH$_2$)$_{14}$—CH$_3$; —C(O)—CH$_2$—CH(OH)—COOH, —C(O)—CH$_2$—O—C(O)—CH$_2$CH(NH$_2$)—CONH$_2$, —C(O)—CH$_2$—O—CH$_2$CH$_2$OCH$_3$ or —C(O)—O—C(O)—CH$_2$CH$_3$.

Figure 35:
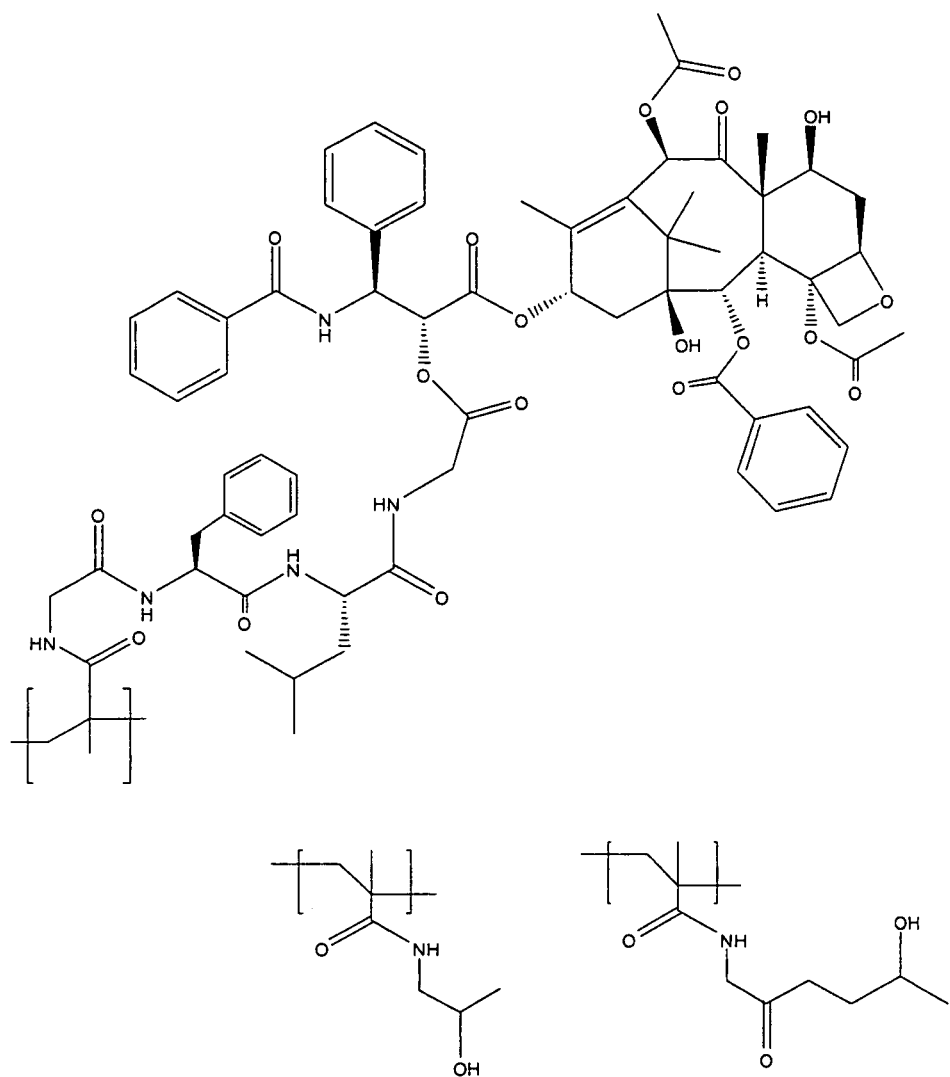
FIG. 35 is the structure of a polymer comprising a paclitaxel analog group pendent from the polymer backbone. The polymer is a terpolymer of the three monomer units shown.

A paclitaxel analog can also be bonded to or be pendent from a pharmaceutically acceptable polymer, such as a polyacrylamide. One example of a polymer of this type is shown in FIG. 35. The term "paclitaxel analog", as it is used herein, includes such polymers.

In co-therapy in combination with one or more other therapeutic agents (e.g., paclitaxel or paclitaxel analogs), the compound or the pharmaceutical composition disclosed herein can be administered simultaneously or separately with the other therapeutic agent(s). The exact details of the administration will depend on the pharmacokinetics of the two substances in the presence of each other, and can include administering two substances substantially at the same time, and one substance within a certain time period (e.g., within 24 hours) of administration of the other, if the pharmacokinetics are suitable. Designs of suitable dosing regimens are routine for one skilled in the art. In particular embodiments, two substances will be administered substantially simultaneously, i.e. within minutes of each other, or in a single composition that comprises both substances.

The disclosed crystalline forms and crystal habits of compound 1 can be prepared according to methods described above. In some specific embodiments, the disclosed crystalline forms and crystal habits of compound 1 can be prepared according to methods described in Examples 1-4. Compound 1 can be prepared according to methods described in U.S. Pat. Nos. 6,800,660, 6,762,204, and 6,825,235, and U.S. Publication No. 2008/0146842. The entire teachings of these publications and application are incorporated herein by reference.

The present invention is illustrated by the following examples, which are not intended to be limiting in any way.

EXEMPLIFICATION

X-Ray Powder Diffraction

X-ray powder diffraction (XRPD) analyses were performed using an Inel XRG-3000 diffractometer equipped with a CPS (Curved Position Sensitive) detector with a 2θ range of 120°. Real time data were collected using Cu—Kα radiation at a resolution of 0.03°2θ. The tube voltage and amperage were set to 40 kV and 30 mA, respectively. The monochromator slit was set at 5 mm by 160 μm. The pattern is displayed from 2.5-40° 2θ. Samples were prepared for analysis by packing them into thin-walled glass capillaries. Each capillary was mounted onto a goniometer head that is motorized to permit spinning of the capillary during data acquisition. The samples were analyzed for 300 sec. Instrument calibration was performed using a silicon reference standard.

Any XRPD files generated from Inel XRPD instruments were converted to Shimadzu raw file using File Monkey version 3.1.2. The Shimadzu raw file was processed by the Shimadzu XRD-6100/7000 version5.0 software to automatically find peak positions. The "peak position" means the maximum intensity of a peaked intensity profile. Parameters used in peak selection are shown in the lower half of each parameter set of the data. The following processes were used with the Shimadzu XRD-6100/7000 "Basic Process" version 1.01 algorithm:

Smoothing was done on all patterns.
The background was subtracted to find the net, relative intensity of the peaks.
A peak from Cu K alpha2 (1.5444 Å) wavelength was subtracted from the peak generated by Cu K alpha1 (1.5406 Å) peak at 50% intensity for all patterns.

Specific XRPD peak data and measurement conditions for the XRPD data are summarized in Tables 5-7:

TABLE 5

XRPD pattern of Form A of FIG. 1

Measurement Condition:

X-ray tube

| | |
|---|---|
| target = | Cu |
| voltage = | 0.0 (kV) |
| current = | 0.0 (mA) |

Slits

| | |
|---|---|
| divergence slit = | 0.00000 (deg) |
| scatter slit = | 0.00000 (deg) |
| receiving slit = | 0.00000 (mm) |

Scanning

| | |
|---|---|
| drive axis = | 2Theta/Theta |
| scan range = | 3.009-39.969 |
| scan mode = | |
| scan speed = | 0.0060 (deg/min) |
| sampling pitch = | 0.0300 (deg) |
| preset time = | 300.00 (sec) |

Data Process Condition:

| | |
|---|---|
| Smoothing | [AUTO] |
| smoothing points = | 9 |
| B.G. Subtraction | [AUTO] |
| sampling points = | 9 |
| repeat times = | 30 |
| Ka1-a2 Separate | [MANUAL] |
| Ka1 a2 ratio = | 50.0 (%) |
| Peak Search | [AUTO] |
| differential points = | 9 |
| FWHM threshold = | 0.050 (deg) |
| intensity threshold = | 30 (par mil) |
| FWHM ratio (n − 1)/n = | 2 |
| System Error Correction: | [NO] |
| Precise Peak Correction: | [NO] |
| Peak Data List | [Total No. = 35] |

| No. | 2Theta | d | I | I/Io | FWHM | Integrated I |
|---|---|---|---|---|---|---|
| 1 | 8.2892 | 10.65807 | 648 | 9 | 0.14920 | 5660 |
| 2 | 8.6048 | 10.26786 | 5334 | 72 | 0.24370 | 46266 |
| 3 | 10.7629 | 8.21338 | 1656 | 22 | 0.25510 | 16960 |
| 4 | 12.4049 | 7.12964 | 276 | 4 | 0.22080 | 3125 |
| 5 | 13.4814 | 6.56266 | 474 | 6 | 0.20350 | 5436 |
| 6 | 14.4934 | 6.10662 | 2376 | 32 | 0.22410 | 20376 |
| 7 | 15.2416 | 5.80849 | 443 | 6 | 0.22160 | 3801 |
| 8 | 16.3279 | 5.42441 | 1921 | 26 | 0.29360 | 21133 |
| 9 | 17.4870 | 5.06739 | 585 | 8 | 0.27150 | 6673 |

TABLE 5-continued

XRPD pattern of Form A of FIG. 1

| No. | 2Theta | d | I | I/Io | FWHM | Integrated I |
|---|---|---|---|---|---|---|
| 10 | 18.7433 | 4.73047 | 7414 | 100 | 0.21570 | 58711 |
| 11 | 19.1767 | 4.62453 | 1710 | 23 | 0.29850 | 18547 |
| 12 | 19.9271 | 4.45204 | 1308 | 18 | 0.23250 | 11927 |
| 13 | 20.9248 | 4.24197 | 5151 | 69 | 0.22510 | 45299 |
| 14 | 22.5025 | 3.94799 | 876 | 12 | 0.30930 | 9526 |
| 15 | 23.1692 | 3.83588 | 271 | 4 | 0.30760 | 4066 |
| 16 | 23.6539 | 3.75836 | 2801 | 38 | 0.26990 | 25708 |
| 17 | 24.1188 | 3.68696 | 2329 | 31 | 0.28740 | 25013 |
| 18 | 24.7592 | 3.59303 | 366 | 5 | 0.25260 | 4780 |
| 19 | 25.8834 | 3.43946 | 398 | 5 | 0.31480 | 4830 |
| 20 | 27.1324 | 3.28390 | 281 | 4 | 0.25150 | 2646 |
| 21 | 27.7156 | 3.21611 | 1426 | 19 | 0.30930 | 15851 |
| 22 | 28.4492 | 3.13482 | 526 | 7 | 0.24300 | 6279 |
| 23 | 28.6892 | 3.10914 | 415 | 6 | 0.00000 | 0 |
| 24 | 29.1844 | 3.05750 | 968 | 13 | 0.28630 | 12799 |
| 25 | 30.0092 | 2.97532 | 428 | 6 | 0.37720 | 4437 |
| 26 | 30.2792 | 2.94940 | 356 | 5 | 0.32700 | 3605 |
| 27 | 30.7289 | 2.90725 | 598 | 8 | 0.24640 | 5860 |
| 28 | 31.8144 | 2.81049 | 270 | 4 | 0.28430 | 2778 |
| 29 | 32.3492 | 2.76524 | 233 | 3 | 0.17380 | 1256 |
| 30 | 32.5592 | 2.74788 | 318 | 4 | 0.26780 | 3117 |
| 31 | 33.3759 | 2.68249 | 274 | 4 | 0.30550 | 5110 |
| 32 | 34.9993 | 2.56169 | 509 | 7 | 0.31660 | 6901 |
| 33 | 36.6432 | 2.45045 | 247 | 3 | 0.32300 | 3782 |
| 34 | 38.7328 | 2.32292 | 465 | 6 | 0.25070 | 4198 |
| 35 | 39.3422 | 2.28833 | 262 | 4 | 0.28810 | 3716 |

TABLE 6

XRPD pattern of Form A of FIG. 5

Measurement Condition:

X-ray tube

| | |
|---|---|
| target = | Cu |
| voltage = | 0.0 (kV) |
| current = | 0.0 (mA) |

Slits

| | |
|---|---|
| divergence slit = | 0.00000 (deg) |
| scatter slit = | 0.00000 (deg) |
| receiving slit = | 0.00000 (mm) |

Scanning

| | |
|---|---|
| drive axis = | 2Theta/Theta |
| scan range = | 3.009-39.969 |
| scan mode = | |
| scan speed = | 0.0060 (deg/min) |
| sampling pitch = | 0.0300 (deg) |
| preset time = | 300.00 (sec) |

Data Process Condition:

| | |
|---|---|
| Smoothing | [AUTO] |
| smoothing points = | 9 |
| B.G. Subtraction | [AUTO] |
| sampling points = | 11 |
| repeat times = | 30 |
| Ka1-a2 Separate | [MANUAL] |
| Ka1 a2 ratio = | 50.0 (%) |
| Peak Search | [AUTO] |
| differential points = | 9 |
| FWHM threshold = | 0.050 (deg) |
| intensity threshold = | 30 (par mil) |
| FWHM ratio (n − 1)/n = | 2 |
| System Error Correction: | [NO] |
| Precise Peak Correction: | [NO] |
| Peak Data List | [Total No. = 42] |

| No. | 2Theta | d | I | I/Io | FWHM | Integrated I |
|---|---|---|---|---|---|---|
| 1 | 5.1232 | 17.23518 | 158 | 4 | 0.28200 | 2450 |
| 2 | 8.6414 | 10.22445 | 3683 | 86 | 0.20660 | 28903 |
| 3 | 10.3206 | 8.56436 | 1467 | 34 | 0.20060 | 11768 |
| 4 | 11.8275 | 7.47637 | 197 | 5 | 0.19120 | 1648 |

TABLE 6-continued

XRPD pattern of Form A of FIG. 5

| | | | | | | |
|---|---|---|---|---|---|---|
| 5 | 12.9433 | 6.83426 | 613 | 14 | 0.23020 | 5410 |
| 6 | 13.8638 | 6.38249 | 264 | 6 | 0.23170 | 2126 |
| 7 | 14.8003 | 5.98067 | 1017 | 24 | 0.19500 | 7282 |
| 8 | 15.7041 | 5.63845 | 1124 | 26 | 0.35020 | 13467 |
| 9 | 16.8791 | 5.24850 | 1100 | 26 | 0.24490 | 9496 |
| 10 | 17.2872 | 5.12550 | 394 | 9 | 0.18250 | 2613 |
| 11 | 17.6444 | 5.02254 | 639 | 15 | 0.20560 | 4678 |
| 12 | 19.1514 | 4.63058 | 4271 | 100 | 0.22320 | 35706 |
| 13 | 19.6805 | 4.50727 | 893 | 21 | 0.23810 | 9108 |
| 14 | 20.3868 | 4.35268 | 471 | 11 | 0.24020 | 4121 |
| 15 | 20.8592 | 4.25516 | 459 | 11 | 0.34160 | 6123 |
| 16 | 21.0692 | 4.21322 | 555 | 13 | 0.00000 | 0 |
| 17 | 21.4871 | 4.13221 | 2732 | 64 | 0.20240 | 23167 |
| 18 | 21.9092 | 4.05355 | 287 | 7 | 0.23520 | 3324 |
| 19 | 22.7492 | 3.90574 | 322 | 8 | 0.13300 | 2658 |
| 20 | 23.0485 | 3.85569 | 1824 | 43 | 0.21190 | 14173 |
| 21 | 23.6412 | 3.76035 | 507 | 12 | 0.28180 | 5457 |
| 22 | 24.3430 | 3.65351 | 1008 | 24 | 0.25920 | 9377 |
| 23 | 24.9992 | 3.55907 | 304 | 7 | 0.23120 | 3504 |
| 24 | 25.2392 | 3.52577 | 239 | 6 | 0.00000 | 0 |
| 25 | 25.8129 | 3.44870 | 419 | 10 | 0.28140 | 6315 |
| 26 | 26.9277 | 3.30840 | 346 | 8 | 0.22050 | 2681 |
| 27 | 27.7507 | 3.21212 | 160 | 4 | 0.16550 | 1005 |
| 28 | 28.4792 | 3.13159 | 694 | 16 | 0.25820 | 5019 |
| 29 | 28.6592 | 3.11233 | 502 | 12 | 0.28560 | 3973 |
| 30 | 28.9817 | 3.07842 | 741 | 17 | 0.22440 | 5718 |
| 31 | 29.5730 | 3.01820 | 413 | 10 | 0.23980 | 3809 |
| 32 | 30.1205 | 2.96458 | 1037 | 24 | 0.29920 | 11894 |
| 33 | 30.9392 | 2.88797 | 187 | 4 | 0.15000 | 1392 |
| 34 | 31.2168 | 2.86292 | 715 | 17 | 0.24840 | 5472 |
| 35 | 31.4792 | 2.83965 | 220 | 5 | 0.18440 | 2060 |
| 36 | 32.0602 | 2.78950 | 252 | 6 | 0.29120 | 3432 |
| 37 | 33.5336 | 2.67023 | 273 | 6 | 0.15200 | 1518 |
| 38 | 34.6003 | 2.59031 | 212 | 5 | 0.25900 | 2851 |
| 39 | 36.3338 | 2.47060 | 255 | 6 | 0.24830 | 3795 |
| 40 | 37.9032 | 2.37184 | 245 | 6 | 0.25820 | 2635 |
| 41 | 38.4392 | 2.33999 | 162 | 4 | 0.17820 | 1257 |
| 42 | 38.7992 | 2.31910 | 179 | 4 | 0.14180 | 1534 |

TABLE 7

XRPD pattern of Form A of FIG. 7

Measurement Condition:

X-ray tube

| | |
|---|---|
| target = | Cu |
| voltage = | 0.0 (kV) |
| current = | 0.0 (mA) |

Slits

| | |
|---|---|
| divergence slit = | 0.00000 (deg) |
| scatter slit = | 0.00000 (deg) |
| receiving slit = | 0.00000 (mm) |

Scanning

| | |
|---|---|
| drive axis = | 2Theta/Theta |
| scan range = | 3.009-39.969 |
| scan mode = | |
| scan speed = | 0.0060 (deg/min) |
| sampling pitch = | 0.0300 (deg) |
| preset time = | 300.00 (sec) |

Data Process Condition:

| | |
|---|---|
| Smoothing | [AUTO] |
| smoothing points = | 11 |
| B.G. Subtraction | [AUTO] |
| sampling points = | 13 |
| repeat times = | 30 |
| Kα1-α2 Separate | [MANUAL] |
| Kα1 α2 ratio = | 50.0 (%) |
| Peak Search | [AUTO] |
| differential points = | 9 |
| FWHM threshold = | 0.050 (deg) |

TABLE 7-continued

XRPD pattern of Form A of FIG. 7

| | | |
|---|---|---|
| intensity threshold = | 30 (par mil) | |
| FWHM ratio (n − 1)/n = | 2 | |
| System Error Correction: | [NO] | |
| Precise Peak Correction: | [NO] | |
| Peak Data List | [Total No. = 51] | |

| No. | 2Theta | d | I | I/Io | FWHM | Integrated I |
|---|---|---|---|---|---|---|
| 1 | 6.5489 | 13.48592 | 316 | 12 | 0.31500 | 4751 |
| 2 | 7.5166 | 11.75175 | 2543 | 96 | 0.25550 | 23000 |
| 3 | 7.8392 | 11.26885 | 566 | 21 | 0.24740 | 6686 |
| 4 | 11.7899 | 7.50013 | 130 | 5 | 0.22140 | 1272 |
| 5 | 13.2235 | 6.69007 | 2572 | 97 | 0.23750 | 23386 |
| 6 | 13.9027 | 6.36472 | 2536 | 96 | 0.23410 | 21364 |
| 7 | 14.1992 | 6.23248 | 89 | 3 | 0.07420 | 705 |
| 8 | 15.0732 | 5.87300 | 159 | 6 | 0.23010 | 1705 |
| 9 | 15.8155 | 5.59898 | 1222 | 46 | 0.25330 | 11320 |
| 10 | 16.7541 | 5.28737 | 783 | 30 | 0.26450 | 7063 |
| 11 | 17.2295 | 5.14254 | 2468 | 93 | 0.30150 | 25766 |
| 12 | 17.6792 | 5.01273 | 127 | 5 | 0.16680 | 1191 |
| 13 | 18.6959 | 4.74236 | 1948 | 73 | 0.24660 | 17358 |
| 14 | 19.3892 | 4.57432 | 132 | 5 | 0.11840 | 704 |
| 15 | 19.7124 | 4.50005 | 2048 | 77 | 0.23740 | 17531 |
| 16 | 20.3492 | 4.36064 | 206 | 8 | 0.28240 | 2329 |
| 17 | 20.7967 | 4.26781 | 1587 | 60 | 0.30460 | 16922 |
| 18 | 21.3513 | 4.15819 | 271 | 10 | 0.24800 | 2999 |
| 19 | 22.0594 | 4.02628 | 2652 | 100 | 0.22900 | 21452 |
| 20 | 22.6592 | 3.92105 | 605 | 23 | 0.22500 | 4868 |
| 21 | 23.3492 | 3.80671 | 673 | 25 | 0.28520 | 5743 |
| 22 | 23.7392 | 3.74505 | 811 | 31 | 0.38100 | 9314 |
| 23 | 24.0692 | 3.69444 | 1461 | 55 | 0.28120 | 11218 |
| 24 | 24.3092 | 3.65851 | 2079 | 78 | 0.30380 | 20009 |
| 25 | 24.9748 | 3.56249 | 2328 | 88 | 0.25530 | 21643 |
| 26 | 25.2992 | 3.51754 | 159 | 6 | 0.11580 | 1303 |
| 27 | 25.7492 | 3.45708 | 171 | 6 | 0.22340 | 1274 |
| 28 | 26.0897 | 3.41273 | 457 | 17 | 0.25750 | 4258 |
| 29 | 26.6485 | 3.34242 | 1318 | 50 | 0.25180 | 12015 |
| 30 | 27.5431 | 3.23586 | 258 | 10 | 0.20650 | 1844 |
| 31 | 28.4388 | 3.13595 | 1067 | 40 | 0.27610 | 10638 |
| 32 | 29.1941 | 3.05651 | 2017 | 76 | 0.24500 | 18271 |
| 33 | 29.7900 | 2.99671 | 509 | 19 | 0.23350 | 4962 |
| 34 | 30.4592 | 2.93238 | 568 | 21 | 0.30200 | 5844 |
| 35 | 30.7592 | 2.90446 | 387 | 15 | 0.23420 | 3462 |
| 36 | 31.3217 | 2.85357 | 112 | 4 | 0.25500 | 969 |
| 37 | 31.7059 | 2.81986 | 380 | 14 | 0.25450 | 3157 |
| 38 | 32.1092 | 2.78536 | 156 | 6 | 0.18160 | 1173 |
| 39 | 32.3792 | 2.76275 | 223 | 8 | 0.27440 | 1931 |
| 40 | 33.1892 | 2.69715 | 117 | 4 | 0.13600 | 629 |
| 41 | 33.5285 | 2.67062 | 541 | 20 | 0.37660 | 6972 |
| 42 | 34.3292 | 2.61014 | 199 | 8 | 0.27420 | 1922 |
| 43 | 34.7192 | 2.58171 | 193 | 7 | 0.25560 | 2081 |
| 44 | 35.6712 | 2.51496 | 445 | 17 | 0.42630 | 6493 |
| 45 | 36.5223 | 2.45828 | 160 | 6 | 0.25590 | 1373 |
| 46 | 37.1968 | 2.41524 | 90 | 3 | 0.37130 | 1130 |
| 47 | 37.9233 | 2.37063 | 442 | 17 | 0.25520 | 4021 |
| 48 | 38.2892 | 2.34881 | 204 | 8 | 0.21300 | 1700 |
| 49 | 38.9967 | 2.30781 | 113 | 4 | 0.21500 | 829 |
| 50 | 39.5034 | 2.27937 | 106 | 4 | 0.22350 | 771 |
| 51 | 39.8792 | 2.25875 | 127 | 5 | 0.11460 | 614 |

Differential Scanning Calorimetry and Thermal Gravimetric Analysis

Differential scanning calorimetry (DSC) and thermal gravimetric (TG) analyses were done on samples of Forms A, C and D using a heating rate of 10° C./minute from 25 to 250° C. FIGS. 2(A)-2(B), FIG. 6 and FIGS. 8(A)-8(B) show results of the thermal analyses.

Single Crystal Structure Determination

The single crystal structure of Form D was derived from X-ray crystallographic data obtained from a suitable single crystal of From D of compound 1 using Mo Kα radiation. The crystal structure was characterized as a P1 21/n1 space group:

$a$=14.3994(8) Å; $b$=5.7133(3) Å; $c$=23.872(3) Å;
$\beta$=102.130(3)°; and $V$=1920.1(2) Å$^3$.

The cell parameters for the unit cell are summarized in Table 4 above.

Synthesis of Polymorphs of Compound 1

Example 1

Preparation of Crystal Habit 1 of Form A of Compound 1

5 g of compound 1 was added to 125 mL of acetone. Into this mixture, was added 125 mL of de-ionized water. The resulting mixture was heated to 60° C. with stirring until reaching a clear solution. The resulting solution was then allowed to cool to ambient temperature and stirred for 4 days. The completion of formation of Crystal Habit 1 of Form A was checked with its IR spectrum. The resulting solid was isolated by filtration and dried under vacuum at 40° C. Needle type crystals obtained by the filtration process tended to be compressed into lumps during the drying process.

Example 2

Preparation of Crystal Habit 2 of Form A of Compound 1

Compound 1 was suspended in acetone (14 L/kg), and water (2 L/kg) was added into suspension with stirring until all solid was dissolved at ambient temperature. Water (30.4 L/kg) was added into a crystallization vessel and cooled to 0° C. The acetone/water solution of compound 1 was added to the water in crystallization vessel over 20-40 minutes while maintaining the temperature below 5° C. The resulting suspension was agitated for 20-24 hours at ambient temperature. The resulting solid was filtered washed with cold 50% aqueous acetone followed by n-heptane, and dried under vacuum at 50° C.

Example 3

Preparation of Form C of Compound 1

1 g of compound 1 was dissolved in about 270 mL of dichloromethane under reflux. The resulting solution was filtered through a 0.2 micron filter into a separate flask. The solution was slowly cooled to ambient temperature to promote crystallization. If necessary further cooling was applied to achieve and complete crystallization. The resulting solid was isolated by filtration and dried under vacuum at ambient temperature.

Alternatively, 5g of compound 1 was dissolved in 1350 mL of dichloromethane with stirring. The resulting solution was filtered through a 0.2 micron filter into a separate flask. The solution was cooled to 0° C. and agitated for 12-16 hours while maintaining the temperature of the solution at 0° C. The resulting solid was isolated by filtration, washed with cold (0-10° C.) 50% aqueous acetone and heptane, and dried under vacuum at 50° C. to yield 3-3.5 g of the product.

Example 4

Preparation of Form D of Compound 1

A. Method 1

5 g of compound 1 was dissolved in 70 mL (14 L/kg) of acetone and 10 mL (2 L/kg) of de-ionized water with stirring until reaching a clear solution at ambient temperature. 60 mL (12 L/kg) of de-ionized water was added to the acetone/water solution of compound 1 and the resulting mixture was stirred for 2-4 hours. Optionally, 5% (250 mg) of Form D of compound 1 was added prior or concurrently with addition of water. The solid was isolated by filtration, washed with cold (0-10° C.) 50% aqueous acetone and heptane, and dried under vacuum at 50° C. to yield 3.9.1-4.1 g of the product.

Alternatively, 5 g of compound 1 was dissolved in 70 mL (14 L/kg) of acetone and 10 mL (2 L/kg) of de-ionized water with stirring until reaching a clear solution at ambient temperature. Optionally, 5% (250 mg) of Form D of compound 1 as a seed(s) was added. 130 mL (26 L/kg) of de-ionized water was added to the acetone/water solution of compound 1 at ambient temperature and the resulting mixture was stirred for 8-12 hours allow the crystallization to complete. The resulting solid was isolated by filtration, washed with cold (0-10° C.) 50% aqueous acetone and heptane, and dried under vacuum at 50° C. to yield 4.1-4.3 g of the product.

B. Method 2

5 g of compound 1 was added to 125 mL of acetone. Into this mixture, was added 125 mL of de-ionized water. The resulting mixture was heated to 60° C. with stirring until reaching a clear solution. The resulting solution was then allowed to cool to ambient temperature and stirred for 2 hours. During the cooling process, crystals of Form D of compound 1 were precipitated. The resulting solid was isolated by filtration, and dried under vacuum at 40° C.

Example 5

Stability Study

Materials and Equipment:
20 mL scintillation vials
Weighing scale: Mettler Toledo XP 105DR
Stability Testing Sample Batch Preparation:

100 mg±2% of compound 1 was weighed into each 20mL scintillation vial. The vials were capped with appropriate caps and sealed with Parafilm to prevent moisture entrapment. Stability for the test compounds synthesized from different log was tested. Twelve vials for each lot were prepared and distributed into respective stability chambers to initiate their stability study according to the following protocol.

| Stability protocol | | |
|---|---|---|
| Time point (months) | 25° C./60% RH | 40° C./75% RH |
| 0.5 | NA | 1 vial (Appearance, HPLC) |
| 1 | 1 vial (Appearance, HPLC) | 1 vial (Appearance, HPLC) |
| 3 | 1 vial (Appearance, HPLC) | 1 vial (Appearance, HPLC) |
| 6 | 1 vial (Appearance, HPLC) | 1 vial (Appearance, HPLC) |
| 9 | 1 vial (Appearance, HPLC) | NA |
| 12 | 1 vial (Appearance, HPLC) | NA |
| 24 | 1 vial (Appearance, HPLC) | NA |
| All time points | 1 vial (IR only) | 1 vial (IR only) |

NA: Not applicable RH: relative humidity

Stability of the test compound was determined by its appearance and by analytical methods such as HPLC and IR. The IR test was performed for all time points under the two conditions listed above using material in one vial.

Compound 1 contains trace amount of compound 2 shown below. The amounts of compound 1 and 2 present at each time point were analyzed by HPLC.

(Compound 2)

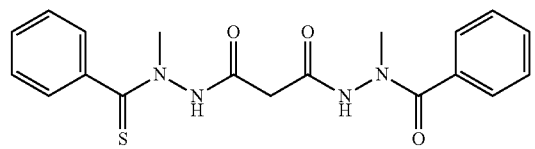

The stability data were listed in Tables 1-4.

TABLE 1

Stability data for Lot #1 at 25° C./60% RH

| | Time (Months) | | | | | | |
|---|---|---|---|---|---|---|---|
| | 0 | 0.5 | 1 | 3 | 6 | 9 | 12 |
| Appearance | Pale-yellow | NA | Pale-yellow | Pale-yellow | Pale yellow | Pale yellow | Pale yellow |
| FT-IR | Form D | NA | Form D | Form D | Form D | Form D | Form D |
| % compd 1 | 99.0 | NA | 98.8 | 99.0 | 99.0 | 97.5 | 98.0 |
| % compd 2 | 1.30 | NA | 1.28 | 1.31 | 1.28 | 1.38 | 1.33 |

TABLE 2

Stability data for Lot #1 at 40° C./75% RH

| Time (Months) | 0 | 0.5 | 1 | 3 | 6 |
|---|---|---|---|---|---|
| Appearance | Pale-yellow | Pale-yellow | Pale-yellow | Pale-yellow | Pale-yellow |
| FT-IR | Form D | Form D | Form D | Form D | Form D |
| % compd 1 | 99.0 | 99.7 | 95.8 | 98.9 | 98.4 |
| % compd 2 | 1.30 | 1.28 | 1.28 | 1.33 | 1.31 |

TABLE 3

Stability data for Lot #2 at 25° C./60% RH

| | Time (Months) | | | | | | |
|---|---|---|---|---|---|---|---|
| | 0 | 0.5 | 1 | 3 | 6 | 9 | 12 |
| Appearance | Pale-yellow powder | NA | Pale-yellow powder | Pale-yellow powder | Pale-yellow powder | Pale-yellow powder | Pale-yellow powder |
| FT-IR | Form D | NA | Form D | Form D | Form D | Form D | Form D |
| % compd 1 | 99.7 | NA | 98.6 | 100.2 | 99.6 | 98.9 | 99.7 |
| % compd 2 | 0.15 | NA | 0.14 | 0.15 | 0.13 | 0.13 | 0.13 |

TABLE 4

Stability data for Lot #2 at 40° C./75% RH

| Time (Months) | 0 | 0.5 | 1 | 3 | 6 |
|---|---|---|---|---|---|
| Appearance | Pale-yellow powder | Pale-yellow powder | Pale-yellow powder | Pale-yellow powder | Pale-yellow powder |
| FT-IR | Form D | Form D | Form D | Form D | Form D |
| % compd 1 | 99.7 | 99.6 | 100.3 | 100.2 | 101.7 |
| % compd 2 | 0.15 | 0.14 | 0.16 | 0.19 | 0.18 |

Example 6

Solubility Data

Solubility for Form A and Form D of compound 1 were measured and data are listed in Table 5.

TABLE 5

Solubility of Form A and Form D of compound 1.

| compound 1 | Shake Time (hour) | Solubility in EtOAc (mg/ml) | | | Solubility in EtOH (mg/ml) | | | Solubility in 50:50 Cre/EtOH (mg/ml) | | |
|---|---|---|---|---|---|---|---|---|---|---|
| | | Vial1 | Vial2 | Average | Vial1 | Vial2 | Average | Vial1 | Vial2 | Average |
| Form A | 24 | 4.69 | 4.69 | 4.7 | 6.28 | 6.45 | 6.4 | 24.37 | 24.28 | 24.3 |
| Form D | 24 | 7.41 | 7.50 | 7.5 | 9.76 | 9.75 | 9.8 | 42.69 | 42.74 | 42.7 |

Cre: Cremophor

Example 7

Characterization of Crystal Habit 1 and Crystal Habit 2 of Form A

Crystal Habit 1 and Crystal Habit 2 of Form A were characterized by their appearances, abilities to pass certain size of screen and reconstitution times according the procedures described below.

Reconstitution Test

50:50 Cremophor EL/Ethanol was prepared and filtered through a 0.45 μm filter and used for testing. 266 mg of compound 1 was weighed into a 50 mL glass vial with a rubber stopper. 16.7 ml of filtered 50:50 Cremophor EL/Ethanol solution was taken by a syringe and needle and added into the vial. The vial was shaken either manually, or on a mechanical shaker at a speed of 232-236 rpm. The reconstitution time was determined with three vials. At different time points, vials were subject to visual observation.

Sieve-Cut Test

Sieving was performed using Retsch oscillating shaker and 150 micron screen in two 5 minute intervals. 5 g to 20 g samples were used, depending on the batch size. The mass and percentage of material collected in the receiver were measured.

Optical Microscopy

Optical microscopy was performed using Olympus BX51 microscope equipped with DP71 color camera. 5×, 10× and 40× objectives were used to view samples. Samples were placed on a glass slide and tapped to obtain a single layer of particles. After an image of the tapped powder was acquired with 5× objective, a drop of silicon oil was added to the sample. A cover slip was gently placed over the sample, and the images were acquired with 5× and 10× objectives. A pressure was then applied to the cover slip to break the aggregates, and the images were acquired with 5× and 40× objectives. Images were acquired at ambient temperature using software DP-BSW.

Preparation of Crystal Habit I and Crystal Habit 2 of Form A

Batches 1 and 2 were prepared according to procedure a); batches of 3 and 4 were prepared according to procedure b); and batches 5-8 were prepared according to procedure c).

a) Compound 1 was suspended in acetone (14 L/Kg). Water (2 L/Kg) was added and the resulting mixture was stirred to dissolve solids. Water (12 L/Kg) was added to the clear solution. The solution was stirred for 14-16 hours until most of the solid precipitates. The slurry was cooled to 10° C. for 2-4 hours to complete precipitation. The solids were isolated by filtration, washed with cold 50% aq. acetone, then with cold mixture of acetone: n-heptane (1:2), and finally with n-heptane. The solid was dried at 50° C. under vacuum.

b) 125 mL of acetone and 125 mL of water were added to 5 g of compound 1. The mixture was heated to 60° C. until clear solution was obtained. The solution was cooled to room temperature. Solid precipitated during cooling. The resulting mixture was stirred for 4-6 days until complete transformation to Form A (filter the sample of the slurry and check completion of transformation to Form A by IR). The solid was filtered and dried at 40° C. under vacuum.

Alternatively, 5 g of compound 1 was dissolved in 70 mL (14 L/kg) of acetone and 10 mL (2 L/kg) of water with stirring. 60 mL (12 L/kg) of water was added and the resulting mixture was stirred for 4-6 days until complete transformation to Form A (filter the sample of the slurry and check completion of transformation to Form A by IR). The solid was filtered and dried at 40° C. under vacuum.

c) Compound 1 was suspended in acetone (14 L/Kg). Water (2 L/Kg) was added and stirred to dissolve solids to form a rich solution of compound 1. Water (30.4 L/Kg) was cooled to 0° C. and was added the rich solution of compound 1 while the temperature is maintained between 0-5° C. for 20-70 minutes. The suspension was warmed up to ambient temperature and agitated for 20-24 hours. Solids were isolated by filtration, washed twice with cold 50% aqueous acetone, and then with n-heptane and dried at 50° C. under vacuum.

Results

The results are listed in the Table 6 below.

TABLE 6

Characterization of Crystal Habit 1 and Crystal Habit 2 of Form A.

| Batch # | Habit # | Batch size | Appearance of particles | % by weight that passed through a specific size screen, % | Re-constitution time (min) for specific sieve-cut |
|---|---|---|---|---|---|
| 1 | 1 (granulated in the crystallizer) | 107 g | Oval to round aggregates that consist of needle type crystals | Does not pass through 300 micron screen | >>25, 500 micron sieve-cut |
| 2 | 1 (granulated in the crystallizer) | 1.67 Kg | Oval to round aggregates that consist of needle type crystals | Does not pass through 300 micron screen | >>25, 500 micron sieve-cut |
| 3 | 1 (loose crystals) | 5 g | Fine needles | ~23% (clogs the screen), 150 micron screen | 15, 150 micron sieve-cut |
| 4 | 1 (loose crystals) | 5 g | Fine needles | Does not pass through 150 micron screen (clogging). 42%, 500 micron screen | >>25, 500 micron sieve-cut |
| 5 | 2 (aggregates, formed in the crystallizer) | 30 g | "spherulites" | 98%, 150 micron screen | 10, 150 micron sieve-cut |

TABLE 6-continued

Characterization of Crystal Habit 1 and Crystal Habit 2 of Form A.

| Batch # | Habit # | Batch size | Appearance of particles | % by weight that passed through a specific size screen, % | Re-constitution time (min) for specific sieve-cut |
|---|---|---|---|---|---|
| 6 | 2 (aggregates, formed in the crystallizer) | 2.9 Kg | spherulites[a] | 98%, 150 micron screen | 5, 150 micron sieve-cut |
| 7 | 2 (aggregates, re-modeled in the filter dryer) | 4.6 kg | Oval to round aggregates | 95%, 150 micron screen | 7, 150 micron sieve-cut |
| 8 | 2 (aggregates, re-modeled in the filter dryer) | 3.7 kg | Aggregates of complex shape | 93%, 150 micron screen | 11, 150 micron sieve-cut |

[a]Aggregates of crystal habit 2 formed in the crystallizer are observed to be agglomerates of multiply nucleated radial aggregates (spherulites.) Such shape is preserved when the solids are being dried statically (batches 5 and 6). However, when the solids are dried in the filter dryer with continuous agitation, a certain re-modeling of the particles occurs, resulting in more smooth shapes as in cases of batches 7 and 8. In some cases though uncontrolled re-modeling in the filter can result in massive destruction of the aggregates leading to very fine particles mixed with very large particles.

Polarized light microscopy shows that Crystal Habit 1, granulated in the crystallizer (batches 1 and 2) consists of oval to round aggregates and a small portion of loose acicular particles (needles). Aggregates vary in length from 70 to 250 micron, and in width from 70 to 160 micron. Loose needles have length of approximately 3-27 micron, and width of approximately 0.7-2 micron (length to width aspect ratio ~4-13). When pressure is applied to the cover slip on the sample dispersed in oil, aggregates break into needles of the size described above.

Polarized light microscopy shows Crystal Habit 1 (batches 3 and 4) consists of fine needles that have length of approximately 4-41 micron, and width of approximately 0.8-4.2 micron (length to width aspect ratio 5-10).

Polarized light microscopy shows Crystal Habit 2 (batches 5 and 6) consists of agglomerates of multiply nucleated radial aggregates (spherulites). Aggregates vary in length from 34 to 135 micron, and in width from 17 to 120 micron (length to width aspect ratio 1-2).

Polarized light microscopy shows that when agitated in the filter dryer (batches 7 and 8), Crystal Habit 2 consists of partly re-modeled aggregates with various shapes, mostly oval shapes. Aggregates vary in length from 17 to 130 micron, and in width from 13 to 105 micron (length to width aspect ratio ~1.2).

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by the following Structural Formula:

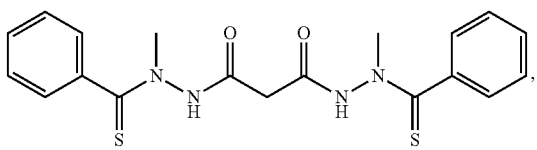 [SMILES: CN(NC(=O)CC(=O)NN(C)C(=S)c1ccccc1)C(=S)c1ccccc1]

wherein at least 70% by weight of the compound is a single crystalline form of Form A in habit 2 of the compound and the single crystalline form of Form A in habit 2 is characterized by at least one, two or three major X-ray powder diffraction peaks at 2θangle selected from the group consisting of 10.76°, 14.49° and 16.33°.

2. The compound of claim 1, wherein the single crystalline form of Form A in habit 2 is characterized by major X-ray powder diffraction peaks at 2θangles of 8.60°, 10.76°, 14.49°, 16.33°, 18.74°, 19.18°, 20.92°, 23.65° and 24.12°.

3. The compound of claim 1, wherein the single crystalline form of Form A in habit 2 is characterized by X-ray powder diffraction pattern of FIG. 1.

4. A pharmaceutical composition comprising a pharmaceutically acceptable carrier or diluent and a compound of claim 1.

5. A compound represented by the following Structural Formula:

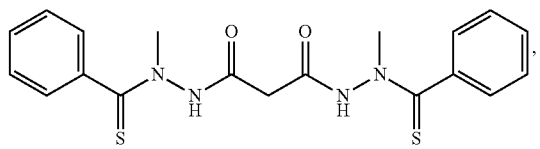 [SMILES: CN(NC(=O)CC(=O)NN(C)C(=S)c1ccccc1)C(=S)c1ccccc1]

wherein at least 70% by weight of the compound is a single crystalline form of Form C of the compound and the single crystalline form Form C is characterized by at least one, two, three, four or five major X-ray powder diffraction peaks at 2θangle selected from the group consisting of 10.32°, 14.80°, 21.49°, 23.05° and 30.12°.

6. A compound represented by the following Structural Formula:

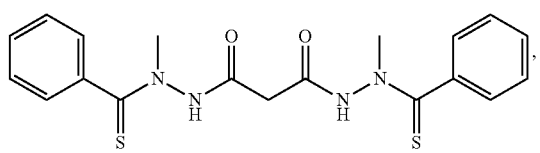 [SMILES: CN(NC(=O)CC(=O)NN(C)C(=S)c1ccccc1)C(=S)c1ccccc1]

wherein at least 70% by weight of compound is a single crystalline form of Form D of the compound and the single crystalline form Form D is characterized by at least one, three, five, seven, nine or eleven major X-ray powder diffraction peaks at 2θangle selected from the group consisting of 7.52°, 13.22°, 13.90°, 17.23°, 22.06°, 22.66°, 23.35°, 24.97°, 26.65°, 28.44° and 29.19°.

7. The compound of claim 5, wherein the single crystalline form Form C is characterized by major X-ray powder diffraction peaks at 2θ angles of 8.64°, 10.32°, 14.80°, 15.70°, 16.88°, 19.15°, 19.68°, 21.49°, 23.05°, 24.34° and 30.12°.

8. The compound of claim 5, wherein the single crystalline form Form C is characterized by X-ray powder diffraction pattern of FIG. 5.

9. The compound of claim 6, wherein the single crystalline form Form D is characterized by major X-ray powder diffraction peaks at 2θ angle of 7.52°, 7.84°, 13.22°, 13.90°, 15.82°, 16.75°, 17.23°, 18.70°, 19.71°, 20.80°, 22.06°, 22.66°, 23.35°, 23.74°, 24.07°, 24.31°, 24.97°, 26.65°, 28.44° and 29.19°.

10. The compound of claim 6, wherein the single crystalline form Form D is characterized by X-ray powder diffraction pattern of FIG. 7.

11. The compound of claim 6, wherein the single crystalline form Form D is characterized by the single crystal structure in P1 21/n1 space group and having unit cell parameters: a =14.4 ±0.1 Å; b =5.7 ±0.1 Å; c=23.9 ±0.1 Å; β=102.1 ± 0.1°; and V =1920 ±1 Å$^3$.

12. The compound of claim 1, wherein the crystal habit 2 is characterized by a polygon shape.

13. The compound of claim 1, wherein the crystal habit 2 has a length to width aspect ratio of greater than or equal to about 1 and less than or equal to about 2.

14. The compound of claim 1, wherein at least 70% by weight of the crystal habit 2 passes through a 150 micron screen.

15. The compound of claim 14, wherein the crystal habit 2 that passes through a 150 micron screen has a reconstitution time of less than 15 minutes.

16. The compound of claim 1, wherein the compound is substantially free of water and solvent.

17. The pharmaceutical composition of claim 4, wherein the compound is substantially free of water and solvent.

* * * * *

UNITED STATES PATENT AND TRADEMARK OFFICE
CERTIFICATE OF CORRECTION

Page 1 of 1

PATENT NO. : 8,637,704 B2
APPLICATION NO. : 12/745096
DATED : January 28, 2014
INVENTOR(S) : Kostik et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 597 days.

Signed and Sealed this
Second Day of June, 2015

Michelle K. Lee
*Director of the United States Patent and Trademark Office*